(12) United States Patent
Shaw et al.

(10) Patent No.: US 7,436,504 B2
(45) Date of Patent: Oct. 14, 2008

(54) NON-DESTRUCTIVE TESTING AND IMAGING

(75) Inventors: Eugene L. Shaw, Lake Orion, MI (US); Forrest S. Wright, Rochester, MI (US); David D. Malkan, Holly, MI (US)

(73) Assignee: Shear Graphics, LLC, Lake Orion, MI (US)

( * ) Notice: Subject to any disclaimer, the term of this patent is extended or adjusted under 35 U.S.C. 154(b) by 336 days.

(21) Appl. No.: 11/066,672

(22) Filed: Feb. 25, 2005

(65) Prior Publication Data

US 2005/0264796 A1    Dec. 1, 2005

Related U.S. Application Data

(63) Continuation-in-part of application No. 10/659,466, filed on Sep. 10, 2003, now Pat. No. 6,934,018.

(51) Int. Cl.
*G01N 21/00* (2006.01)

(52) U.S. Cl. .................................. 356/237.2

(58) Field of Classification Search .............. 356/237.2, 356/520, 237.1, 446–448, 35.5, 457, 458; 382/141; 348/125; 73/145
See application file for complete search history.

(56) References Cited

U.S. PATENT DOCUMENTS

| | | | |
|---|---|---|---|
| 3,816,649 A * | 6/1974 | Butters et al. ............... 348/161 |
| 4,093,382 A * | 6/1978 | Kurtz ........................ 356/72 |
| 4,506,981 A | 3/1985 | Hoff, Jr. |
| 4,702,594 A * | 10/1987 | Grant ........................ 356/35.5 |
| 4,887,899 A | 12/1989 | Hung |
| 5,065,331 A | 11/1991 | Vachon et al. |
| 5,307,139 A * | 4/1994 | Tyson et al. ................. 356/35.5 |
| 5,467,184 A * | 11/1995 | Tenjimbayashi .......... 356/35.5 |
| 5,473,434 A | 12/1995 | de Groot |
| 5,481,356 A | 1/1996 | Pouet et al. |
| 5,537,669 A * | 7/1996 | Evans et al. ................. 382/141 |
| 5,563,704 A * | 10/1996 | Fitzpatrick .................. 356/458 |
| 5,671,050 A | 9/1997 | de Groot |
| 5,760,888 A | 6/1998 | Rottenkolber |

(Continued)

FOREIGN PATENT DOCUMENTS

EP    1043578 A2    10/2000

OTHER PUBLICATIONS

Y, Y, Hung, etal Full-field Optical Strain Measurement having Postrecording Sensitivity and Direction Selectivity, Presented at 1975 SESA Spring Meeting, Chicago, IL May 11-16.

(Continued)

*Primary Examiner*—Michael P. Stafira
(74) *Attorney, Agent, or Firm*—William J Schramm

(57) ABSTRACT

A method of non-destructive testing includes non-destructively testing an object over a range of test levels, directing coherent light onto the object, directly receiving the coherent light substantially as reflected straight from the object, and capturing the reflected coherent light over the range of test levels as a plurality of digital images of the object. The method also includes calculating differences between pixel values of a plurality of pairs of digital images of the plurality of digital images, and adding the pixel value differences of the plurality of pairs of digital images to yield at least one cumulative differential image.

19 Claims, 74 Drawing Sheets

U.S. PATENT DOCUMENTS

| | | | |
|---|---|---|---|
| 5,826,319 A | 10/1998 | Colwell et al. | |
| 5,934,278 A * | 8/1999 | Ishihara et al. | 600/476 |
| 6,006,599 A | 12/1999 | Kelm-Klager et al. | |
| 6,012,329 A | 1/2000 | Kelm-Klager et al. | |
| 6,041,649 A | 3/2000 | Fembock | |
| 6,188,482 B1 | 2/2001 | Cloud | |
| 6,188,483 B1 | 2/2001 | Ettemeyer | |
| 6,268,923 B1 | 7/2001 | Michniewicz et al. | |
| 6,285,447 B1 * | 9/2001 | Parker et al. | 356/35.5 |
| 6,362,873 B1 | 3/2002 | Facchini et al. | |
| 6,366,358 B1 * | 4/2002 | Satou et al. | 358/1.14 |
| 6,433,874 B2 | 8/2002 | Lindsay et al. | |
| 6,493,092 B1 | 12/2002 | Marklund | |
| 6,496,254 B2 | 12/2002 | Bostrom et al. | |
| 6,522,410 B1 | 2/2003 | Marcus et al. | |
| 6,542,249 B1 | 4/2003 | Kofman et al. | |
| 6,556,290 B2 | 4/2003 | Maeda et al. | |
| 6,584,215 B1 * | 6/2003 | Mahner | 382/108 |
| 6,791,695 B2 | 9/2004 | Lindsey et al. | |
| 6,840,097 B1 | 1/2005 | Huber et al. | |
| 6,876,458 B2 | 4/2005 | Kraus | |
| 6,924,888 B2 | 8/2005 | Steinbichler et al. | |
| 7,194,630 B2 * | 3/2007 | Iwamura et al. | 713/176 |
| 2002/0135751 A1 * | 9/2002 | Steinbichler et al. | 356/35.5 |
| 2003/0161536 A1 * | 8/2003 | Iwamura et al. | 382/218 |
| 2004/0212795 A1 | 10/2004 | Steinbichler | |

OTHER PUBLICATIONS

Standard Prac. for Use of a Calibration Device to Demonstrate the Inspection Capability of an Interferometric Laser Imaging Nondestructive Tire Inspection System, ASTM 1364-92.

Wolfgang Steinchen and Lianxiang Yang, Digital Shearography Theory and Application of Digital Speckle Pattern Shearing Interferometry, 2003, pp. 30-35, SPIE Press.

AST 4000 Series Shearography Tire Inspection Systems, Laser Technology Inc. of Norristown, PA dated Sep. 1996.

* cited by examiner

NON-DESTRUCTIVE TESTING AND IMAGING

CROSS-REFERENCE TO RELATED APPLICATION

This application is a continuation-in-part of, and claims priority to U.S. patent application Ser. No. 10/659,466, filed Sep. 10, 2003, now U.S. Pat. No. 6,934,018 which is hereby incorporated by reference.

FIELD OF THE INVENTION

The present invention pertains to the field of Non-Destructive Testing (NDT) and its application to a variety of substrates and the ability to illuminate and capture reflected light efficiently from these substrates. In particular the invention pertains to such testing of tires, and utilizes a computer to display image test data.

BACKGROUND OF THE INVENTION

For many years the standard practice for calibrating shearographic/holographic tire testing machines has been ASTM F1364-92. This test method describes the construction and use of a calibration device for demonstrating the anomaly detection capability of an interferometric laser imaging non-destructive tire inspection system. A typical shearographic fringe pattern resulting from such testing technique is shown in FIG. 1.

As has been described in U.S. Pat. No. 6,433,874 the technique of shearing interferometry, or shearography involves the interference of two laterally-displaced images of the same object to form an interference image. Conventional shearographic methods require that a first interference image (or baseline image) be taken while the object is in an unstressed or first stressed condition, and another interference image be taken while the object is in a second stressed condition. Comparison of those two interference images (preferably by methods of image subtraction) reveals information about the strain concentrations and hence the integrity of the object in a single image called a shearogram. FIG. 1 shows an image which is the direct result of two laterally-displaced images being obtained by an interference technique. The images that are obtained are not to the scale of the anomaly in the tire. In addition very minute anomalies, those in the order of 1.7 mm are not readily ascertainable from a shearogram such as that shown in FIG. 1.

While some systems for shearography have an output such as the display of computerized systems of the '874 patent, many of the systems utilized are such that they have an output of highly sensitive film which is extremely costly and requires a special viewing device. Further, film based shearographic tire testing machines (and individual tire tests) are typically very expensive therefore a limited number are utilized in the industry within individual plants.

The electronic shearography of the '874 patent is based upon the shearography described in U.S. Pat. No. 4,887,899 which describes an apparatus which produces an interference image by passing light, reflected from the test object, through birefringent material and a polarizer. The birefringent material splits a light ray into two rays and polarizing it makes it possible for light rays reflected from a pair of points to interfere with each other. Thus each point on the object generates two rays and the result is an interference image formed by the optical interference of two laterally displaced images of the same object.

There is a need for a tire testing technique that facilitates direct measurement of anomalies in order for the anomalies to be quantified.

There is a need to obtain an output from tire testing equipment which does not rely upon an interferogram or proprietary optics, thereby making the output of such testing technique accurately describe and identify the anomaly.

There is a need for a tire testing technique and apparatus which permits the utilization of coherent light and the reflection of such light to be captured by inexpensive equipment and displayed using commonly available computerized systems.

It is accordingly an object of the invention to provide a new tire testing technique and apparatus which facilitates direct measurements, and a quantitative analysis or scalability of the anomaly in the tire.

It is an object of the present invention to provide a new tire testing technique and apparatus which does not rely upon an interferogram to accurately describe and identify the anomaly.

It is an object of the present invention to provide a new tire testing technique and apparatus which permits the utilization of coherent light and reflection of such light to be captured by inexpensive equipment and displayed using commonly available computerized systems which does not utilize laterally-displaced images but a single image of the anomaly as output.

SUMMARY OF THE INVENTION

An exemplary method of non-destructive testing includes non-destructively testing an object over a range of test levels, directing coherent light onto the object, directly receiving the coherent light substantially as reflected straight from the object, and capturing the reflected coherent light over the range of test levels as a plurality of digital images of the object. The exemplary method also includes calculating differences between pixel values of a plurality of pairs of digital images of the plurality of digital images, and adding the pixel value differences of the plurality of pairs of digital images to yield at least one cumulative differential image.

An exemplary computer-readable medium carries instructions to enable a processor to perform method steps of non-destructive testing. The method includes calculating differences between pixel values of a plurality of pairs of digital images captured as coherent light directly received substantially as reflected straight from an object undergoing non-destructive testing over a range of test levels, and adding the pixel value differences of the plurality of pairs of digital images to yield at least one cumulative differential image.

An exemplary method of creating a database of information from a non-destructive testing process of a plurality of objects is provided. The method includes creating a database record for each of the plurality of objects, wherein the database record includes the following information: at least one object identifier, at least one reference to at least one digital image, and at least one anomaly characteristic including at least one of anomaly quantity and anomaly size. The method also includes storing the database record for subsequent access.

An exemplary method of detecting an anomaly in a tire includes providing a source of coherent light, shining the light directly onto the tire surface thereby generating a reflected light from the tire, and stressing the tire over a range of test levels. The method also includes providing a reflected light receiving apparatus for receiving the light reflected directly from the tire when the tire is in a stressed and unstressed condition, and capturing the reflected light over the range of test levels as a plurality of digital images of the tire. The method additionally includes calculating differences between pixel values of a plurality of pairs of digital images of the plurality of digital images, and adding the pixel value differences of the plurality of pairs of digital images to yield at least one cumulative differential image. The method further includes providing a processor which views and compares images of reflected light from the reflected light receiving apparatus when the tire is stressed and unstressed thereby ascertaining an anomaly in the tire and generates an output from the comparison, and displaying the output from the processor using apparatus electronically connected to the processor.

An exemplary anomaly detector apparatus is provided for detecting an anomaly in a tire. The apparatus includes a source of coherent light to shine the light directly onto the tire surface with the light being reflected from the tire, a stressing apparatus to stress the tire over a range of test levels, a reflected light receiving apparatus for receiving the light reflected directly from the tire when the tire is in a stressed and unstressed condition. The apparatus also includes a processor, which compares images of reflected light from the reflected light receiving apparatus when the tire is stressed and unstressed thereby ascertaining an anomaly in the tire and which generates an output from the comparison. The processor is adapted to capture the reflected light over the range of test levels as a plurality of digital images of the tire, calculate differences between pixel values of a plurality of pairs of digital images of the plurality of digital images, and add the pixel value differences of the plurality of pairs of digital images to yield at least one cumulative differential image. The apparatus further includes a display apparatus electronically connected to the processor for displaying the output from the processor.

An exemplary non-destructive testing system includes a non-destructive testing apparatus to test an object over a range of test levels, a light source to direct coherent light onto the object, an imaging device to directly receive light substantially as reflected straight from the object and thereby capture a plurality of digital images of the object over the range of test levels, and a memory for storing the plurality of digital images and for storing a computer-executable program. The system also includes an input device for receiving input from an operator, an output device for transmitting output to the operator, and a processor in communication with the imaging device, the memory, and the input and output devices. The processor is adapted to execute the computer-executable program to store the plurality of images in the memory, calculate differences between pixel values of a plurality of pairs of digital images of the plurality of digital images, and add the pixel value differences of the plurality of pairs of digital images to yield at least one cumulative differential image.

BRIEF DESCRIPTION OF THE DRAWINGS

These and other objects, features and advantages of this invention will be apparent from the following detailed description, appended claims and accompanied drawings in which;

FIGS. 20 through 28 are graphical user interface screen shots that illustrate additional functionality of the human machine interface of the differencing video system of FIG. 12;

FIGS. 64 through 68 are graphical user interface screen shots that illustrate functionality of the substrate data collector of FIG. 12.

DETAILED DESCRIPTION OF THE INVENTION

Definitions

Figure 1:
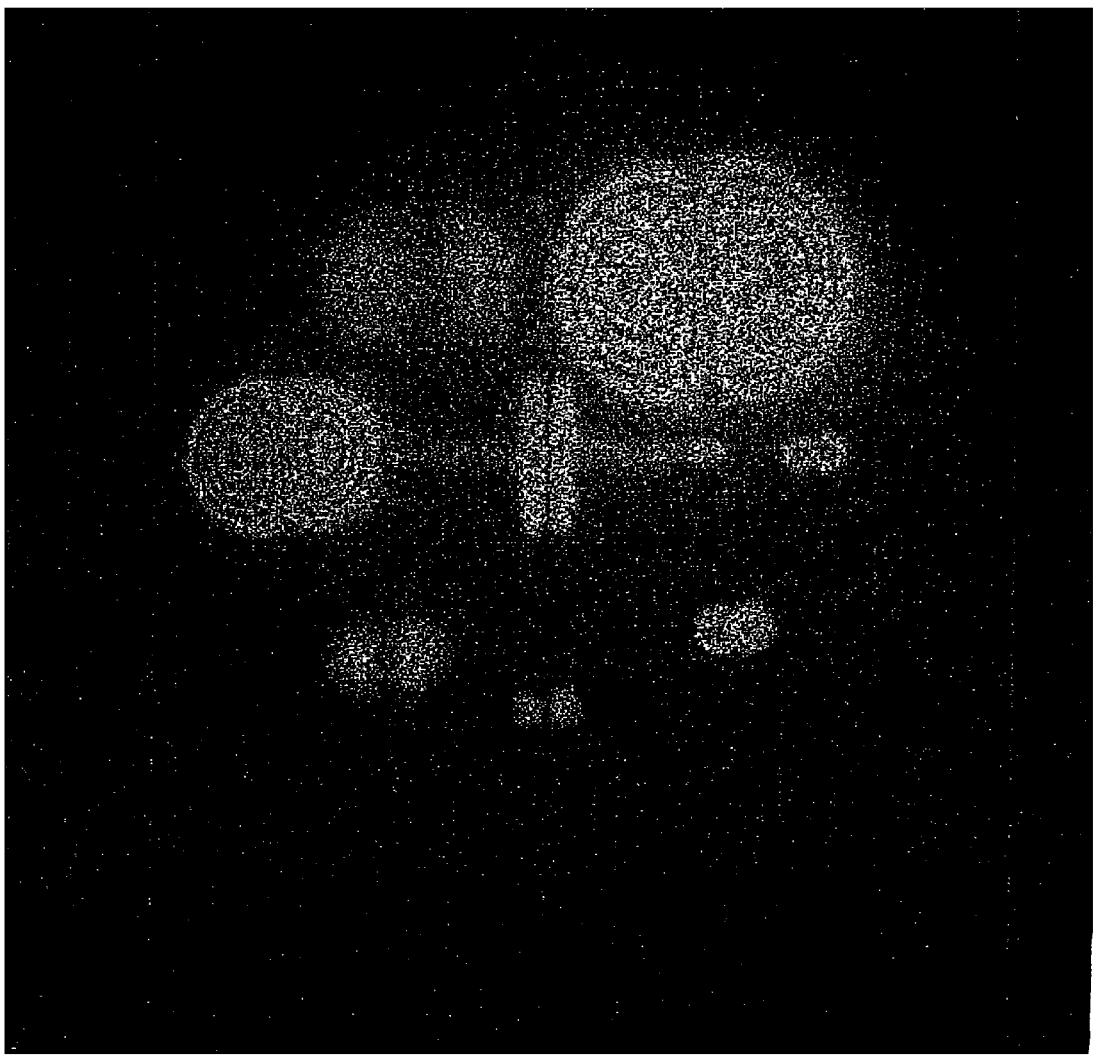
FIG. 1 is a prior art shearogram obtained from a testing fixture identified in ASTM F 1364-92.

Anomaly is defined as a defect in a tire which can generally be characterized as air trapped in a cured tire as a result of variations in the thickness of the tire components; porosity and voids in the tire, a separation, an undercure of the tire, trapped air and bubbles; low interply adhesion, poor cord adhesion, bare wires, broken cords, and machine building errors.

Bitmap is a data file or structure which corresponds bit for bit with an image displayed on a screen, preferably in the same format as it would be stored in the display's video memory or alternatively as a device independent bitmap. A bitmap is characterized by the width and height of the image in pixels and the number of bits per pixel which determines the number of shades of grey or colors it can represent.

Coherent light is a light having a single wavelength, frequency and phase. It is also radiant electromagnetic energy of the same, or almost the same wavelength, and with definite phase relationships between different points in the field.

Differenced or also known as delta frame means an animation frame that contains only the pixels different from the preceding key frame.

Diffuser is an apparatus which transmits light through a translucent material which permits the distribution of incident light onto the tire to be tested.

Interferometer is an instrument in which light from a source is split into two or more beams which are subsequently reunited after traveling over different paths and display interferences.

Laser is a device that produces a beam of coherent or monochromatic light as a result of photon-stimulated emission. Such beams have a single wavelength and frequency. Materials capable of producing this effect are certain high period crystals such as ruby, yttrium garnet, metallic tungstates or molybdates doped with rare earth ions; semi-conductors such as gallium arsenide, neodymium-doped glass; various gasses, including carbon dioxide, helium, argon, neon, and plasmas, and the like.

Laterally-displaced is a term that means, what appears to be a double or side by side image but is actually a positive and negative optical interference of a single anomaly. Further laterally means side by side but depending on the orientation of the optical element in the device could be any angle.

In this form of Non-Destructive Testing (NDT), non-destructive means a testing technique where the object to be tested is subjected to a stressing element and at the end of the testing the object is reverted to substantially its original condition.

The processor is a device or software, usually a central processing unit (CPU); it can also be a program that transforms some input into some output such as a computer or linkage editor; it facilitates the comparisons of images; it may be a hardwired device using embedded instructions to perform the comparisons.

Stressing element means an element that is used to apply stress or strain to an object to cause a change from its original condition. Such stressing can take the form of the application of a vacuum, the application of light, the application of a gas, the application of a mechanical force to permit flexing, the application of acoustical sound thereby vibrating the tire, or some other vibrating technique, or application of heat, or the like.

Reference is made to co-pending U.S. patent application Ser. No. 11/067,256, entitled A PLURALITY OF LIGHT SOURCES FOR INSPECTION APPARATUS AND METHOD, filed Feb. 25, 2005, now U.S. Pat. No. 7,187,437, which is hereby incorporated by reference herein.

In general, the apparatus and method of the present invention can be described as follows:

The inside surface of the tire is a diffuse reflective surface, compared to a mirror which is a specular reflective surface. A speckle pattern is visible on diffuse rather than specular reflective surfaces that is illuminated with laser light. These reflections from the anomalous regions change during the stressing cycle as the surface deforms. With multiple images captured by the camera during this cycle, the computer can process the image information using a software algorithm such as that described in FIG. 4A and FIG. 4B. In the present invention light does not pass through a birefringent material or a shearing optic material.

A typical test setup for the present invention is described as follows: The tire to be inspected is placed horizontally on a plate within a vacuum chamber. A commonly available industrial digital camera sits in the center of the tire so as to view a region of the inside surface of the tire such as camera model LU-205C available from Lumenera Corporation of Ottawa, Ontario, Canada (Lumenera.com) which is a color 2.0 megapixel having SVGA (800×600) sub-sampling which provides 40 frames/sec. The digital camera uses a commonly available lens to set the focus of the reflected speckle pattern image of the tire region on the digital image sensor. Preferably, the lens is adjusted so that the image is out of focus. The lens is preferably turned as far as possible towards a "near" setting of the lens (e.g. counter-clockwise when looking at the camera and lens).

A cable connects the camera to a computer. Image information is sent through this cable to the computer memory. Images from memory can be viewed on the computer display in near real-time, i.e., as the images are captured and processed by the equipment.

Generally each image will be stored in memory as a black/white bitmap file whereby 8 bits are used to store the gray-scale levels of each image sensor picture element, or pixel, value. Likewise, the images viewed on the computer display will be of the form of 8-bit, gray-scale, bitmap display images corresponding to the bitmap images, as the images are stored in memory. There are $2^8=256$ (from 0 to 255 decimal) possible gray-scale 8-bit values associated with each pixel of the displayed images. The decimal value, "0," as it directly represents the gray-scale level of individual display image pixels, corresponds to a black pixel, the darkest gray-scale pixel. Similarly, the decimal value, "255," represents the lightest gray-scale pixel, which is "white." The remaining numeric values between 0 and 255 represent a progression of gray levels from dark to light.

Note that two digital images that are exactly equivalent will have the same numeric values, from 0 to 255, for every image pixel.

Conversely, two digital images that are not equivalent will not have the same numeric values for every image pixel. The arithmetic difference between every corresponding image pixel of two exactly equivalent digital images will be 0. This means that the difference image obtained from differencing two equivalent digital images will be displayed as a totally black image. The difference image obtained from differencing two dissimilar digital images will not be a totally black image. The image differencing function provides a tool for observing slight changes between two digital images.

In one embodiment the stressing element is the use of vacuum. The speckle pattern associated with a given region of a tire will change with very small deformations of the tire surface. Such surface deformation occurs when the pressure drops in the vacuum test chamber and the air inside of a ply separation expands creating a deformation on the interior tire surface.

Practically speaking the two speckle pattern images of a tire surface region where there exists an underlying localized ply separation will be different if the two images are taken at different vacuum levels. Also the images will only, or at least ideally, be numerically different in the deformation region associated with the ply separation. The difference image of the two images will be black everywhere except the area where the deformation occurs. In the deformation region of the image there will be grey pixels of various shades. The deformation region is visible in the differenced image.

In one embodiment of the test method, six digital images of a laser illuminated interior surface region of a tire are taken with each image taken at one-of-six vacuum levels. The laser is a gallium arsenide laser having a wavelength of 808 nm (nanometer), model UH5-200 808 supplied by World Star Tech. of Toronto, Ontario, Canada (worldstartech.com). The first image will be taken at 0.0" Hg (atmospheric pressure). This first image will be called the base image. The five remaining images will be taken respectively at 0.5, 1.0, 1.5, 2.0, and finally 2.5" Hg. The six images will be stored in computer memory. Next five differenced images will be obtained using the base image always as one of the two images to be differenced. The other images used to make the five differenced images will be the five non-base images. Each of the five differenced images will be processed to filter out noise and increase contrast/brightness. Other processing may also be used. Any combination of available or custom image processing software including: auto anomaly detection, special effects, filtering, noise reduction, sharpening, dilation, colorization, positive or negative or the like. The five processed images will be added together in an accumulative fashion. After each addition of two images, the new image formed by the addition will be processed. The final image will be used for evaluation for the given tire region. There will be a plurality of inspection regions inspected using the preferred test method in order to evaluate the complete tire.

It is to be appreciated that a display is meant to cover varied electronic output of the images whether visible to the naked eye or not and includes a screen display, hard copy or an electronic image. The electronic image may be used by a computer to determine whether the test object passes or fails testing criteria without actually displaying the image to the naked eye or optionally without operator intervention.

Turning now to the drawings in the case.

FIG. 1 is a prior art shearogram obtained from the testing fixture identified in ASTM F 1364-92. For ease of readability, FIG. 1 is a black on white image as opposed to a white on black image which is one output from the ASTM test. It should be noted that the anomalies in that output are laterally-displaced images.

Figure 2:
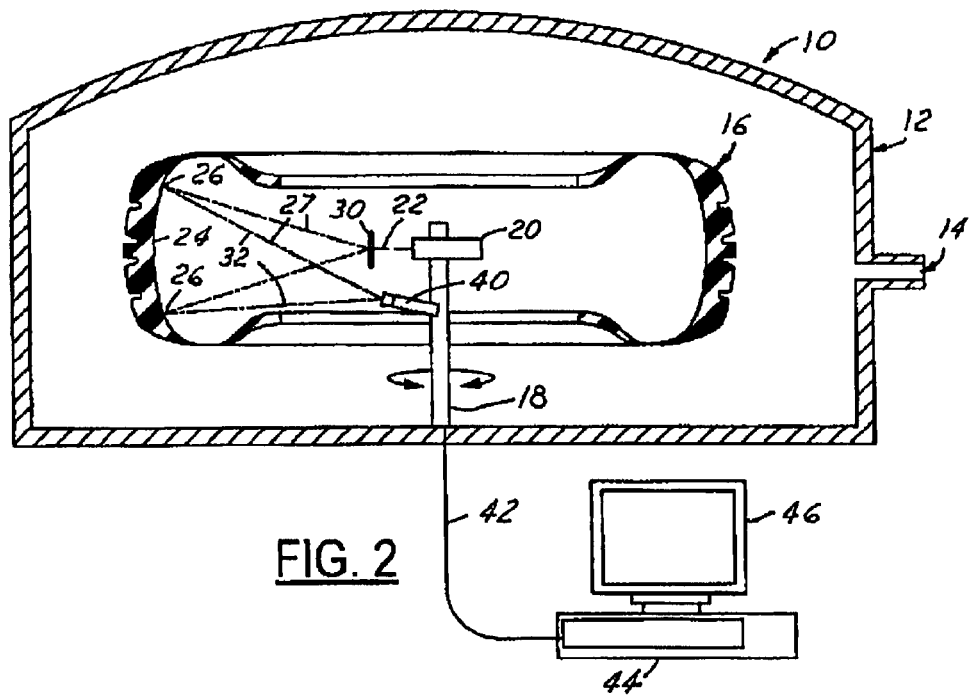
FIG. 2 is a schematic representation of the apparatus of the present invention.

FIG. 2 is a schematic diagram of the anomaly detector apparatus of the present invention. In general, the anomaly detector apparatus 10 is encased within a vacuum chamber 12 which is indicated as having a vacuum outlet 14. The tire 16 can be placed on a carrying member (not shown) and can be placed on a motorized conveyer (not shown) outside the vacuum chamber and moved into the vacuum chamber. Such techniques are well known in the art. The anomaly detector apparatus is comprised of the laser 20 mounted on a shaft 18 which can be rotated as well as moved forwards and back in the vacuum apparatus. The coherent light 22 emitted from the laser 20 reflects on the inner surface 24 of the tire at points 26 as well as numerous other points. The coherent light 22 from the laser 18 is passed through a diffuser 30 which facilitates the spreading of the light across the portions of the tire substrate 24 to be viewed. The diffused light 27 is reflected off of the points 26 in a speckled fashion which is reflected off of the substrate 24 as shown by beams 32. The light is speckled and is captured in a camera 40. Preferably, the camera or cameras are a CCD variety well known in the industry as a charged coupled device. Other photosensitive detection equipment may be utilized. The camera can be called an image sensor, namely, it senses the speckled image 32 from the application of direct laser light onto the tire surface 24.

The diffuser is a holographic diffuser of 25 mm diameter with relatively high diffuser transmission efficiency. Alternatively the diffuser may be opal diffusing glass having a diameter of 25 millimeter, both available from Edmund Industrial Optics of Barrington, N.J.

The camera and the computer are electrically connected through wire 42. It is to be appreciated that while electrical current may be necessary for the operation of the laser and the camera, the output from the camera could likewise be supplied to the computer 44 by well known wireless communication techniques represented by parallel lines 43. The computer hard drive 44 with a video card is attached to a monitor 46 for display of the speckled output 32.

Figure 3A:
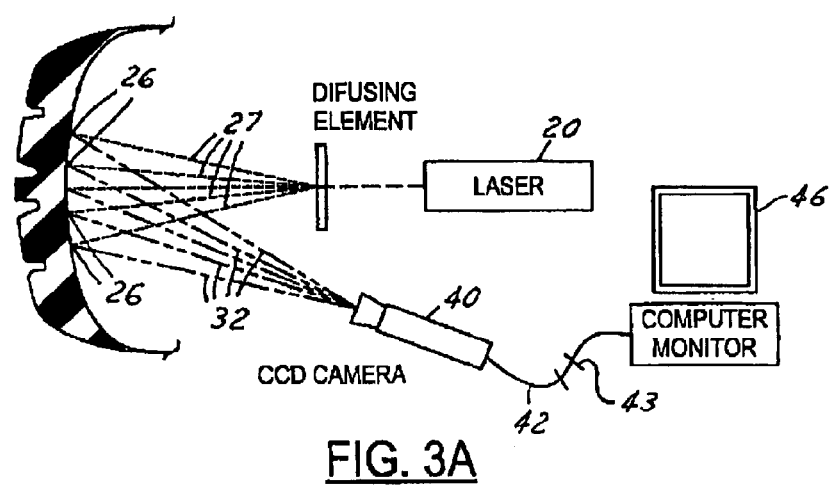
FIG. 3A is a schematic drawing of the tire testing equipment where the tire is in an unstressed condition.
Figure 3B:
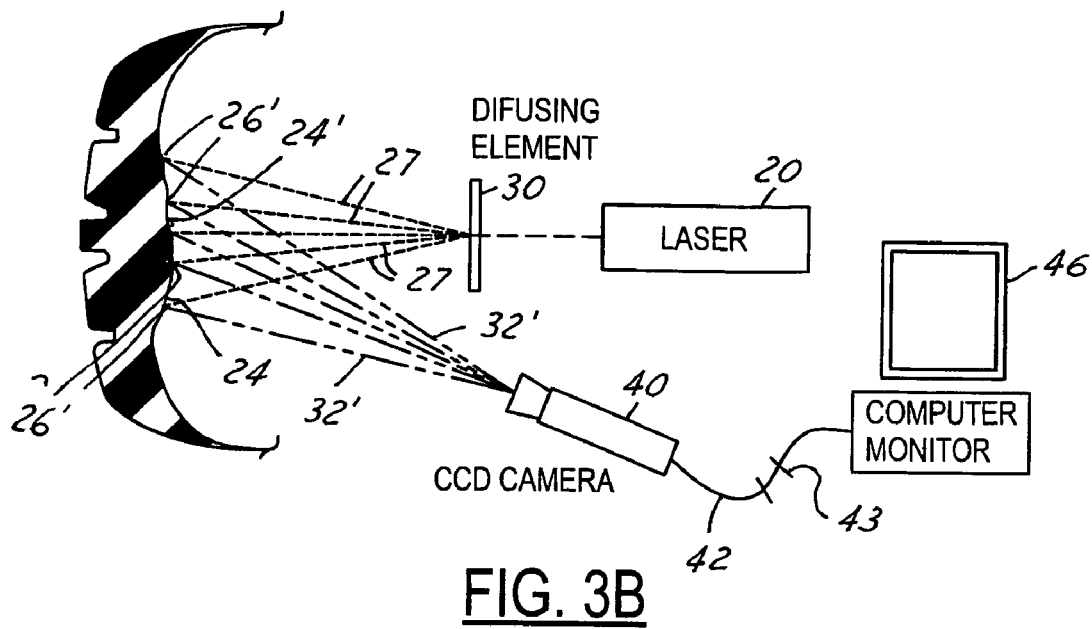
FIG. 3B is a schematic drawing of the tire testing equipment where the tire is in a stressed condition.

It is to be appreciated that the coherent laser light that is diffused onto the substrate 24 is reflected off of the substrate and the capturing is a direct capture of the reflections 32 by the CCD 40. This is unlike that which is utilized in prior art shearograms or interferometry which use an optical shearing device. The direct output of the device shown in FIGS. 2, 3A and 3B is that shown in FIG. 5. It is to be appreciated that the output of FIG. 5 can be either black on white or white on black depending on how one wishes to view the desired output. Because the image is captured by an image sensor, each pixel of the image can be identified or stored in digital form, as such, one can assign colors to different portions of the image, besides a white or black color thereby enhancing the image.

In a similar fashion, the operation of the equipment is shown in FIGS. 3A and 3B where there are larger number of diffused rays 27 at different points 26. The light 27 from the diffusing element 30 is dispersed as is shown in FIGS. 2, 3A and 3B.

After the tire is subjected to a stressing element such as application of a vacuum, the application of light, the application of gas, the application of a mechanical force to permit flexing, the application of acoustical sound thereby vibrating the tire or some other vibrating or heat application technique, the result is the movement of the tire substrate 24 which in turn causes a reflection of the laser light from points 26. FIG. 3B shows in an exaggerated fashion the variation from the smooth surface 24 of the tire to an expanded version or deformation 24 that is depicted. The laser light therefore is deflected at a different angle and therefore is shown as reflected speckled light 32 which creates images that are captured by the CCD camera 40.

The electrical cable 42 is shown as having parallel marks 43 to indicate that there may not necessarily be a direct wire for passing the images from the camera to the computer monitor but may be done by a wireless technique. The capturing of images on a camera is well known in the art. It can take the form of animation of images, which techniques are well known.

Figures 4A, 4B:
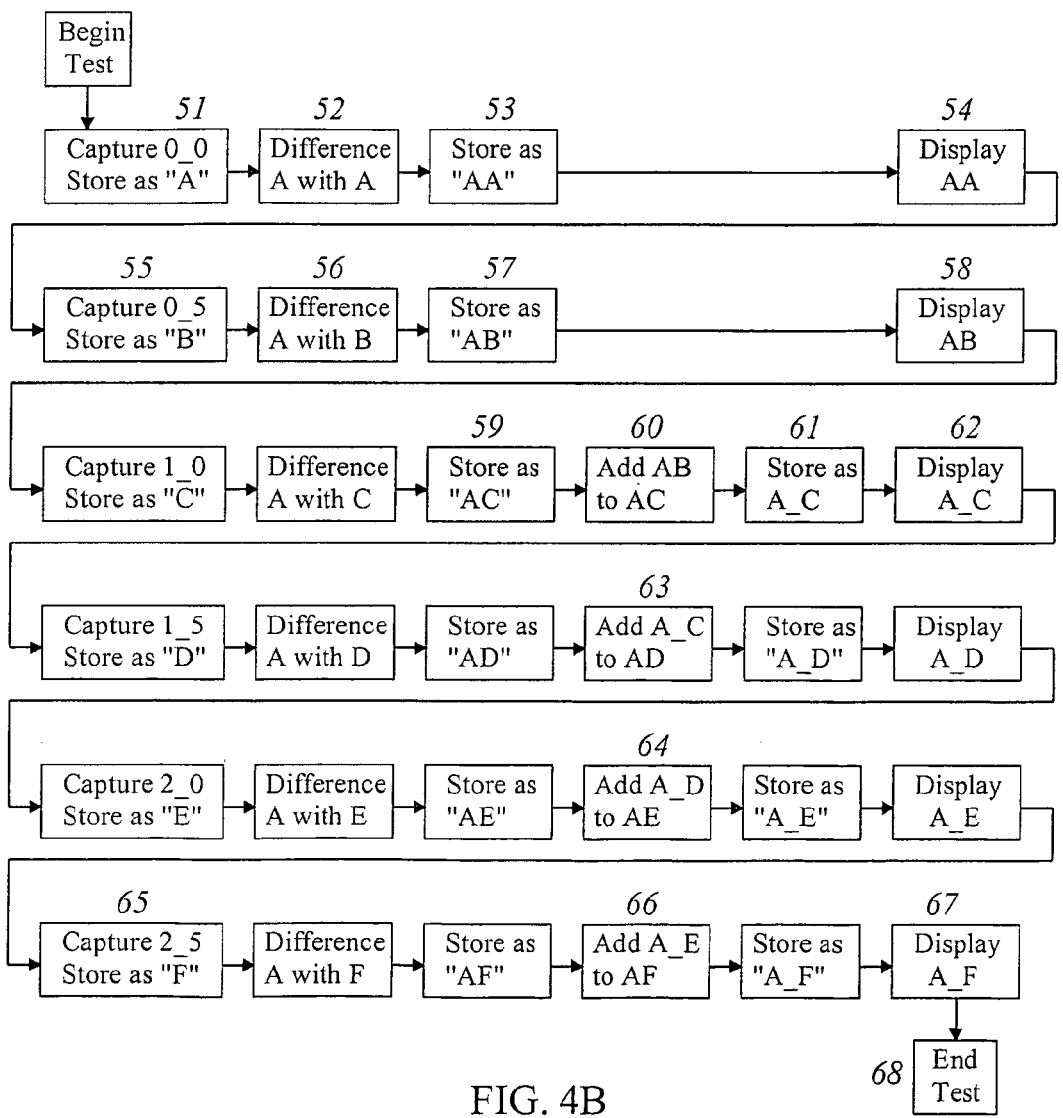
FIG. 4A is a legend for FIG. 4B. This legend serves to name the images captured with the tire subjected to various levels during the sequence of steps used in FIG. 4B.
FIG. 4B is a block diagram of the sequences of computations of a computer to capture and process different images of the unstressed and stressed conditions as the typical stressing conditions are applied, such as an application of vacuum.
Figure 5:
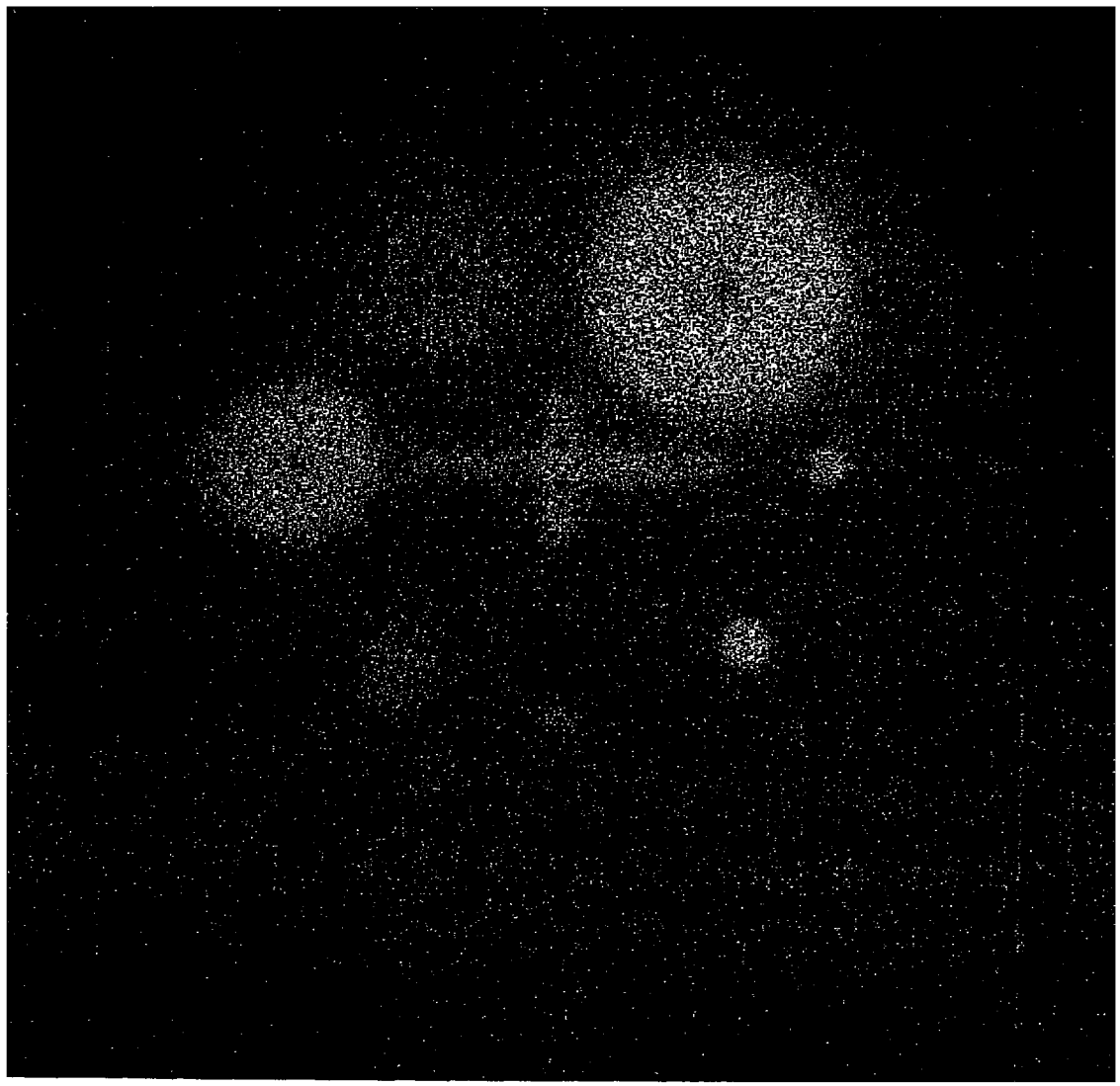
FIG. 5 is a typical output of the tire testing apparatus showing a calibration block used as the test object, and method of the present invention.

To graphically explain how the animation occurs reference can be made to FIGS. 4A and 4B. FIG. 4A shows a legend whereby images that are captured at various vacuum levels are given names for reference purposes. FIG. 4B shows the sequence of steps used for evaluating one region of the inside surface of a tire. The test sequence begins at the box designated as 50 and ends at step 68. At 51 the base image of the tire region is captured while the tire is unstressed and subjected to 0.0" Hg (atmospheric pressure). From the legend shown in FIG. 4A, this image is designated 0__0. This base image, referenced as 0__0, is stored as image "A" during step 51. For consistency, at box 52, the base image is differenced with itself to provide a black image that is displayed as the first image of the animation. This image is stored at 53 as "AA". It can be appreciated that a black image could have been produced in software without actually imaging the tire region, however, the base image "A" is captured since it is used in subsequent steps of the test sequence. After image AA is displayed at 54 the next image is captured at step 55 while the tire is subjected to 0.5" Hg vacuum. This image, "0__5," is stored as "B" in step 55. At 56 the image, B, is differenced with the base image, A, producing image, "AB," which is stored in step 57. AB is then displayed at 58 and AB serves as the 2$^{nd}$ image in the animation sequence. At step 60, as well as subsequent steps, 63, 64, 66, the previously displayed image is added to the image formed in the immediately preceding steps. For example, at step 60, the previously displayed image is AB and the image added to this image is the just-formed image, "AC" stored at step 59. The newly formed image is stored as "A_C" at step 61. A_C is then displayed at step 62. During the course of the test, images are captured at 0.5" Hg increments with the final image, "2__5," being captured with the tire subjected to 2.5" Hg vacuum (step 65). At 67 the final image in the animation sequence is displayed. The Images obtained during the tire test can be the subject of a printed output as shown in FIG. 5. A representative of such a technique is shown at FIG. 5 where the procedure, as followed in the ASTM testing technique described above, was utilized, except the apparatus of FIGS. 1 and 2 were used in place of an interferometer technique.

It is also to be understood that even though FIGS. 4A and 4B. show the vacuum cycle from 0.0" Hg. to 2.5" Hg, any combination of vacuum levels or set points increasing or decreasing may be used. As an example from 5.5" Hg. to 1.0" Hg.

In another embodiment of the invention, an assembly 104 including a plurality of reflected light receiving apparatus for receiving the light reflected is utilized such as that shown in FIGS. 6-8A. In this embodiment, the anomaly detector apparatus 10 is modified by redesigning the assembly of the source of coherent light 18 to better facilitate the light distribution on the inside of the outside of a hollow toroidal surface i.e. the inside of a tire, and the light receiving apparatus 40 to receive the light from the inside of the outside of a hollow toroidal surface.

Figure 6:
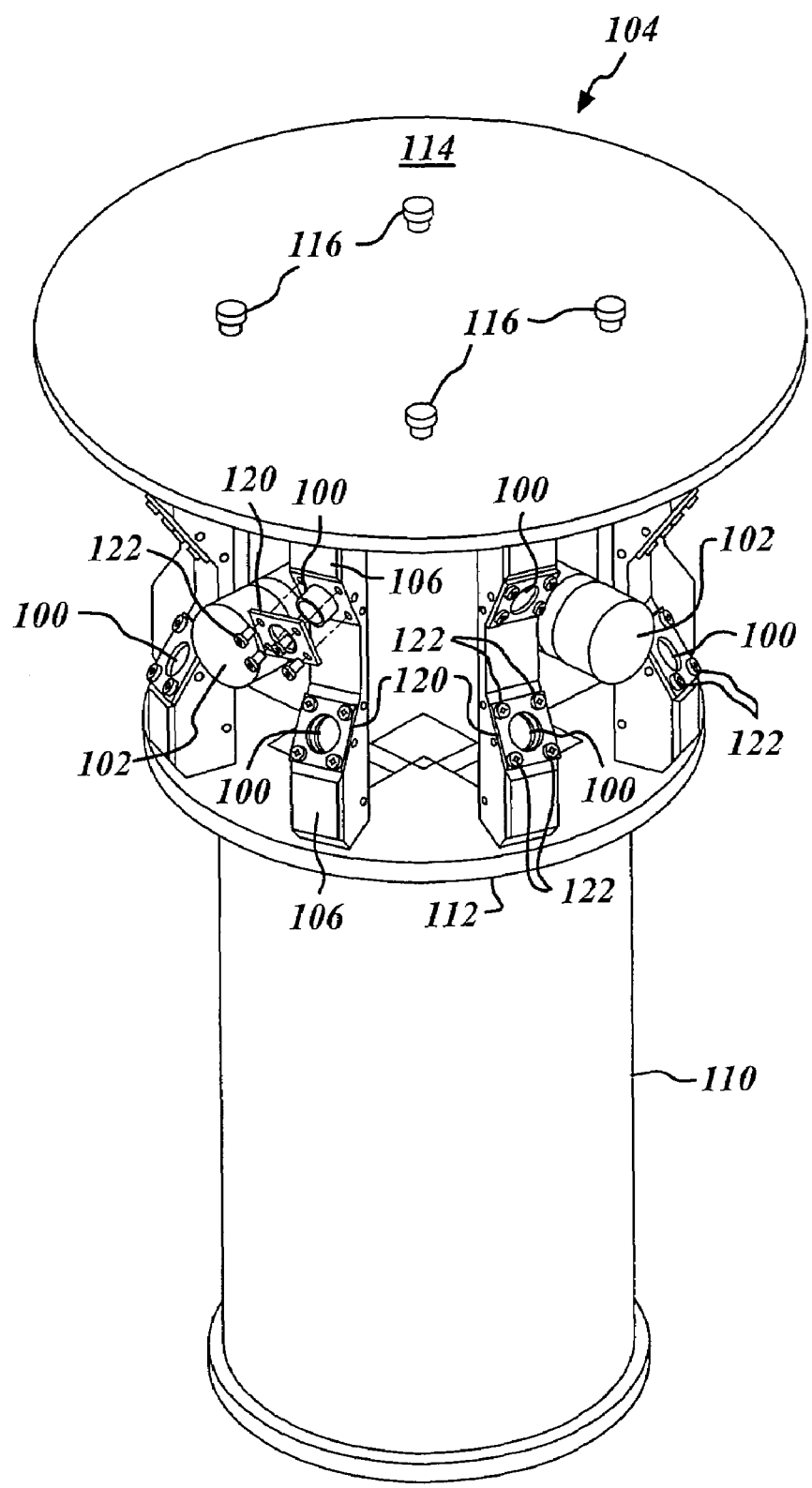
FIG. 6 is a perspective view of a portion of one embodiment of the apparatus of the present invention.
Figure 7:
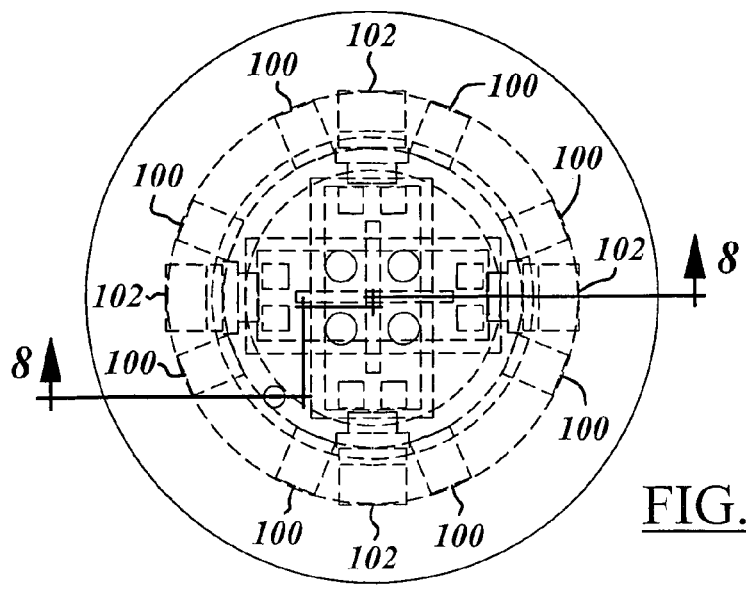
FIG. 7 is top sectional view of the apparatus of FIG. 6.
Figure 8:
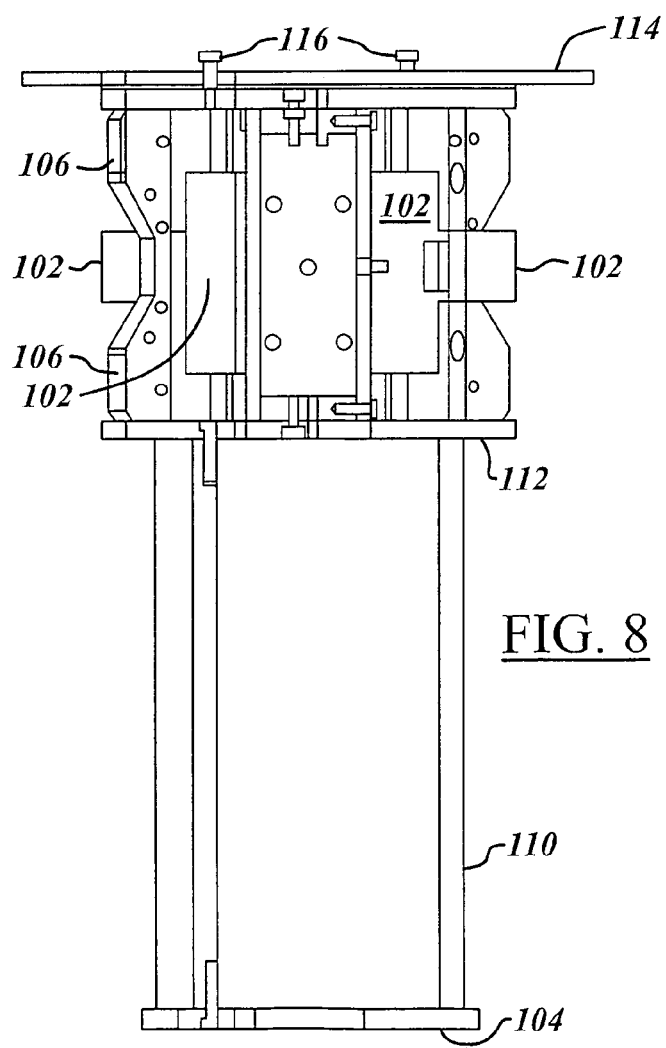
FIG. 8 is a sectional view of FIG. 7 taken along lines 8-8 of FIG. 7.

In FIGS. 6-8A, there are multiple lasers 100, which are located substantially adjacent to the light receiving apparatus 102 preferably a camera. The camera or cameras as shown in FIGS. 6-8 are four in number circumferentially evenly located about a circle sitting atop a mounting plate 112 which moves up and down whenever a horizontally placed tire is inserted into the testing apparatus 10. In one embodiment a CCD camera 102 employed is LUMENERA camera LU105M supplied by Lumenera Corporation because of it's thin cross section and the need to have several components back to back in a small space inside the test object (tire).

It is to be appreciated that the number of receiving apparatus 102, and the number of lasers 100 and the number and style of light shaping diffusers can vary depending upon the size of the substrate to be studied, such as 2 to 8 cameras, preferably 4-6. As can be seen from FIG. 6, the lasers point in a direction both upwards, downwards and outwards or could be any combination of angles to suit the shape of the test object through a light shaping elliptical diffuser (not shown) fitting within retaining member 106. As can be seen from FIGS. 6 and 7, the sources of coherent light 100 are placed on each side of the light receiving apparatus 102. Preferably the angle of the source of the lasers to the axis of the light receiving apparatus can vary from 10 to 45 degrees, preferably 20 to 45 degrees (as best seen from top view of FIG. 7).

Figure 8A:
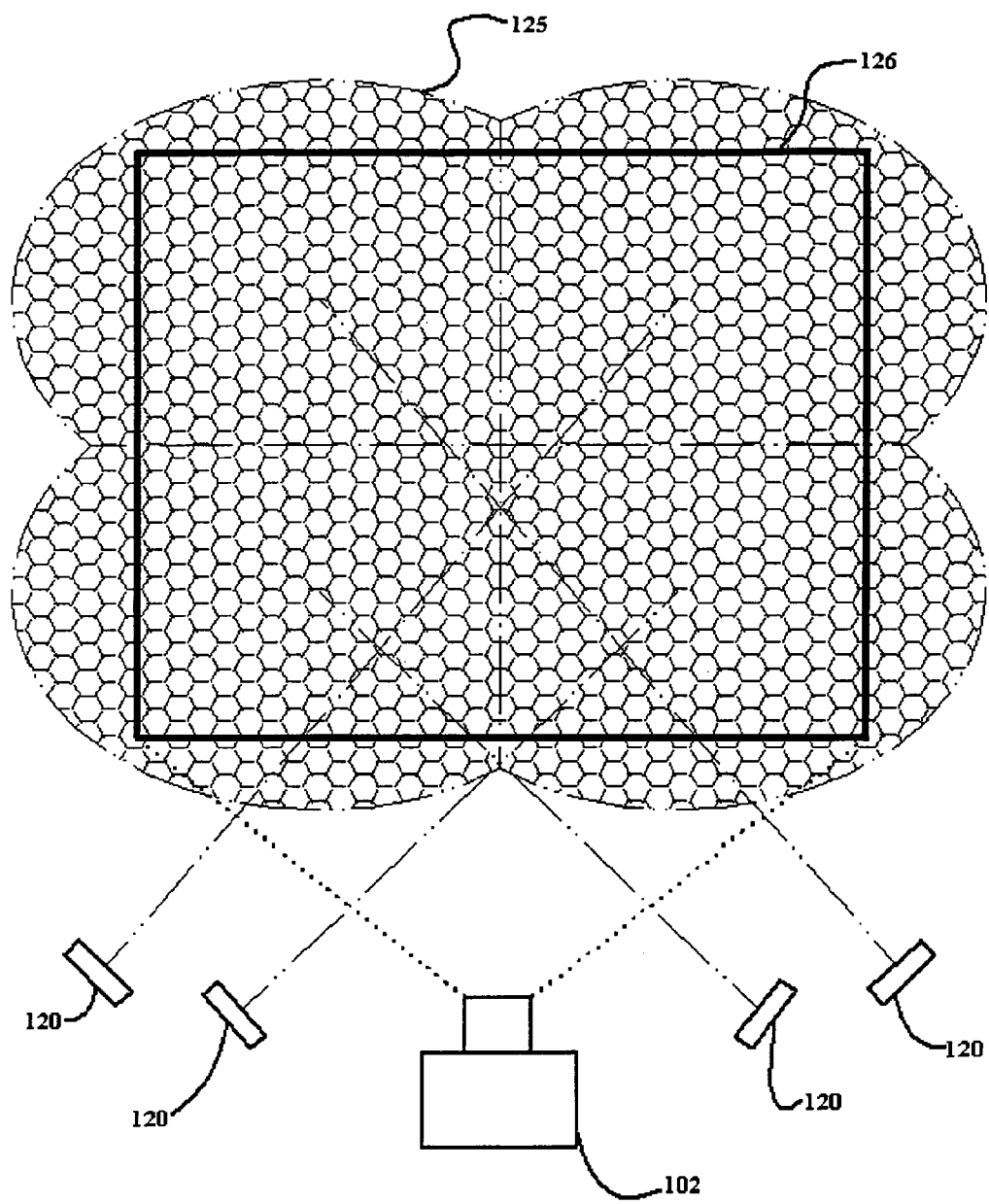
FIG. 8A is schematic diagram of an imaging arrangement of the apparatus of FIG. 6.
Figure 8B:
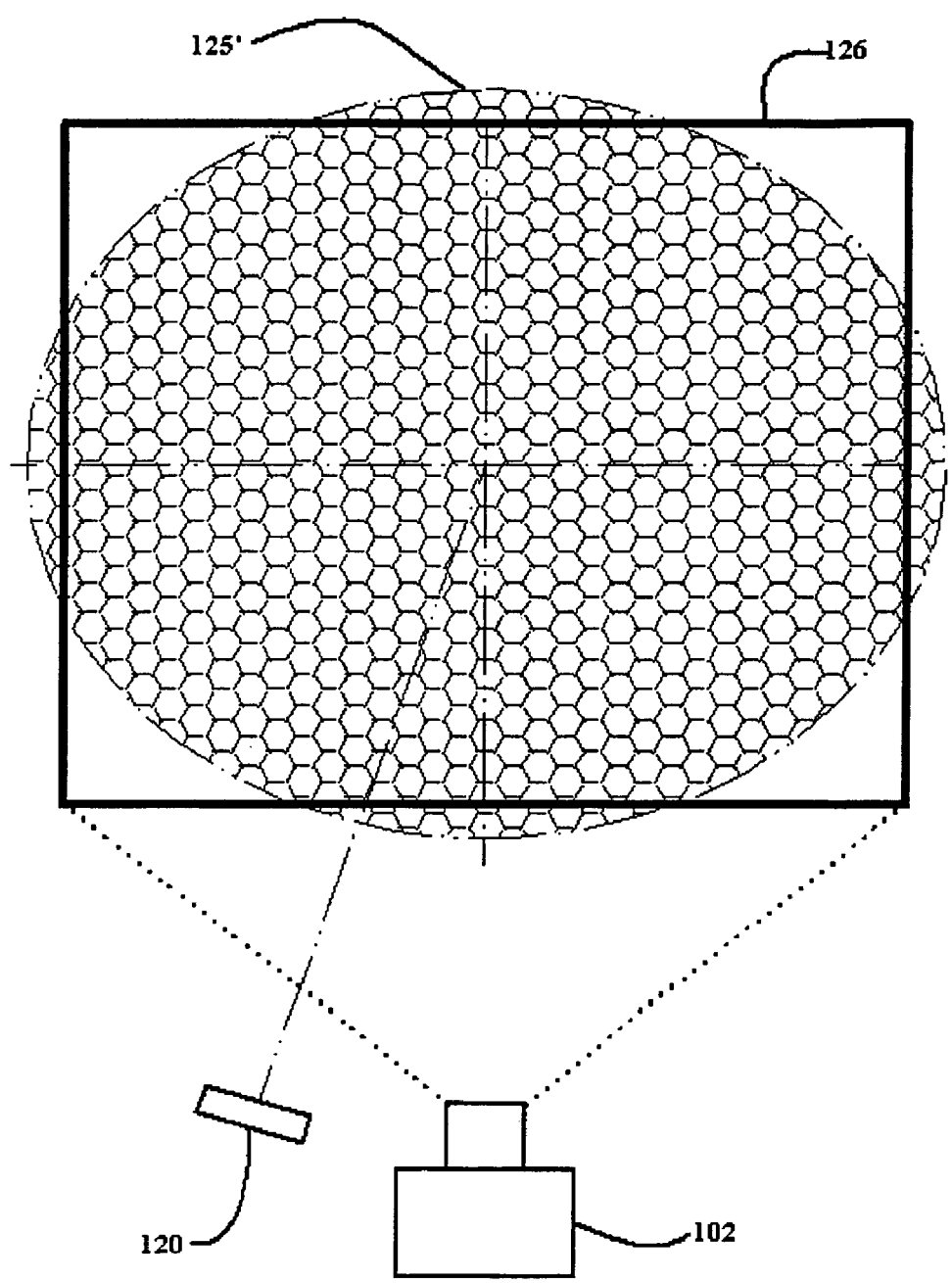
FIG. 8B is a schematic diagram of an alternative imaging arrangement of the apparatus of FIG. 6.

It is likewise to be appreciated that to improve the light distribution to be received by the light receiving apparatus, the number of coherent light sources 100 can be increased from 2 to 8 per light receiving apparatus and that the light source can have an elliptical pattern. For example, FIG. 8A illustrates an imaging arrangement including the camera 102 and a plurality of the elliptical diffusers 120. Coherent light passes through each diffuser 120 and creates a composite illuminated area 125 composed of smaller overlapping elliptical shaped areas. In turn, the camera 102 captures light reflected from the viewed area 126 of the object that is completely illuminated. FIG. 8B illustrates an alternative imaging arrangement including the camera 102 and the elliptical diffuser 120. Coherent light passes through the diffuser 120 and creates an elliptical shaped illuminated area 125 on an object. In turn, the camera 102 "views" or captures light reflected from a viewed area 126.

The elliptical pattern whether it is one or multiples are more conducive to illuminating a rectangular shape which is the output of a camera and the shape of a computer display monitor. The rectangular shape commonly represents an aspect ratio of width to height that in this case is preferably five to four. Additionally another unique feature of this invention is to use the raw rectangular output of the laser to the advantage for an elliptical output. Most laser diodes produce as output a rectangular shaped form of light and then the light is collimated with a lens to form a gaussian mode (TEM$_{oo}$) or round beam. Because a tire quadrant in this case (typical) is 90 deg, the sectional view is wider than tall, and because a camera has an output that is wider than tall and a computer monitor has a display that is wider than tall and a raw laser output is rectangular, the laser is positioned so that the output is wider than tall utilizing the available light energy efficiently. The collimating lens is removed from the laser and replaced with an elliptical light shaping diffuser from Physical Optics Corporation of Torrance, Calif. For this case the output angle of the diffuser is 95 deg. wide and 35 deg. tall but could be any angle/angles that efficiently illuminates the surface area to be tested. FIGS. 6-8 indicate that there are four light sources per light receiving apparatus 102.

As can be seen from FIGS. 6-8, the anomaly detector apparatus or assembly 104 is comprised of a movable support structure 110, which moves up and down, with a pair of plates 112 and 114. Between the plates 112 and 114 are the light generating and the light receiving apparatus, including a plurality of clusters of light sources 100 and light receiving apparatus 102, such as a digital camera. The top plate 114 has four clusters between the top and the bottom plate wherein the clusters are secured in place by bolts 116. The diffuser retainer 120 is held in place by a plurality of screws 122.

Figure 6A:
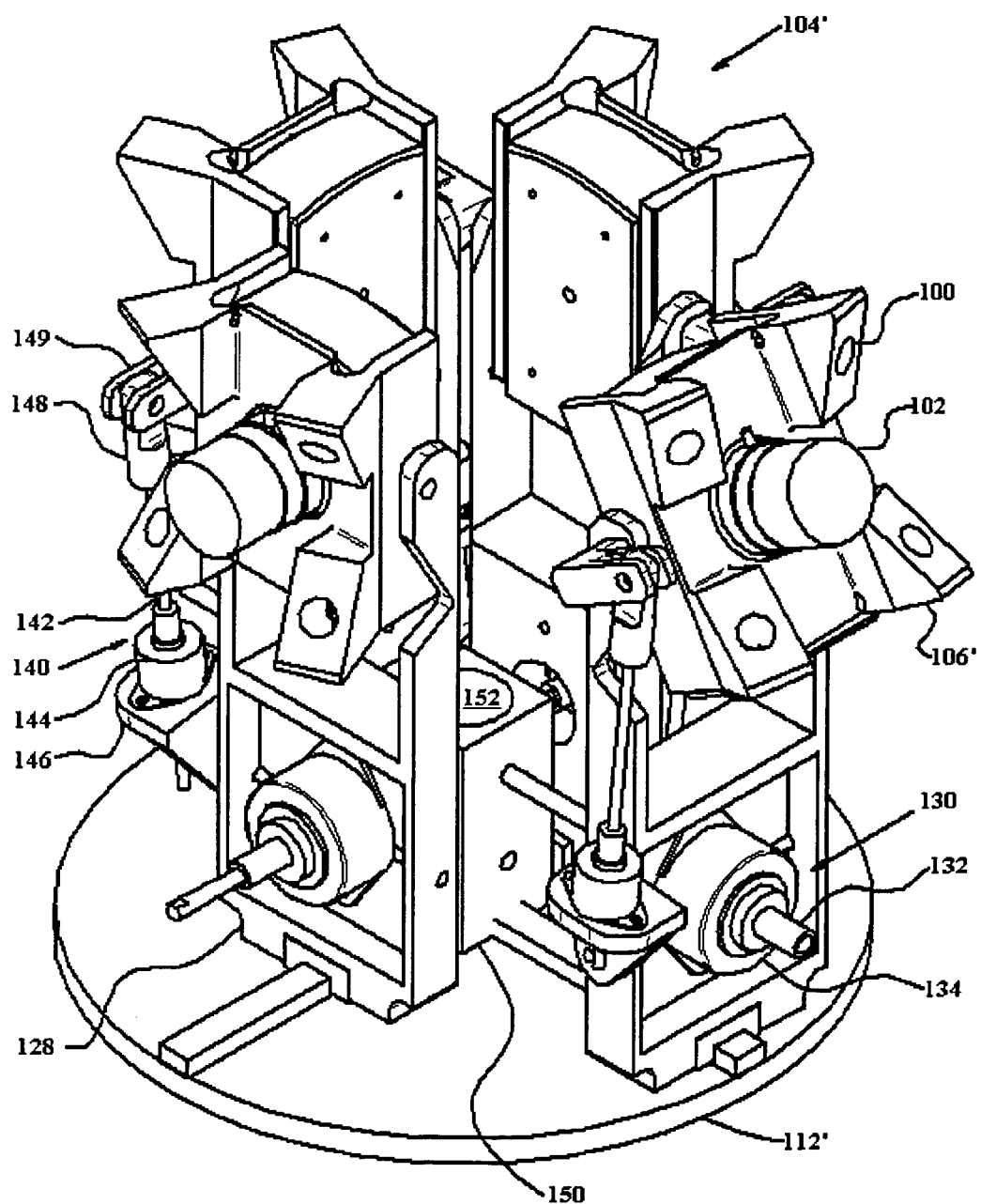
FIG. 6A is a perspective view of a portion of an alternative embodiment of the apparatus of the present invention.

As shown in FIG. 6A, it can also be appreciated that any of the components, i.e. light generating and the light receiving apparatus 100, 102, can be moveable in and out or tip as a group or independently for a better view of the substrate to be tested. Alternatively, the components 100, 102 may be moved in and out or tip as a group or independently in micro motion to increase the ability of each light sensing sensor in the camera to view one or more reflected laser speckles.

FIG. 6A illustrates an alternative anomaly detector apparatus or assembly 104' including a base plate 112' having a plurality of vertically extending and radially or horizontally translatable uprights 128 mounted thereto via a standard guide or slide arrangement as shown. Any suitable pillow block and guide rail combination, or the like, may be used to mount the uprights 128 to the plate 112'. The uprights 128 are preferably translated using an electromechanical linear actuator 130 including a threaded shaft 132 extending through a threaded motor assembly 134. The motor assembly 130 is preferably a Portescap 40 series linear actuator, available from Danaher Motion of West Chester, Pa. A radially inboard end of the shaft 132 is preferably affixed in any suitable manner to a center support 150, which is fixed to the plate 112' in any suitable manner. The center support 150 includes a passage 152 extending vertically therethrough for communicating power and control wires (not shown) for connection to the motor assembly 134. Portions of the motor assembly 134 rotate to translate the upright 128 back and forth in a horizontal or radial direction. Accordingly, the light sources 100, light receiving apparatuses 102, and diffusers 120 are independently translatable.

Retaining members 106' are pivotably mounted to respective upper ends of the uprights 128 to provide the tipping or tilting functionality referred to above. Accordingly, other electromechanical linear actuators 140, including threaded shafts 142 and motor assemblies 144, are mounted to respective sides of the uprights 128 via mounting brackets 146. The motor assembly 130 is preferably a Portescap 20 series linear actuator, available from Danaher Motion of West Chester, Pa. The threaded shafts 142 are coupled to couplers 148, which are coupled to pivot arms 149 that, in turn, are coupled to the pivotable retaining members 106'. Portions of the motor assembly 144 rotate to thread, or linearly displace, the threaded shafts 142 therethrough to move the pivot arms 149 and thereby pivot, tilt, or tip the retaining members 106'. Accordingly, the light sources 100, light receiving apparatuses 102, and diffusers 120 are independently pivotable.

To graphically explain how the animation occurs for the apparatus of FIGS. 6-8, reference can be made to FIGS. 4a and 4b and the associated description above, and/or to FIGS. 29 through 62 and the associated description below.

Software that is utilized to process the speckled image and to display it can be any commercially available image processing software such as PAINT SHOP PRO V. #8.0, supplied by Jasc Software Inc., of Eden Prairie, Minn. Other software that can be used is LabView available from National Instruments of Austin, Tex. or custom written software using an imaging library from the likes of MontiVision of Breiholz, Germany.

FIG. 5 is a representative example of any one of images AA through A_F when the ASTM procedure is utilized except the apparatus of FIGS. 1 and 2 were used in place of an interferometer technique. FIG. 5 shows an image of an ASTM calibration device where the image is a reflected image from the substrate of the calibration device that has been stressed and the laser light has been diffused directly onto the substrate and the reflection of a diffused light is captured as a speckled image by the camera and is stored in the computer memory which in turn can be utilized to generate the output of FIG. 5. It should be noted that the output is characterized as a scaleable representation of the anomaly obtained from the diffused beam of coherent light diffused onto the tire. It should be noted that the image of the reflected light source can be characterized as a scattered speckle reflection. It is to be appreciated that the tire may be in an unstressed and stressed condition or multiple stressed conditions. The computer can compare and display all of the conditions or a portion of them. The invention includes all such comparisons in the completed output form. The output from FIGS. 6-8 can likewise generate the image of FIG. 5.

The utilization of the present technique facilitates quantitative measurement of the anomaly. Alternative to a quantitative determination one can assess the extent of the anomaly by scaling the anomaly with the image that is shown on the computer monitor or is generated in the output such as FIG. 5. Prior art techniques did not permit such measurements or scaling of the anomaly to ascertain the extent of an anomaly in a tire.

The invention described herein in a preferred embodiment does not utilize mirrors for movement of the light. However it is to be appreciated that mirrors may be used to allow the camera to view areas normally inaccessible, depending on the light source, the camera, the diffuser, the test substrate and the number of images to be taken of the substrate. Mirrors may be utilized under particular desired testing techniques and conditions.

The application of the apparatus and method of the present application pertains to a wide variety of substrates that can be stressed, allowing the surface topography to change during stressing. Including but not limited to, any rubber product that has one, or more than one of the following components i.e. reinforcements, backers, strengthening ribs, mounting brackets, cores, honeycombs. These rubber products may be tires (automobile, truck, motorcycle, tractor, construction equipment and aircraft), hoses (radiator, heater, fuel, water, air, hydraulic oil and industrial), belts (fan, power transmission, timing, conveyer such as for mining, and industrial), sheets (pump diaphragms, tank bladders and gaskets), and the like.

A variety of laminated substrates of various plastic materials may be used including thermoplastic, thermoset materials, elastomeric and adhesive materials as well as a wide variety of composites including fiber reinforced composites, metal glass fiber laminates, honeycomb structures, glass or carbon fiber reinforced plastics, and the like. The substrates to be tested include a wide variety of vehicle parts such as for cars, trucks, off-road vehicles, aircraft, farming equipment and the like. One can also detect an anomaly in other substrates, such as, honeycomb aluminum panels and other composite panels as well as carbon fiber reinforced plastic specimens. Other multilayer materials or laminates can be reviewed such as metal ceramic, metal plastic and metal glass fiber compound materials such as those used in the electronic industry, aircraft engine parts or parts in the aeronautics industry.

It is to be appreciated that while the drawings show the interior of a tire, (a cross section of the inside of the outside wall of a toroid), a plurality of any of the substrates can be reviewed by having substrate holders for the substrates. Also the wavelength of the light source which is utilized can vary, such as, visible light (about 400-700 nanometers) to near visible or greater than visible light. The type of diffuser material including the shape and the angle of the output may also vary.

Low Cycle Time NDT System, Method, and Software

Figure 9:
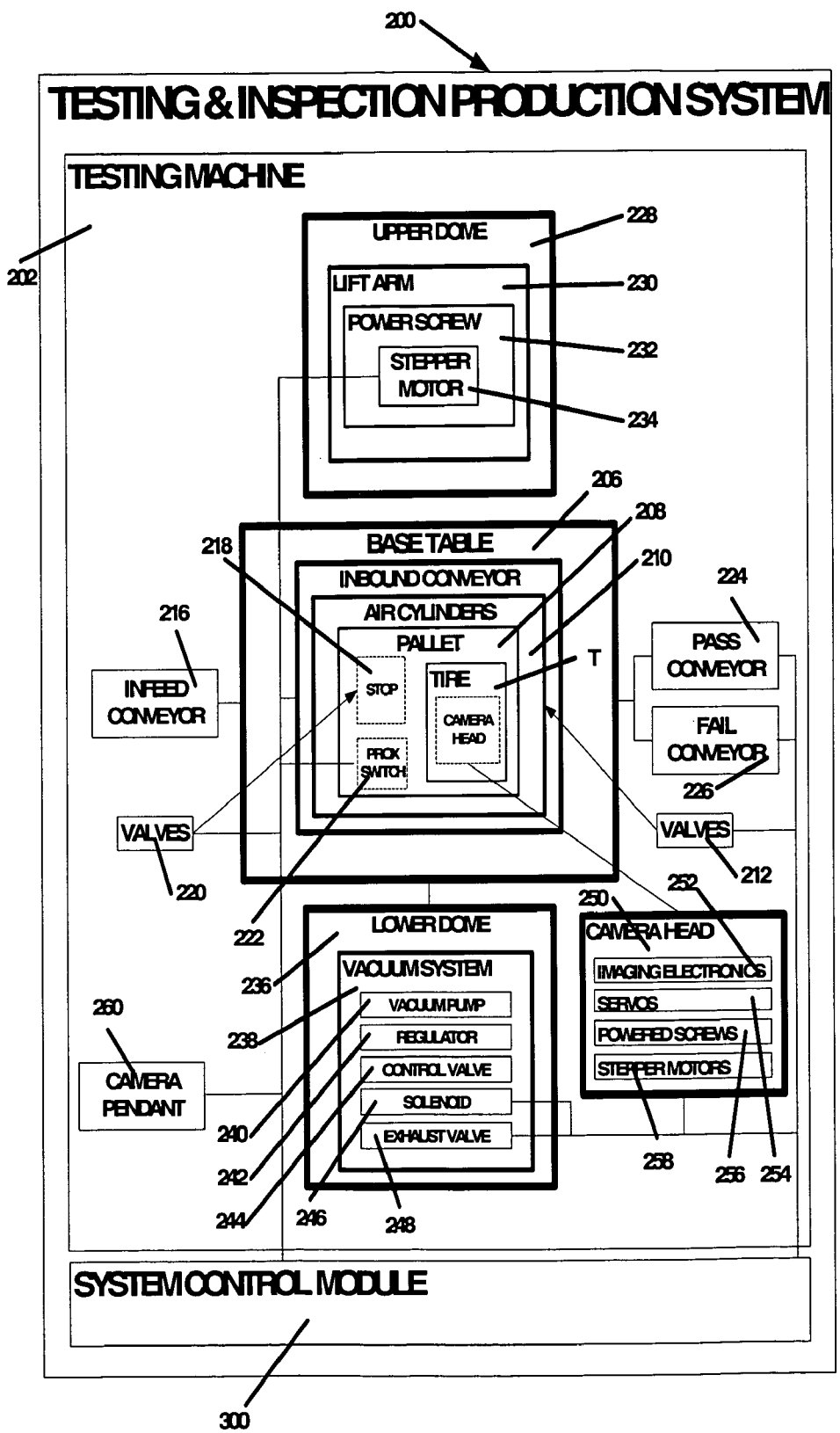
FIG. 9 is a schematic block diagram of a presently preferred embodiment of a production system for non-destructively testing and inspecting a substrate or product.
Figure 69:
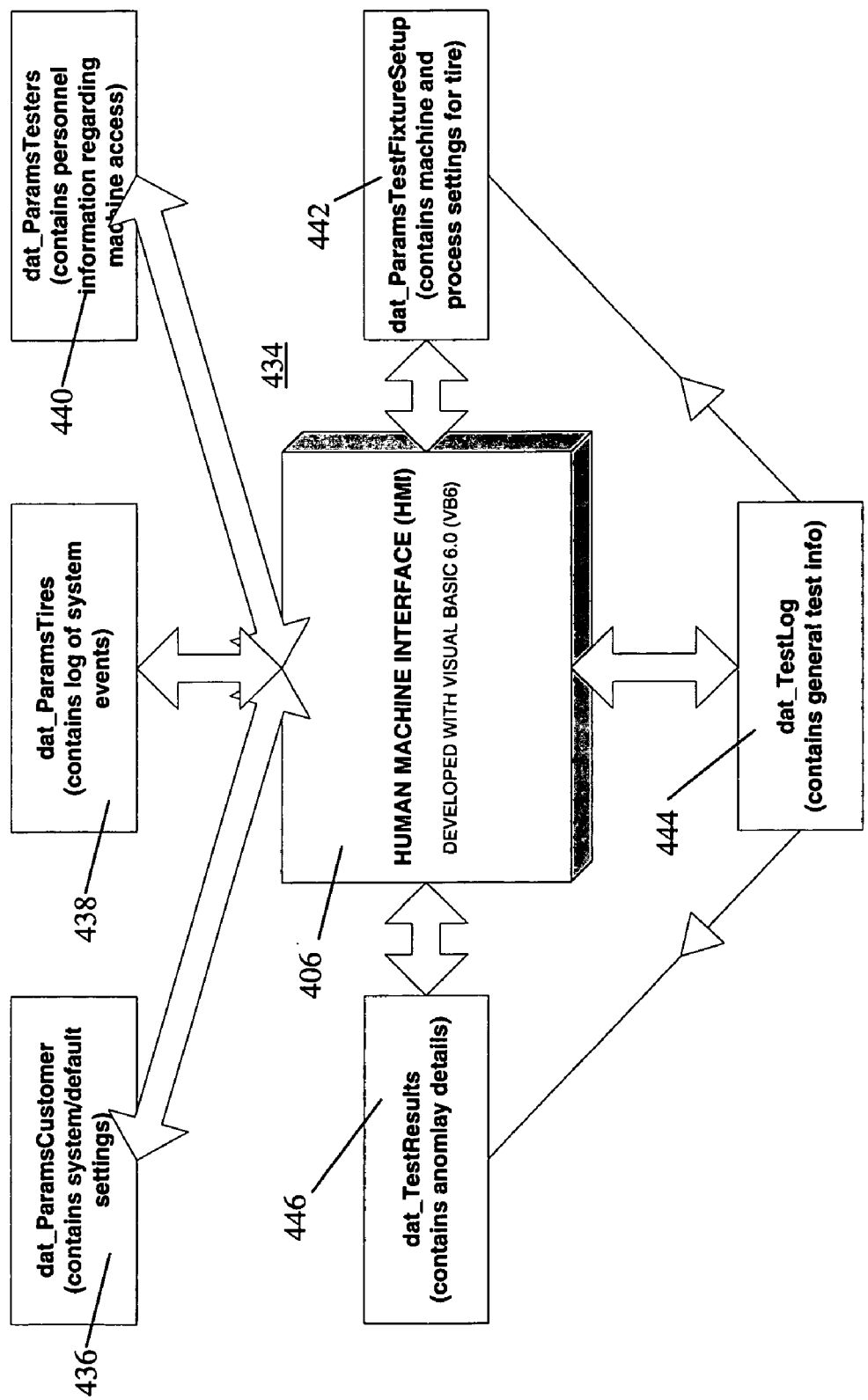
FIG. 69 is a block diagram of a software relationship between different tables of a database with the substrate data collector of FIG. 12.

In general, FIGS. 9 through 69 illustrate other presently preferred embodiments and aspects of a system, method, and software for non-destructively testing and inspecting a substrate or object. Those of ordinary skill in the art will recognize that the term substrate is interchangeable with the terms object, product, article, material, structure, and the like. Many features of these embodiments are similar in many respects to the embodiments described in FIGS. 2 through 8 above, which description is incorporated by reference herein. In any case, the below-described system and method are preferably capable of carrying out the previously described methods of FIGS. 2 through 8 on a substrate or object, such as a tire, for a full 360-degree view within a relatively fast cycle time, such that testing every tire off of a tire production line is more practical than ever before. It is also contemplated that the below-described production system and method could also be adapted to carry out the previously-described method on any desired product, object, or substrate, and is not limited to just use with tires.

System

FIG. 9 illustrates a schematic block diagram of a presently preferred embodiment of a testing and inspection production system 200 including a presently preferred embodiment of a testing machine 202 and related inspection apparatus of the production system 200 that will be described herein below. The machine 202 is preferably coupled to a system control module 300, which will be described in further detail herein below.

The machine 202 generally includes a base table 206 that is supported by any suitable machine framing (not shown) with vibration isolation (not shown) interposed therebetween. The vibration isolation may include four pneumatic leveling boots, wherein three of the boots include associated upstream leveling valves and flow control valves and a fourth boot is in fluid communication downstream of one of the other three valves without any upstream leveling or flow control valves. The base table 206 provides support for a pallet 208, which supports an object such as a tire T. The pallet 208 is preferably raised and lowered by one or more air cylinders 210 controlled by one or more valves 212, which are supplied with shop air as depicted by the arrow and may be controlled by the system control module 300 or by a separate machine control module (not shown) that is in communication with the system control module 300. It is contemplated, however, that all or some of the machine functions could instead or additionally be controlled by the system control module 300, which may be in wireless or hardwired electrical communication with the system control module 300 as shown.

Material handling devices are preferably provided to carry the pallet 208 and tire T. An inbound conveyor 216 conveys the pallet 208 and tire T to a stop 218 that is actuated by a pneumatic valve 220 and that suitably locates the pallet 208 with respect to the table 206 and to a proximity sensor 222 that senses presence (or absence) of the tire T and/or pallet 208. The inbound conveyor 216, stop 218 and valve 220, and proximity sensor 222 are communicated to the system control module 300. An outbound non-anomalous conveyor 224 and an outbound anomalous conveyor 226 are in electrical communication with the system control module 300 and are provided downstream of the table 206 to carry the pallet 208 and tire T off of the table 206.

An air-tight vacuum environment is provided by the following apparatus. An upper dome 228 is lowered into sealing engagement with the top surface of the table 206 by a lift arm 230, which is preferably actuated by a linear displacement device such as a powered screw 232, which is driven by a stepper motor 234 that communicates with the system control module 300. A lost-motion coupling, or decoupler mechanism, is preferably disposed between the upper dome 228 and the lift arm 230 to help prevent the lift arm 230 from inadvertently damaging the upper dome 228 and to enable the upper dome 228 to locate squarely against the top of the table 206 and to eliminate the transmission of vibration between vibration isolated components and non vibration isolated components. A lower dome 236 is maintained in sealing engagement with the bottom surface of the table 206 to complete a sealed environment between the domes 228, 236. A vacuum system 238 is provided in communication with the sealed environment through the lower dome 236. The vacuum system 238 preferably includes an air-driven vacuum pump 240 that is in communication with the lower dome 236 and that receives shop air through a regulator-filter device 242 and a control valve 244, which is driven by a solenoid 246 in communication with the system control module 300. A solenoid-actuated exhaust valve 248 of the vacuum system 238 is in pneumatic communication with the lower dome 236 and in electrical communication with the system control module 300.

Finally, the production system 200 preferably includes an inspection imaging system, which preferably includes an imaging head 250, preferably like that described above with respect to FIGS. 6-8. The imaging head 250 preferably includes electronic imaging devices 252 like cameras and laser light sources, and servos 254 for adjusting the angles, and horizontal and vertical positions of such electronic imaging devices 252. The imaging head 250 is preferably advanced from a position under the table 206 to a position above the table 206 and within the tire T by a suitable powered screw 256 and stepper motor 258. The stepper motor 258 is preferably communicated to the system control module 300 and the imaging devices 252 and servos 254 are preferably communicated to the system control module 204. A camera position control pendant 260 is also provided in communication with the servos 254 of the imaging head 250 for manually controlling positioning of the imaging devices 252.

Controls

Figure 10:
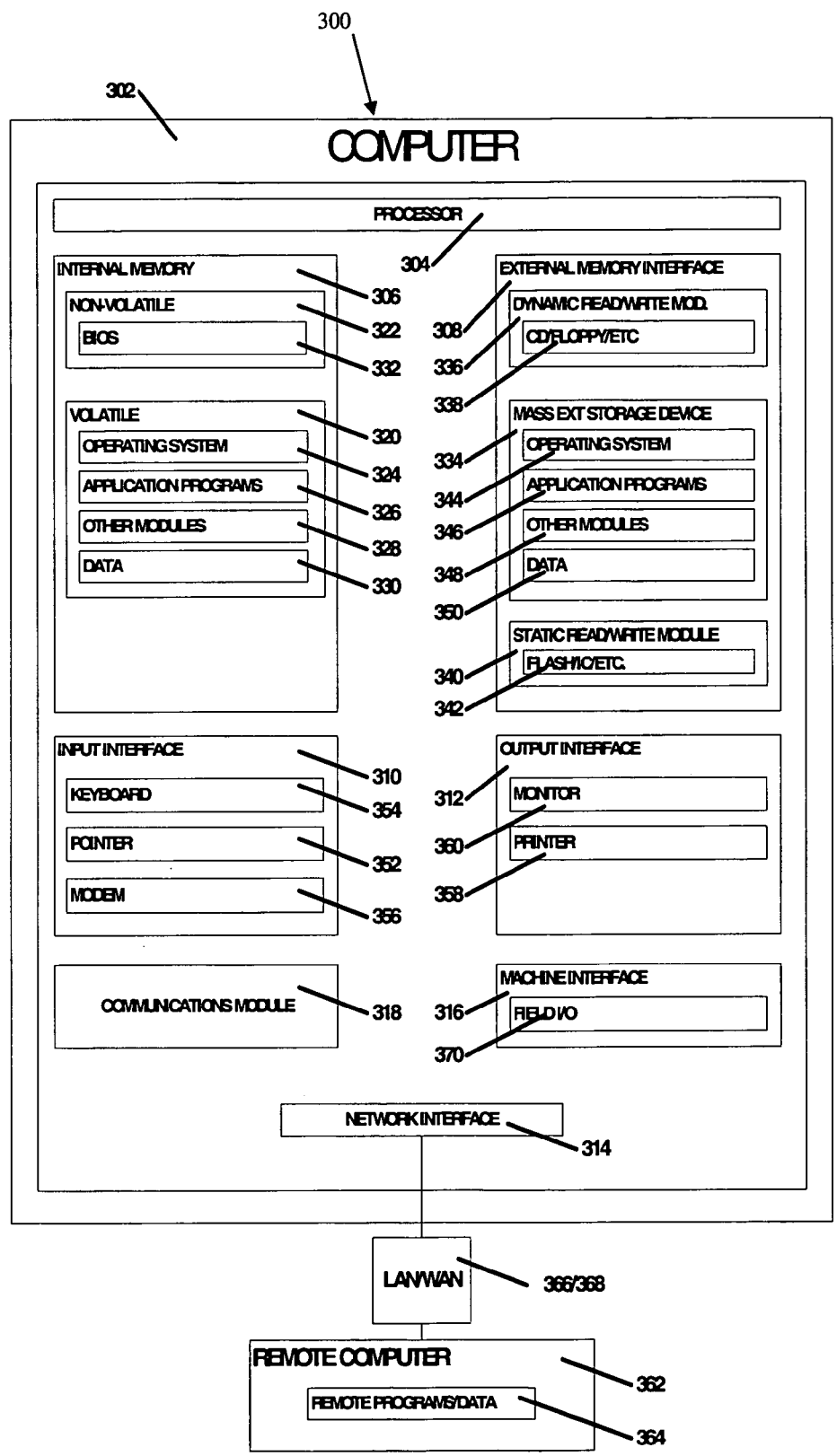
FIG. 10 is schematic block diagram of a presently preferred embodiment of a control module and related apparatus of the production system of FIG. 9.

FIG. 10 shows one example of the system control module 300 including a data processing system or computer 302 and related apparatus to implement method or apparatus aspects of the present disclosure. The computer is preferably a personal computer (PC), for example, a DELL 470 desktop workstation.

But for purposes of this disclosure, the system control module 300 may include any instrumentality or aggregation of instrumentalities operable to compute, classify, detect, display, handle, originate, manipulate, manifest, process, record, reproduce, receive, retrieve, switch, store, or utilize any form of data, information, intelligence for academic, business, production, scientific, or other purposes. Although described in connection with an exemplary computing system environment, including a computer, the production system and method are operational with numerous other general purpose or special purpose computing system environments or configurations. The computing system environment is not intended to suggest any limitation as to the scope of use or functionality of the production system or method. Moreover, the computing system environment should not be interpreted as having any dependency or requirement relating to any one component, or combination of components, illustrated in the exemplary operating environment. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, personal digital assistants, mobile telephones, network PCs, minicomputers, mainframe computers, distributed computing environments that include any of the above systems or devices, and the like.

The computer 302 is responsible for at least some, if not all, control of the testing machine 202 of FIG. 9. For example, the computer 302 is responsible for receiving imaging input, carrying out image processing and data analysis and management, and transmitting imaging output. To facilitate such functionality, the computer 302 has a processor 304, an internal memory 306, an external memory interface 308, an input device interface 310, an output device interface 312, a network interface 314, a machine input/output interface 316, and a communications module 318.

The communications module 318 may be any type of suitable module including a system bus, which couples the various above-described system components or modules. The system bus 318 may provide for data transmission internally between each of the elements in the computer 302 and externally between the internal elements of the computer 302 and any other elements external of the computer 302. The system bus 318 represents one or more of any of several types of bus structures, including a memory bus or memory controller, a peripheral bus, an accelerated graphics port, a processor or local bus using any of a variety of bus architectures, and the like. By way of example, and not limitation, such bus architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus also known as Mezzanine bus, and the like.

The processor 304 may be configured to provide control logic that provides the functionality for the production system. In this respect, the processor 304 may encompass one or more processing units, controllers, microprocessors, microcontrollers, application specific integrated circuits (ASIC), complex programmable logic devices (CPLD), field programmable gate arrays (FPGA), any combinations of the aforementioned, and the like. The processor 304 may be interfaced with the internal memory 306, which is a medium configured to provide at least temporary storage of data and/or computer software or computer-readable instructions that provide at least some of the functionality of the production system and that may be executed by the processor 304. As used herein, the term processor also includes any ancillary devices such as clocks, power supplies, and the like.

The internal memory 306 includes computer readable storage or media in the form of removable and/or non-removable, volatile memory 320 and/or non-volatile memory 322. Exemplary volatile memory 320 may include random access memory (RAM), static RAM (SRAM), dynamic RAM (DRAM), and the like, for running software and data on the processor 304. RAM typically contains data and/or program modules that are immediately accessible to and/or presently being operated on by the processor 304. By way of example, and not limitation, the volatile memory 320 may include an operating system 324, application programs 326, other memory modules 328, and data 330.

Exemplary non-volatile memory 322 may include read only memory (ROM), erasable programmable ROM (EPROM), electrically erasable programmable ROM (EEPROM), dynamic read/write memory like magnetic or optical disks or tapes, and static read/write memory like flash memory, for storing software and data. A basic input/output system (BIOS) 332 is typically stored in ROM for containing basic routines that help to transfer information between elements within the computer 302, such as during computer boot-up.

The computer 302 may also include other removable/non-removable volatile/non-volatile data storage or media. For example, a mass external storage read/write device/module 334 is shown in the exemplary form of a dynamic read/write hard disk drive that reads from or writes to non-removable, non-volatile magnetic media. Also, a dynamic read/write device/module 336 such as a magnetic or optical drive that reads from and writes to a removable, non-volatile device 338, such as a magnetic floppy disk, magnetic tape cassette, digital versatile disk, digital video tape, optical disk like a CD-ROM, or other optical media. Moreover, a static read/write module 340 may be used in the exemplary operating environment for use with a static read/write device 342 including, but not limited to, a flash memory card, integrated circuit chip, and the like.

The memory media/modules discussed above enable storage and communication of computer readable instructions, data structures, program modules, and other data for the computer 302. For example, the mass storage device 334 is illustrated as storing an operating system 344, application programs 346, other program modules 348, and program data 350. Note that these components may either be the same as or different from the operating system 324, application programs 326, other program modules 328, and data 330 of the internal memory 306. The operating system 344, application programs 346, other program modules 348, and data 350 are illustrated as discrete blocks and given different numbers here to illustrate that, at a minimum, they are different copies. It is recognized, however, that such programs and components reside at various times in different storage media associated with the computer 302, and are preferably executed by the processor 304 of the computer 302. Computer programs may be installed or loaded into a secondary memory of a computer such as the mass storage device 334, dynamic storage device 336, or static storage device 338. Upon execution by the processor 304, such computer programs may be loaded at least partially into a primary memory such as the internal memory 306. Any suitable non-volatile memory interface 308 may be used to connect the mass storage device 334 and other memory modules 336, 340 to the system bus 318.

User interface selection devices, or input peripheral devices, such as a pointing device 352 (e.g., a mouse, trackball, pen, touch pad, or the like), keyboard 354, modem 356, and the like, may be used to enter commands and information into the computer 302. Although expediently shown within the computer block, those of ordinary skill in the art will recognize that the peripheral devices are actually external device with respect to the computer. Other input devices (not shown) may include a microphone, joystick, satellite dish, wireless communication device, scanner, or the like. The input interface 310 preferably connects the above described input devices, and possibly other input devices, to the processor 304 preferably via the system bus 318, but may be connected by other interfaces and bus structures, such as a parallel port, Universal Serial Bus (USB), infrared device, or the like.

Output peripheral devices such as a printer 358, a monitor 360, or other type of display device or other peripheral device such as speakers (not shown), and the like, are also connected to the system bus 318 via the output interface 312, which may be any suitable printer, video, etc., type of interface. The monitor 360 is preferably a touchscreen display available from Xycom Automation of Saline, Mich. Although expediently shown within the computer block, those of ordinary skill in the art will recognize that the peripheral devices are actually external device with respect to the computer.

As used herein, the term interface broadly means any suitable form of electronic device or adapter, or even a software module or adapter, which enables one piece of equipment to communicate with or control another. Any of the interfaces disclosed herein may conform to any suitable protocols such as ethernet or field buses such as Profibus, Interbus, Devicenet, RS-232, parallel, small computer system interface, USB, wireless protocols such as Bluetooth, infrared, and the like, and any other suitable input/output (I/O) protocols. Moreover, an interface in the context of a software architecture includes a software module, component, code portion, or other sequence of computer-executable instructions. Such an interface includes, for example, a first module accessing a second module to perform computing tasks on behalf of the first module. The first and second modules include, in one example, application programming interfaces (APIs) such as provided by operating systems, component object model (COM) interfaces (e.g., for peer-to-peer application communication), and extensible markup language metadata interchange format (XMI) interfaces (e.g., for communication between web services). The interfaces may be tightly coupled, synchronous implementations such as in Java 2 Platform Enterprise Edition (J2EE), COM, or distributed COM (DCOM) examples. Alternatively, or in addition, the interfaces may be loosely coupled, asynchronous implementations such as in a web service (e.g., using the simple object access protocol). In general, the interfaces may include any combination of the following characteristics: tightly coupled, loosely coupled, synchronous, asynchronous, and the like. Further, the interfaces may conform to a standard protocol, a proprietary protocol, or any combination of standard and proprietary protocols. The interfaces described herein may all be part of a single interface or may be implemented as separate interfaces or any combination therein. The interfaces may execute locally or remotely to provide functionality. Further, the interfaces may include additional or less functionality than illustrated or described herein.

The computer 302 may operate in a networked environment, in communication with one or more remote computers 362. The remote computer 362 may be a personal computer, a server, a router, a network PC, a peer device, other common network node, and the like, and typically includes its own versions of many or all of the internal and external or peripheral elements described above relative to the computer 302. In a networked environment, software modules and/or data used by the computer 302, or portions thereof, may be stored in the remote computer 362 or a remote memory storage device (not shown) associated therewith or connected thereto. By way of example, and not limitation, FIG. 10 illustrates remote application programs/data 364 as residing in memory of the remote computer 362.

The network logical connections or communications depicted in FIG. 10 include a local area network (LAN) 366 and a wide area network (WAN) 368, but may also include any other suitable networks and connections. The LAN 366 and/or WAN 368 may be a wired network, a wireless network, a combination thereof, and the like. Such networking environments are commonplace in offices, enterprise-wide computer networks, intranets, and global computer networks (e.g., the Internet or World Wide Web). When used in a local area networking environment, the computer 302 is preferably connected to the LAN 366 through the network adapter or interface 314. When used in a wide area networking environment, the computer preferably includes the modem 356 or any other means for establishing communications over the WAN 368. The modem 356, which may be internal or external, is preferably connected to the system bus 318 via the input interface 310, or other appropriate arrangement. The network connections shown are exemplary and other means of establishing a communications link between the computers 302, 362 may be used.

Figure 11:
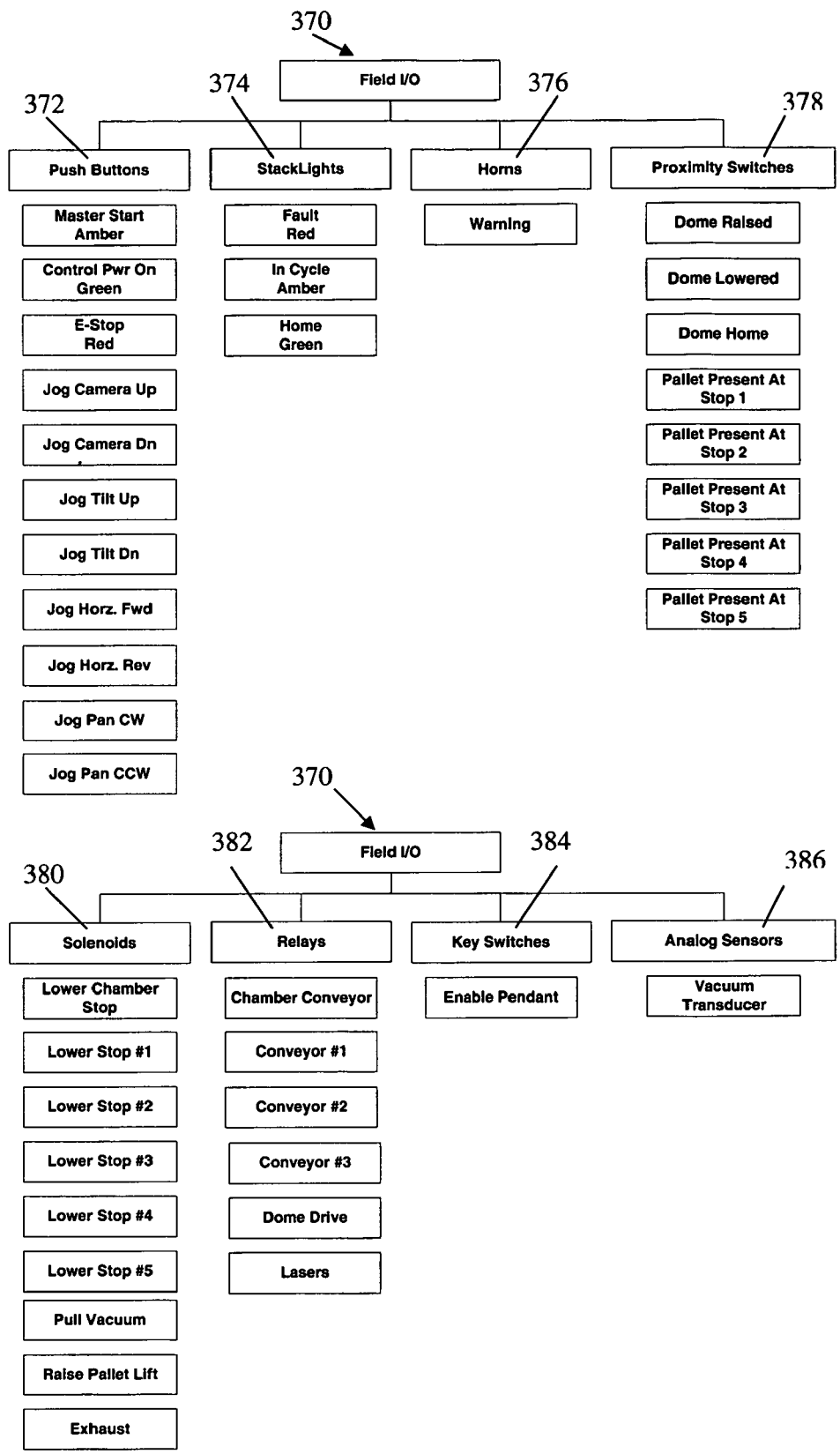
FIG. 11 is an organizational block diagram of a presently preferred embodiment of field inputs and outputs of a production machine of the production system of FIG. 9.

Finally, a plurality of different field input and outputs (field I/O) 370 of the test machine 202 are shown connected to the processor 304 via the system bus 318 and machine I/O interface 316. An exemplary and preferred field I/O 370 is more specifically illustrated in the organizational block diagram of FIG. 11. The field I/O's are in hardwired or wireless electrical communication with at least the following various machine elements: push buttons 372, stack lights 374, horns 376, proximity switches 378, solenoids 380, relays 382, key switches 384, analog sensors 386, and the like. Specific examples of such elements are shown in the Figure.

In operation, and referring again to FIG. 10, the processor 304 is powered by a power supply (not shown) and initially operates on instructions stored in internal memory 306. The processor 304 receives commands or data from a user through input devices, and receives, processes, and stores data or instructions from various storage media including the internal memory 306 and through the memory interface 308, and outputs data or instructions to output peripheral devices. Generally, data processors of computers are programmed to carry out computer-executable instructions, such as those associated with or embedded in software or computer programs such as operating systems, application programs, and the like.

Computer programs may include, but are not limited to routines, modules, objects, components, data structures, and the like, for performing particular tasks and/or implementing particular abstract data types. Computer programs may exist in a variety of forms both active and inactive. General examples include software programs comprised of instructions in source code, object code, executable code or other formats; firmware programs; or hardware description language (HDL) files; and the like. Specific examples include assembler, C, C++ objects, Visual Basic, Visual C++, XML, Java, and Microsoft® Foundation Classes, and the like.

As mentioned previously, the computer 302 is adapted to use at least some form of computer readable media, which may include volatile and/or non-volatile media, removable and/or non-removable media, and which may be any suitable medium that may be accessed by a computer. By way of example and not limitation, computer readable media include computer storage media, communication media, and any combination thereof. The system and methods described herein may include these and other various types of computer-readable media wherein such media may contain, store, and/or carry instructions or programs for implementing some or all of the method steps described below in conjunction with the processor 304 or other data processor. At least some portion of the testing and inspection methods may be practiced locally or in a distributed computing environment where tasks may be performed by remote computers or processing devices that are linked through a communications network, such as the LAN 366, WAN 368, or the like. In a distributed computing environment, program modules may be located in both local and remote computer storage media including memory storage devices.

Computer storage media may be used to distribute computer programs locally and may include volatile and non-volatile, removable and non-removable media implemented in any method or technology for storage of information such as computer readable instructions, program modules, data structures, other data, and the like. More specifically, computer storage media may include RAM, ROM, EEPROM, flash memory or memory sticks, integrated circuits, CD-ROM, digital versatile disks (DVD) or other optical disk storage, magnetic cassettes, magnetic tape, magnetic disk storage or other magnetic storage devices, or any other medium that may be used to store the desired information and that may be accessed by a computer.

Communication media preferably embody computer readable instructions, program modules, data structures, other data, and the like, in a compressed or uncompressed data signal such as a carrier wave or other transport means, and include any information delivery media. Those skilled in the art are familiar with modulated data signals, which have one or more characteristics set or changed in such a manner as to encode information in the signals. In any event, exemplary computer readable signals, whether modulated using a carrier or not, are signals that a computer system hosting or running a computer program can be configured to access, including signals downloaded using the Internet or other networks. Wired media such as a wired network or direct-wired connection, and wireless media such as acoustic, RF, infrared, and other wireless media, are examples of communication media. In a sense, the Internet itself, as an abstract entity, is a computer readable medium and the same is true of computer networks in general. It is therefore to be understood that the testing and inspection methods may be performed by any computing devices suitable for executing one or more of the specified functions, using any media and being located anywhere.

System Software Architecture

Figure 12:
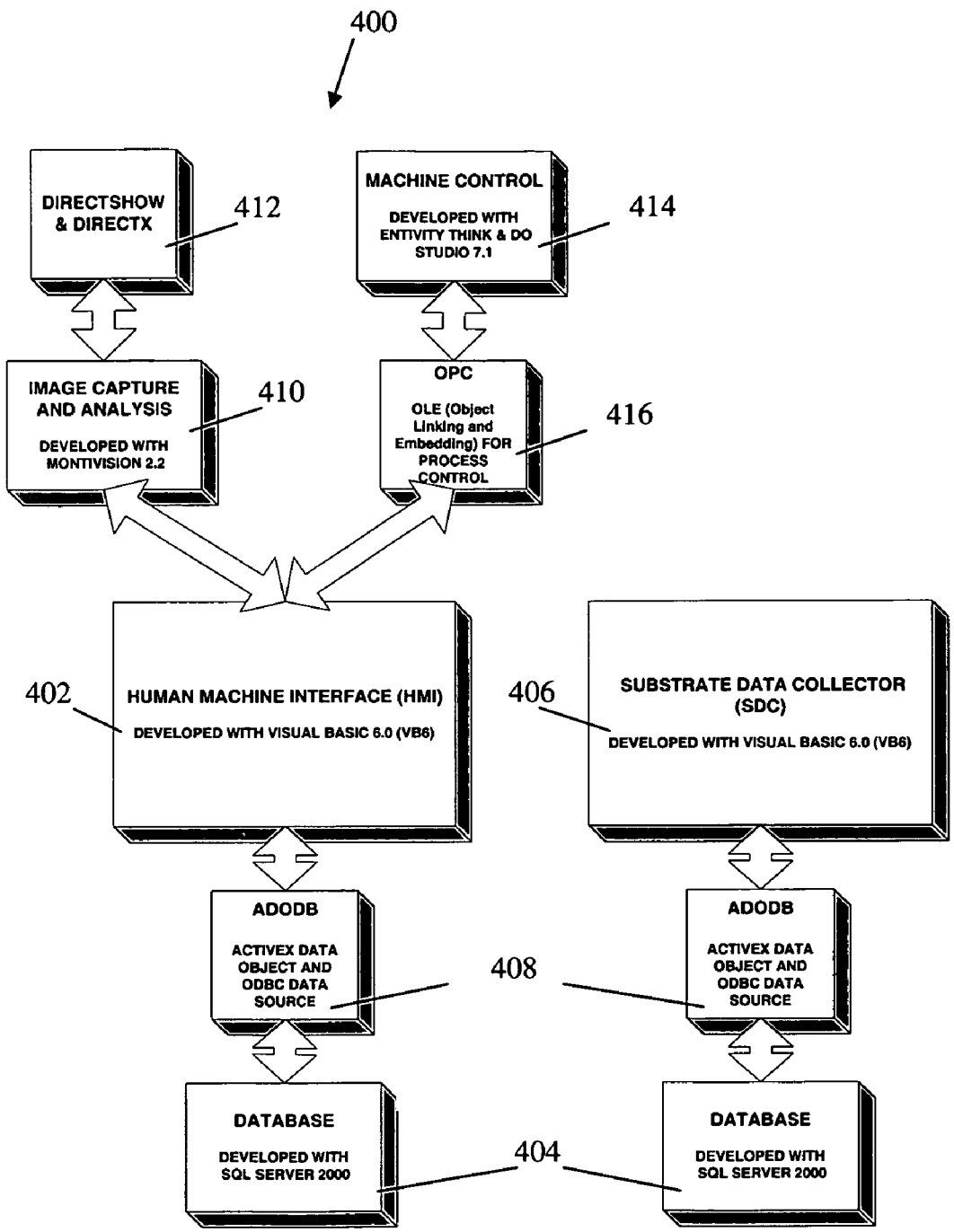
FIG. 12 is a software block diagram of a presently preferred embodiment of a software architecture of a differencing video system and substrate data collector used with the production system of FIG. 9.

FIG. 12 illustrates a block diagram of a differencing video system (DVS) software architecture 400, which is suitable for storage on one or more of the non-volatile memory media 334, 336, 340 associated with the computer 302 of FIG. 10 and for at least partial temporary storage on the volatile memory 320 of the internal memory 306 of the computer 302. It is also contemplated that any portion of the software architecture 400, or other data or databases, could be stored on any remote computer 362 and/or media and distributed over any suitable network. The software architecture 400 includes a DVS human machine interface (HMI) 402, which may be developed with Visual Basic® 6.0 as a central graphical user interface (GUI) for the computer 302.

One or more databases 404 are provided for storing data automatically collected, manually input, or by any combination thereof. The database(s) 404 communicates with one or both of the HMI 402 and a substrate data collector program (SDC) 406. The SDC 406 may also be developed using Visual Basic® 6.0 and will be described in further detail below with reference to FIGS. 64 through 69. The database(s) 404 is preferably developed with Microsoft® SQL Server 2000, but may be developed with any other known and suitable database programs such as dBase®, Microsoft® Access®, and the like. The database(s) 404 and HMI 402 and/or SDC 406 are interfaced with any suitable interface module or program 408 such as an Active Data Objects Data Base (ADOdb), which is a widely known freely available product to those of ordinary skill in the art. The database(s) 404 will be described in further detail below with respect to FIG. 63.

Also, the HMI 402 communicates with a suitable image capture and analysis program 410 such as one developed using MontiVision Development Kit 2.2, or any other suitable image processing software. The image processing program 410 cooperates with any suitable application program interfaces (API) 412, such as Microsoft® DirectX® and Direct-Show® to enable flexible program access to hardware such as digital cameras. DirectX® is a collection of multimedia application programming interfaces (APIs), and provides a standard development platform that enables access to specialized hardware features without having to write hardware-specific code. DirectX® also enables multimedia applications to take advantage of hardware acceleration features supported by graphics accelerators. Microsoft® Direct-Show® is one of the DirectX® technology components and is an architecture for streaming media on the Microsoft® Windows® platform. DirectShow® provides for high-quality capture and playback of multimedia streams and supports a wide variety of imaging formats, including Advanced Systems Format (ASF), Motion Picture Experts Group (MPEG), Audio-Video Interleaved (AVI), MPEG Audio Layer-3 (MP3), and WAV sound files. DirectShow® supports capture from digital and analog devices based on the Windows® Driver Model (WDM) or Video for Windows® and is integrated with other DirectX® technologies to automatically detect and use video and audio acceleration hardware when available, but is also capable of supporting systems without acceleration hardware. DirectShow® is preferably deployed to simplify media playback, media format conversion, and image capture tasks, and provides access to underlying imaging stream control architecture for custom applications.

Moreover, the HMI 402 also communicates with a machine control program 414, which is preferably loaded to the computer 302. In any case, the machine control program 414 is preferably developed using any suitable machine automation and control software such as Entivity Think & Do® Studio 7.1. The HMI 402 and machine control program 414 are interfaced with any suitable hardware driver 416 such as an object linking and embedding (OLE) for process control (OPC) programs, which are readily available from Rockwell Automation, and National Instruments, among others.

Machine Control

Figure 13A:
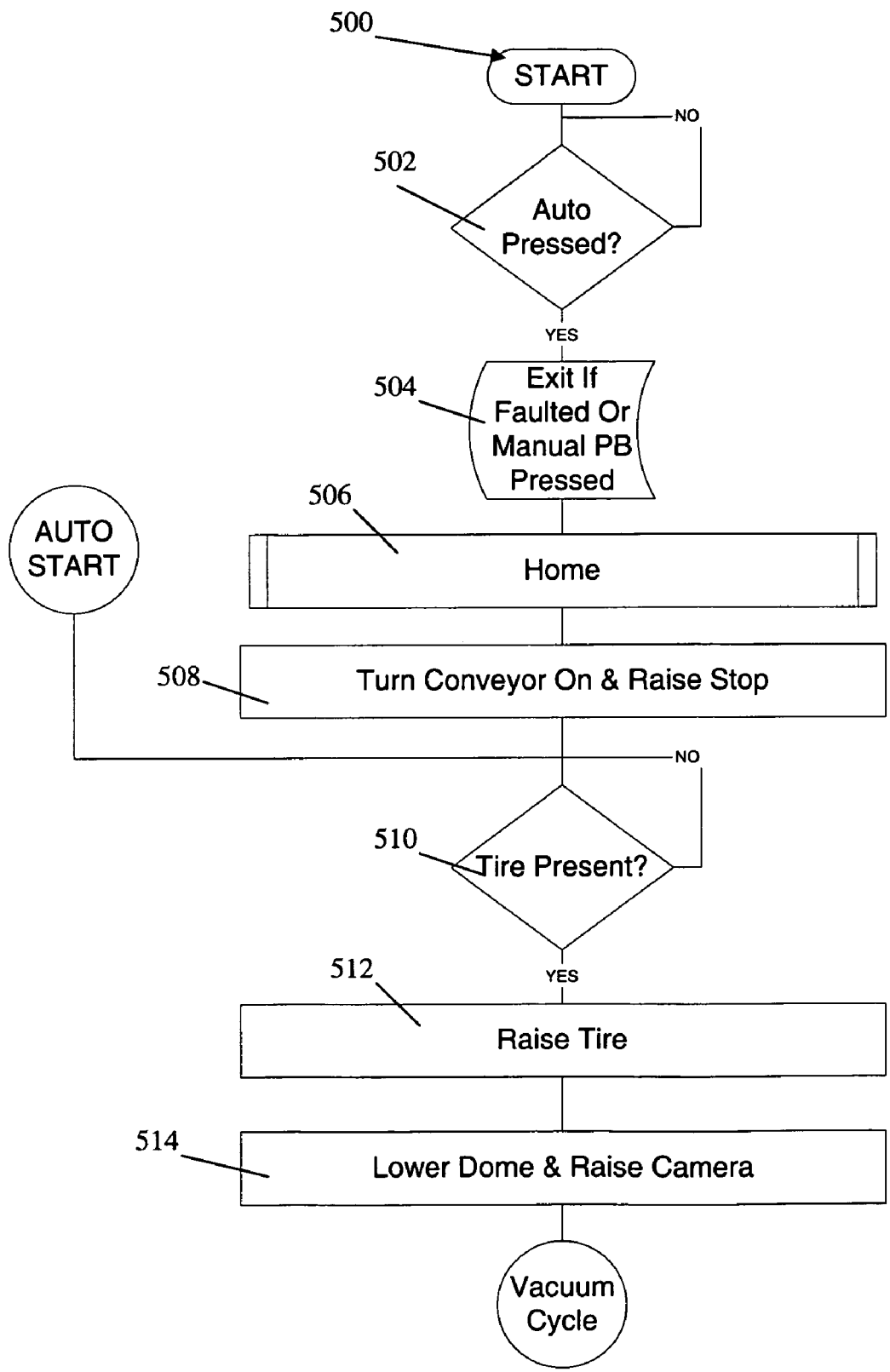
FIGS. 13A through 13C represent a flow chart of a presently preferred embodiment of a method of operating the production system of FIG. 9.
Figure 13B:
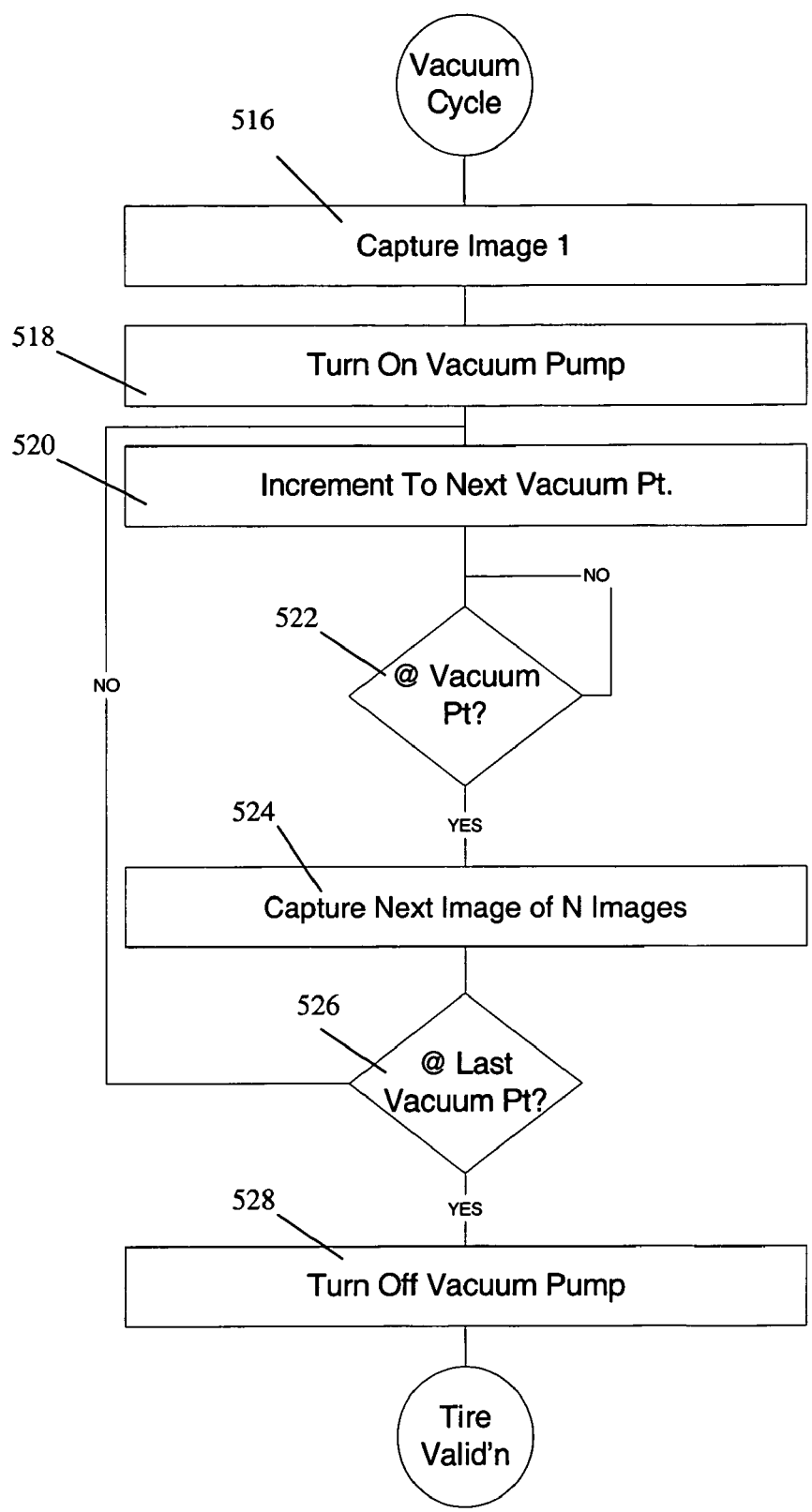
Figure 13C:
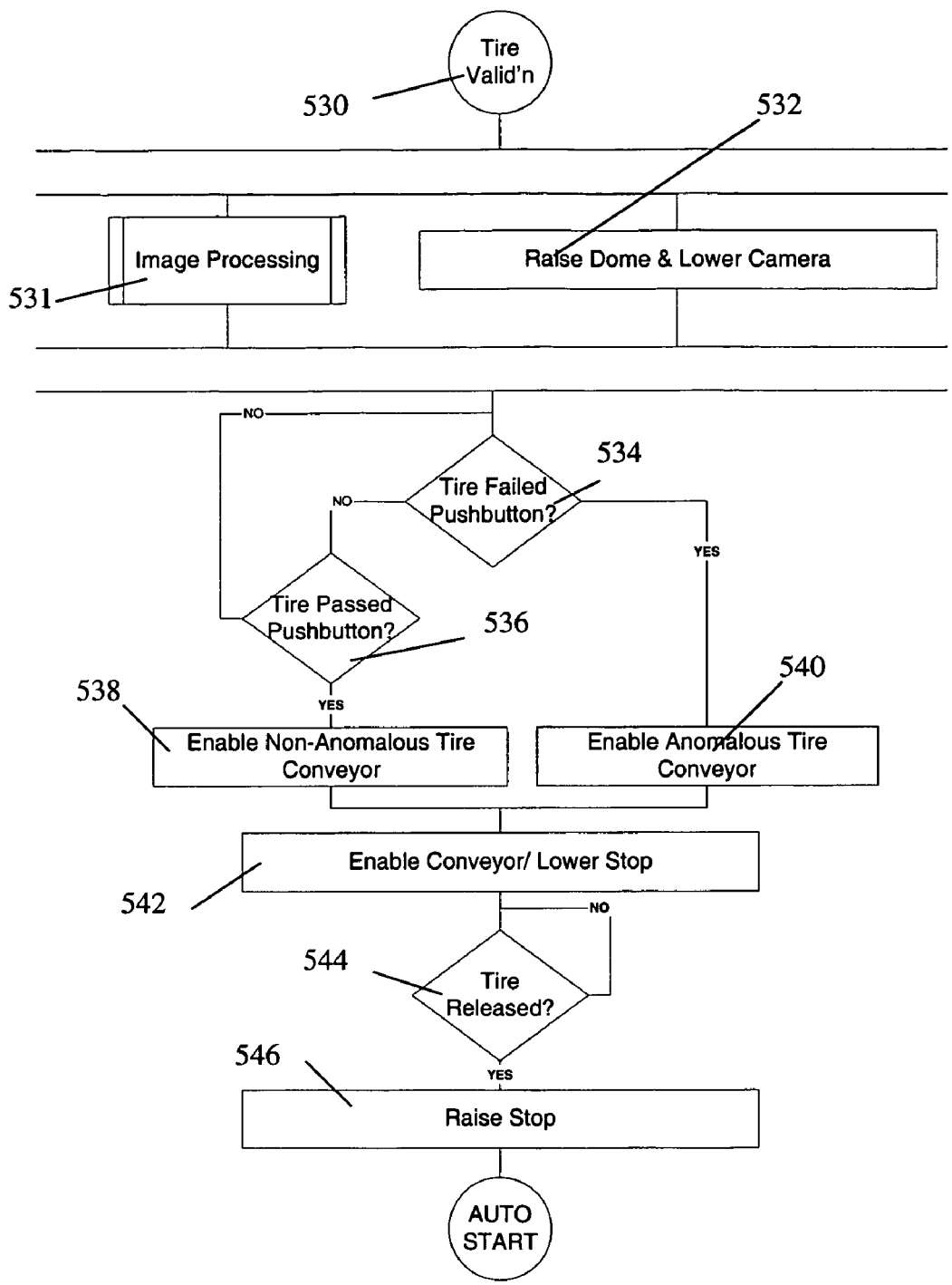

FIGS. 13A through 13C illustrate a preferred automatic or auto-cycle machine control routine 500 that may be carried out at least in part using the control system of FIG. 10 described above and using the machine control 414 software of FIG. 12. In describing the routine, reference will be made to the control system of FIG. 10 and to the production system of FIG. 9.

Initially, at step 502, it is determined if an auto button or menu item is pushed or selected. The auto button may be a separate machine hardware push button, a touchscreen pick, or the like. If auto is not selected, then the routine loops to a point prior to step 502. But if auto is selected, then the routine proceeds to step 504.

At step 504, the routine exits if a machine fault is detected or if a manual push button such as an emergency stop has been pressed. Otherwise, the routine proceeds to step 506. Step 504 represents an exception block wherein the condition is checked continuously and independently of the logic flow.

At step 506, the routine calls a predefined machine homing sub-routine. Such a homing subroutine is standard and known to those of ordinary skill in the art, and basically commands movable machine sub-systems such as the dome lift device(s), pallet lift device(s), and camera lift device(s), to travel toward a known home position.

At step 508, the incoming conveyor 216 is activated and the pallet stop 218 lifted, so that the tire T and pallet 208 are loaded onto the machine table 206 in a predetermined location.

At step 510, it is determined whether the tire is present and ready to be tested and inspected, by way of communication with the proximity sensor 222. If the proximity sensor 222 does not detect the tire T, then the routine loops back to a position between Steps 508 and 510 to re-check if there is a tire present. Otherwise, the routine proceeds to step 512. The Auto Start bubble represents the beginning of the next auto cycle after the routine finishes the current cycle and remains in auto.

At step 512, the pallet 208 and tire T are raised by sending a command to open the air valve 212 and thereby actuate the air cylinder(s) 210. Thereafter, or substantially simultaneously, at step 514, the upper dome 228 is lowered and the imaging head 250 raised by sending commands to the appropriate stepper motors 234, 258. When the pallet 208 and tire T, upper dome 228, and imaging head 250 are in position, such as by being sensed by limit switches (not shown), the routine proceeds to a tire testing and inspection sequence beginning at step 516 of FIG. 13B.

In the tire testing and inspection sequence, several successive images of the object are preferably captured and stored individually during a testing cycle between a predetermined baseline vacuum test level and a first predetermined vacuum test level. These images are preferably processed with the computer 302 and the results are preferably displayed on the computer monitor 360 in real time. Any desired number (N) of images are captured and stored as image 1, image 2, etc., through image N. Preferably six images are taken and stored as image 1 through image 6, but any other suitable quantity of images may also be taken and stored, such as four images taken and stored as image 1 through image 4.

In capturing a digital image, an imaging device such as a CCD is first reset. Any other suitable imaging devices, such as a complementary metal oxide semiconductor (CMOS), may also be used. Then a mechanical and/or electrical shutter of the imaging device is "opened" to expose the CCD to light reflected from the tire to build up electrical charges in the CCD, until the shutter closes. The CCD is basically an array of tiny light-sensitive diodes or photosites, which convert light or photons into electrical charges or electrons that correspond to image pixels. A CMOS device is similar, but includes an array of several tiny transistors or photosites that correspond to image pixels. The CMOS approach is more flexible than the CCD approach because each CMOS pixel can be read individually. In either case, each photosite is sensitive to light, wherein the brighter the light that hits any given photosite, the greater the electrical charge that will accumulate at that site. An analog to digital converter measures the electrical charge and creates a digital signal that represents the values of the charge at each pixel. The processor interpolates the data from the pixels to create a color or grayscale digital image. The processor may also perform a predetermined level of compression on the data for more efficient storage. In any event, the processor may also direct or store the digital image to a memory as an image data file.

Moreover, digital live video is defined herein as a succession of digital images. Accordingly, as used herein the term "image" broadly encompasses a still or live video visual image, a printed visual image, a data file like a bitmap or the like that represents a still or live video image, or a scan of a printed image, and the like. More specifically, the terminology "digital image" broadly encompasses a still or live video visual image and a data file representing an image. Finally, the term anomaly may refer to an actual, physical anomaly in an object, and to a digital representation (such as a "blob") of that anomaly such as in a digital image.

Referring to FIG. 13B, at step 516 with the pallet 208 and tire T, upper dome 228, and imaging head 250 in position, a first or baseline image is captured by the imaging equipment. The predetermined baseline vacuum test level may be a zero value vacuum test level or may be a non-zero value vacuum test level. As discussed previously, coherent light is directed onto the tire T by the light sources of the imaging head 250. Coherent light is not received by the cameras directly from the light sources, only indirectly as reflected off of the tire T. It is contemplated that some ambient flooding of coherent light could be received by the cameras, but not directly from the light sources. In other words, the coherent light is directly received by the cameras of the imaging head 250 substantially only as reflected straight from the tire T. The reflected coherent light is captured by the cameras and, preferably, associated computer memory, over the range of test levels as a plurality of digital images of the object, as follows.

Then at step 518, a vacuum cycle is initiated wherein the vacuum pump 240 is activated by sending a command to the pump solenoid 246 to open the control valve 244 and pump air out of the vacuum chamber created between the upper and lower domes 228, 236.

As shown by step 520, the pump 240 is cycled or incremented until a desired predetermined vacuum level is reached. The predetermined vacuum levels may be stored in memory as a look-up table or the like.

At step 522, it is determined whether the desired predetermined vacuum level from step 520 has been reached. If not, then the routine continuously loops at step 522 until the desired vacuum level is reached. Otherwise, the routine proceeds to step 524, wherein another image is captured at the incremented vacuum level.

Thereafter, at step 526, it is determined whether the last image N has been taken or captured at the last of several predetermined vacuum levels. If not, then the routine loops back and repeats steps 520 through 526 until the last image is captured at the last vacuum level. At this point, the vacuum pump 240 is deactivated, the solenoid-actuated exhaust valve 248 is activated at step 528, and the routine proceeds to a tire validation sequence beginning at step 530 of FIG. 13C.

It is contemplated that the tire testing and inspection sequence may be carried out according to any number of acceptable alternatives. For example, the initial image need not be captured at a zero vacuum level but may be captured at a first incremented vacuum level. Also, the vacuum cycle need not be incremented according to increasing vacuum levels but may be decremented from an initially relatively higher level toward a relatively lower or zero level, according to decreasing vacuum levels. Moreover, the image captures need not be carried out at predetermined increments and the vacuum cycle need not include discrete stops or increments. Rather, the vacuum cycle may be continuous over a range of increments or levels and the image capture may be carried out at predetermined time intervals, at predetermined vacuum levels, randomly, or any combination thereof.

Referring to FIG. 13C, at step 530 of the tire validation sequence of the routine 500, it is preferable that an image processing step 531 be carried out substantially simultaneously as the upper dome is raised and the imaging head 250 and pallet 208 are lowered in step 502. In step 531, one or more image processing sub-routines are called and carried out and are described with reference to FIGS. 29 through 62, discussed hereinafter below. The sub-routines facilitate analysis of the images captured. It is also contemplated that the image processing and analysis step 531 could be carried out as the images are captured in steps 516 through 526. In other words, step 531 could be initiated substantially simultaneously with steps 516 through 526.

At step 534, it is determined whether an operator has activated a tire failed pushbutton or screen pick. If not, it is determined whether the operator has instead activated a tire passed pushbutton or screen pick at step 536. If the operator has not activated either pushbutton, then the routine loops back to step 534. If, however, the operator has activated the tire passed button, then the outbound non-anomalous conveyor 224 is enabled at step 538 to carry the pallet 208 and tire T off of the machine table 206. If, however, at step 534, the operator has activated the tire failed button, then the anomalous conveyor 226 is instead enabled to carry the pallet 208 and tire T off the machine table 206 at step 540. At step 542, the appropriate conveyor 224, 226 is activated and the pallet stop 218 lowered to release the tire T and pallet 208.

At step 544, it is determined whether the tire T has been released by referencing the status of the proximity switch 222 signal. If the tire T has been released, then the pallet stop 218 is raised at step 546 and thereafter the routine terminates and proceeds to auto start. If not, then the routine continuously loops at step 544 until the tire T is eventually released.

DVS HMI

FIGS. 14 through 28 illustrate some of the functionality of the HMI 402 through several graphical user interface (GUI) screen shots. GUI touchscreens provide an interactive means for a user to input data to the computer 302 for use with the software programs and/or data stored in one or more databases or database tables. Also, the GUI touchscreens preferably represent different states of the program to allow input of different data and display of data and information. The terminology GUI is interchangeable with screen, display, and the like.

Main Screen

Figure 14:
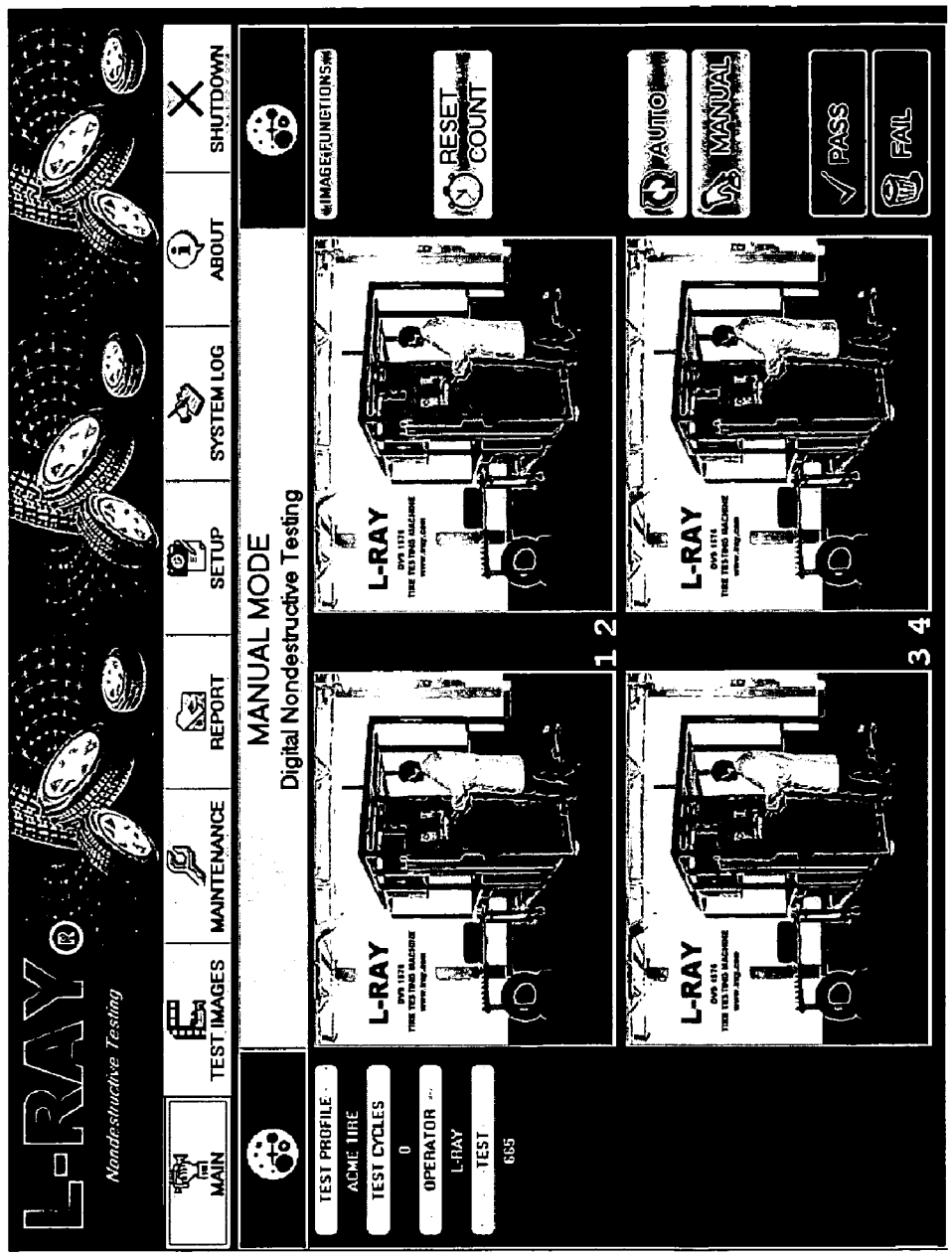
FIGS. 14 through 18 are graphical user interface screen shots that illustrate functionality of a human machine interface of the differencing video system of FIG. 12.

FIG. 14 illustrates a main screen that provides a user with auto or manual mode control, test image analysis, tire validation functionality, and basic production information. Across the top of the screen is a title banner with logo and graphics. Below the banner is a row of the following menu buttons: main, test images, maintenance, report, setup, system log, about, and shutdown; all of which are used to access various screens or functions and will be described in further detail herein below. Below the menu buttons there is a mode and status/fault indicator bar and, below that, there are basically the following three columns: a production information column on the left, an operator input column on the right, and real-time or live raw or processed images of four different sectors of the tire presented as an array of four windows in the middle column.

The production information column includes several fields including test profile, test cycles, operator, and test fields. The test profile field represents a name of a tire profile that is currently being used and that contains information regarding camera settings, camera position, and vacuum levels used to test the tire, as will be further described below with regard to the setup touchbutton. The test cycles field represents the number of cycles since last reset. The operator field represents the name of the operator that is logged on. The test field is a unique identifier for the test, and is preferably a number that is automatically incremented for each test cycle.

The operator input information preferably includes an image functions touchbutton, a reset count button for resetting the test cycles field in the production information column, auto vs. manual buttons for placing the machine in an automatic mode or a manual mode, and pass or fail buttons that an operator may press upon evaluation of final processed images to send a completed tire down a reject/fail conveyor or an accept conveyor.

As shown by FIG. 14, the image functions touchbutton may be pressed to yield an image functions toolbar, which includes image analysis tools for tire validation purposes, and may be pressed again to close the toolbar. The image analysis tools will be described in further detail below with reference to a method and functionality of image processing software illustrated by FIGS. 29 through 62. In particular, a digital image differencing function that yields a cumulative differential image (CDI) will be described in detail below. In any case, the image analysis tools may include the following tool buttons (not shown): enhanced, analyzed, overlay, invert, original, start video, and stop video.

Figure 15:
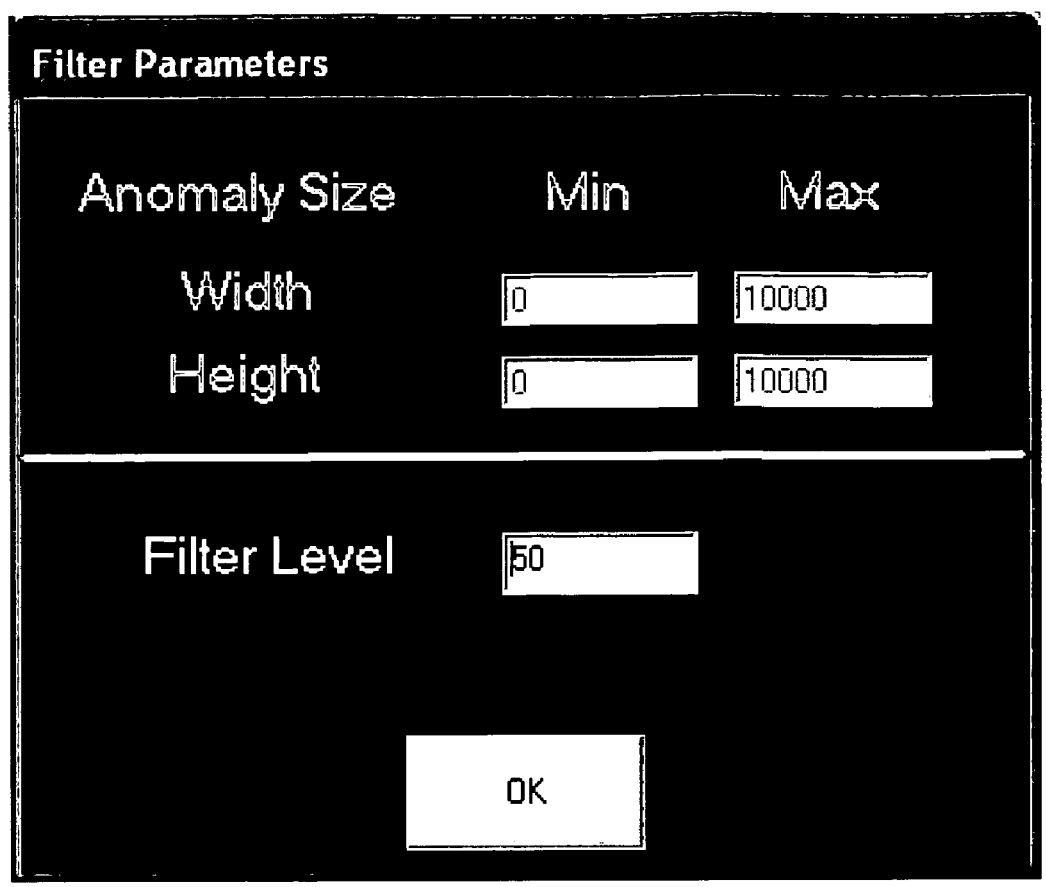

The enhanced button is pressed to perform an enhanced image process, which will be described in detail below, and, as shown by the dialog box of FIG. 15, the user will be prompted to enter a desired filter value and then press an OK button to proceed back to the image analysis toolbar. Preferably, a filter value is chosen such that only anomalies will appear in the image and the background will be eliminated. The filter value selection process is iterative wherein a higher filter number will bring more data into the image whereas a low filter number will bring relatively less.

The analyzed button is pressed to perform an analyzed image process, wherein the user is prompted to enter values for filtering, minimum width, minimum height, maximum width, and maximum height, and then press OK. This process produces a further enhanced image based on the filter value specified. The number, surface area, perimeter, and relative orientation or angle of anomalies in the analyzed image can be quantified by the dimensions specified.

The overlay button is pressed to overlay an analyzed image over an original image of the tested tire. Like the processes above, once pressed, the user will be prompted to enter values for filter, minimum width, minimum height, maximum width, and maximum height, and then press OK. This process produces a further enhanced image based on the filter value specified. The number, surface area, perimeter, and relative orientation or angle of anomalies in the analyzed image can be quantified by the dimensions specified. Furthermore, the color of the anomalies is changed from black to a different color, usually yellow, and the new color image is then overlaid onto a raw or original image of the tested tire.

The invert button is pressed to invert, or make a "negative" of, the image.

The original button is pressed to display a raw cumulative differential image.

Upon pressing any of the above mentioned buttons, the real time live images in the array of windows is replaced with the selected image types. In contrast, when the start video button is pressed the array of windows displays the real time live images. Additionally, when the stop video button is pressed, live video is stopped and the last frame from the live video stream is frozen. It is contemplated that the image differencing steps disclosed herein may be carried out in real-time to yield live video.

At the end of an image processing routine the final results of the test may be presented in the appropriate windows. The four sectors preferably refer to circumferential sectors 1, 2, 3, and 4 of the tire taken respectively approximately at 0°-90°, 90°-180°, 180°-270°, and 270°-0°. It is contemplated that the sectors could overlap if desired. The main screen is visible upon application startup and can be accessed at any time by touching the main button in the menu row.

Test Images

Figure 16:
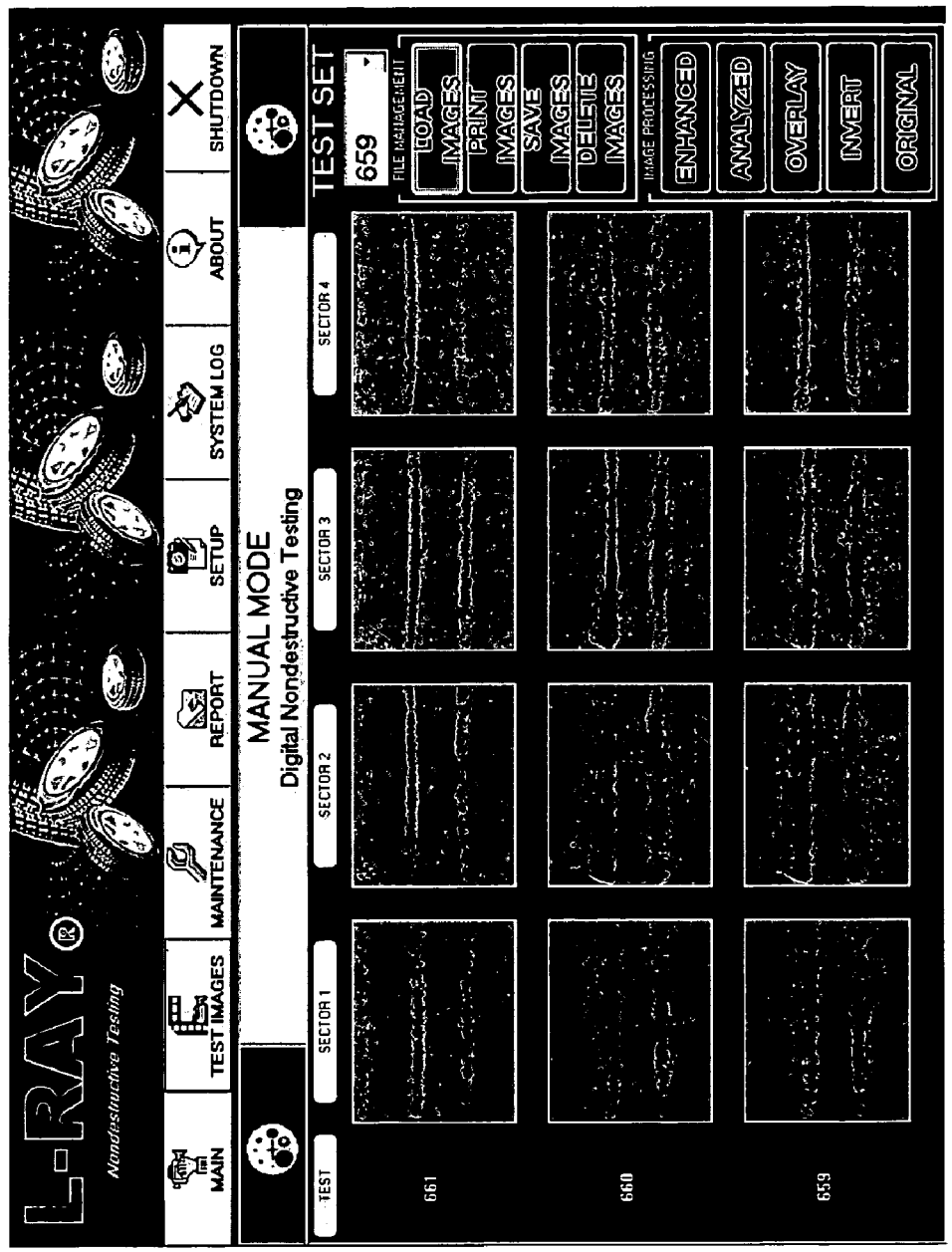

From the main screen, the test images touchbutton may be selected to show the test images screen depicted in FIG. 16, which provides the operator with a means to view, manipulate, and compare results from up to three different tests at any one time. The operator can print, save, delete, and view any images from the current or previous tests. Beneath the mode indicator bar there are the following six columns: a test column referring to the test set number indicating the sequential test identifier, four columns representing images from sectors 1 through 4, and an operator input column for the present test set.

In the operator input column, the item in the drop-down box is the presently selected test set, wherein any of the previously discussed image analysis tools (shown at the bottom of the column) or file management functions (load, print, save, delete) apply to the test set selected. The image analysis tools function similarly as described above. The file management functions include a load images button that, once pressed, the operator will be prompted to enter a test set to be displayed via a popup number pad dialog box (not shown). Thereafter, the newly selected images will be displayed over the currently selected test set.

Figure 17:
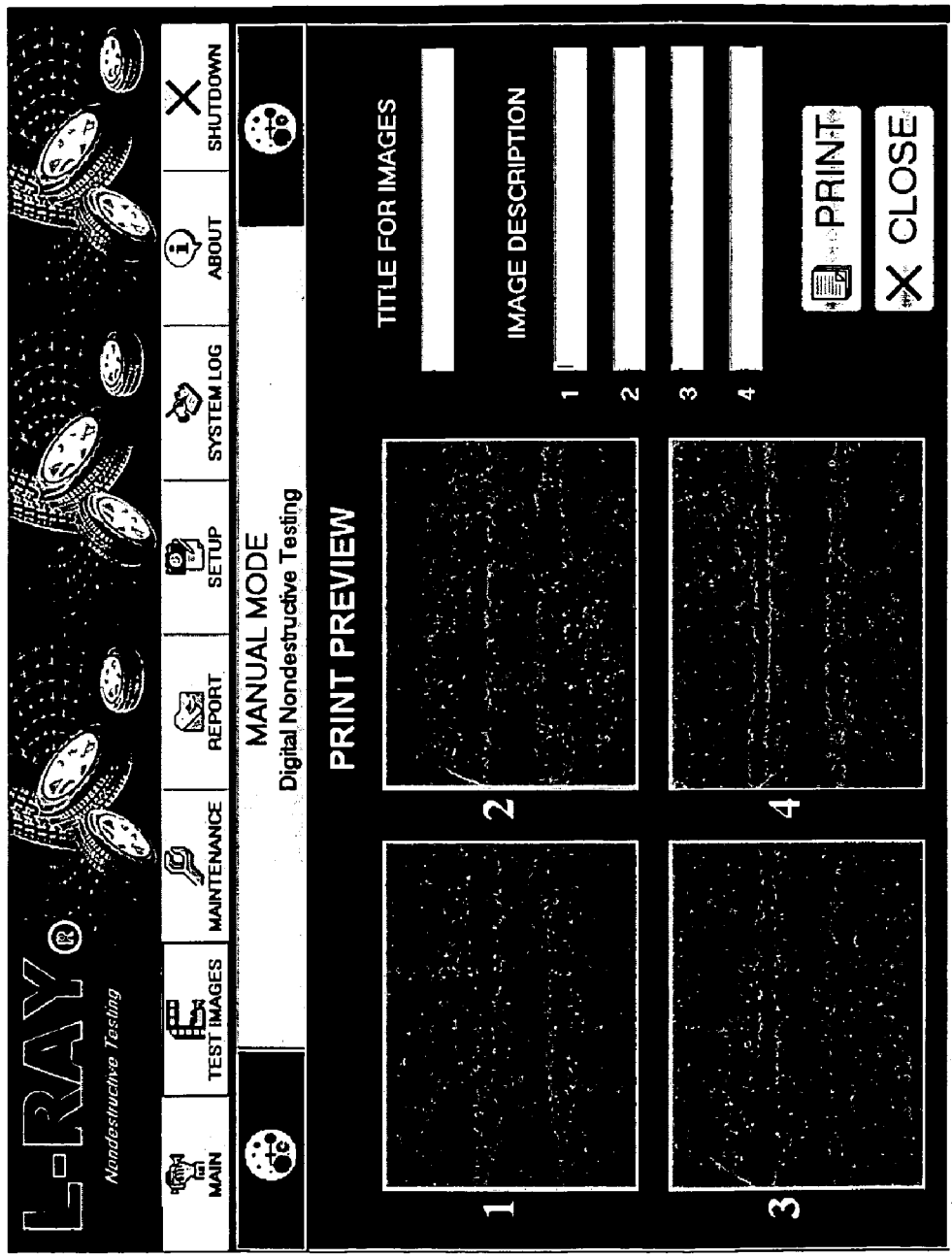

Once the print images button is pressed, the operator is presented with a print preview screen of the test set selected, as shown in FIG. 17. The print preview screen will show the test set in whatever state it was last in (i.e. analyzed, overlaid, enhanced, inverted, or original). The print preview screen also allows the operator to enter a title for the print set and a description for each sector that will print along side the images. The operator presses print to print to the printer and presses close to return to the previous screen. The save images button is pressed to present the operator with a save dialog box from which the currently selected test set can be saved to another location (i.e. local hard disk, remote server, and the like) and/or be renamed. The delete images button is pressed to query the operator to verify that the files for the currently selected test set should be deleted. If OK is pressed, then the files will be permanently deleted.

Maintenance Tool

Figure 18:
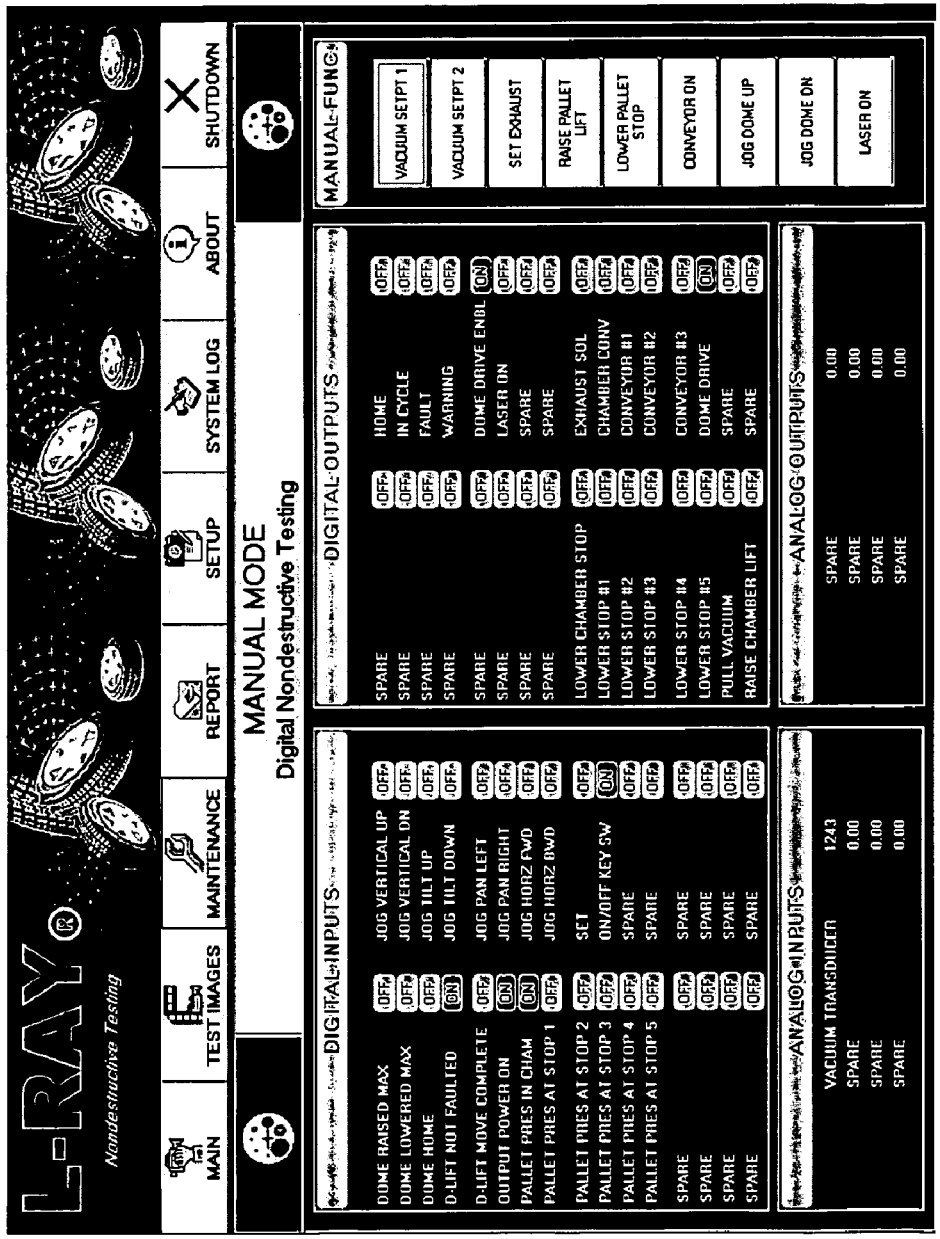

From any of the menu screens, the maintenance menu button may be touched to access the maintenance screen, which is shown in FIG. 18 and which allows an operator and/or maintenance person to verify that all of the machine inputs and outputs (I/O) are working correctly. An operator can also manipulate certain I/O while in manual mode. The maintenance screen includes three columns including a first column or inputs column with a digital inputs box and an analog inputs box, and a second column or outputs column with a digital outputs box and an analog outputs box. The inputs and output boxes display all of the machine digital inputs and outputs and their current state of ON or OFF and all of the machine analog inputs and outputs and their current value.

A third column is a manual function column including the below described manual command touchbuttons. A vacuum setpoint 1 button is pressed to set system vacuum to setpoint 1, which is predefined in the system setup screen described in further detail herein below. The upper dome is preferably down in order for this function to be enabled. A vacuum setpoint 2 button is press to set system vacuum to setpoint 2, which is also predefined in system setup. Again, the upper dome is preferably down in order for this function to be enabled. A set exhaust button is pressed to activate the exhaust solenoid and thereby release the vacuum within the vacuum chamber, and is pressed again to deactivate the exhaust solenoid. A raise pallet lift button is pressed to raise the pallet lift, and is pressed again to lower the pallet lift. A lower pallet stop button is pressed to lower the pallet stop, and is pressed again to raise the pallet stop. A conveyor on button is pressed to activate the incoming conveyor, and is pressed again to deactivate the conveyor. A jog dome up button is pressed to jog the upper dome up, and is released to stop the upward movement of the upper dome. A jog dome down button is pressed to jog the dome down, and is released to stop the downward movement of the upper dome. A laser on button is pressed to activate the imaging equipment lasers, and is pressed again to deactivate the lasers.

Camera Position Control Pendant

Not currently integrated into the HMI interface is the functionality of the separate camera position control pendant 260, mentioned previously and illustrated in FIG. 19. The camera position control pendant 260 is used to manually control each axis of the imaging head. A horizontal rocker switch is pressed to move the cameras horizontally toward, or away from, the tire. A vertical rocker switch is pressed to move the imaging head up and down with respect to the machine table, out of and into the lower dome. A tilt rocker switch is pressed to tilt the cameras toward, and away from, the upper dome. A pan rocker switch is pressed to rotate the imaging head clockwise or counterclockwise.

Report

Figure 20:
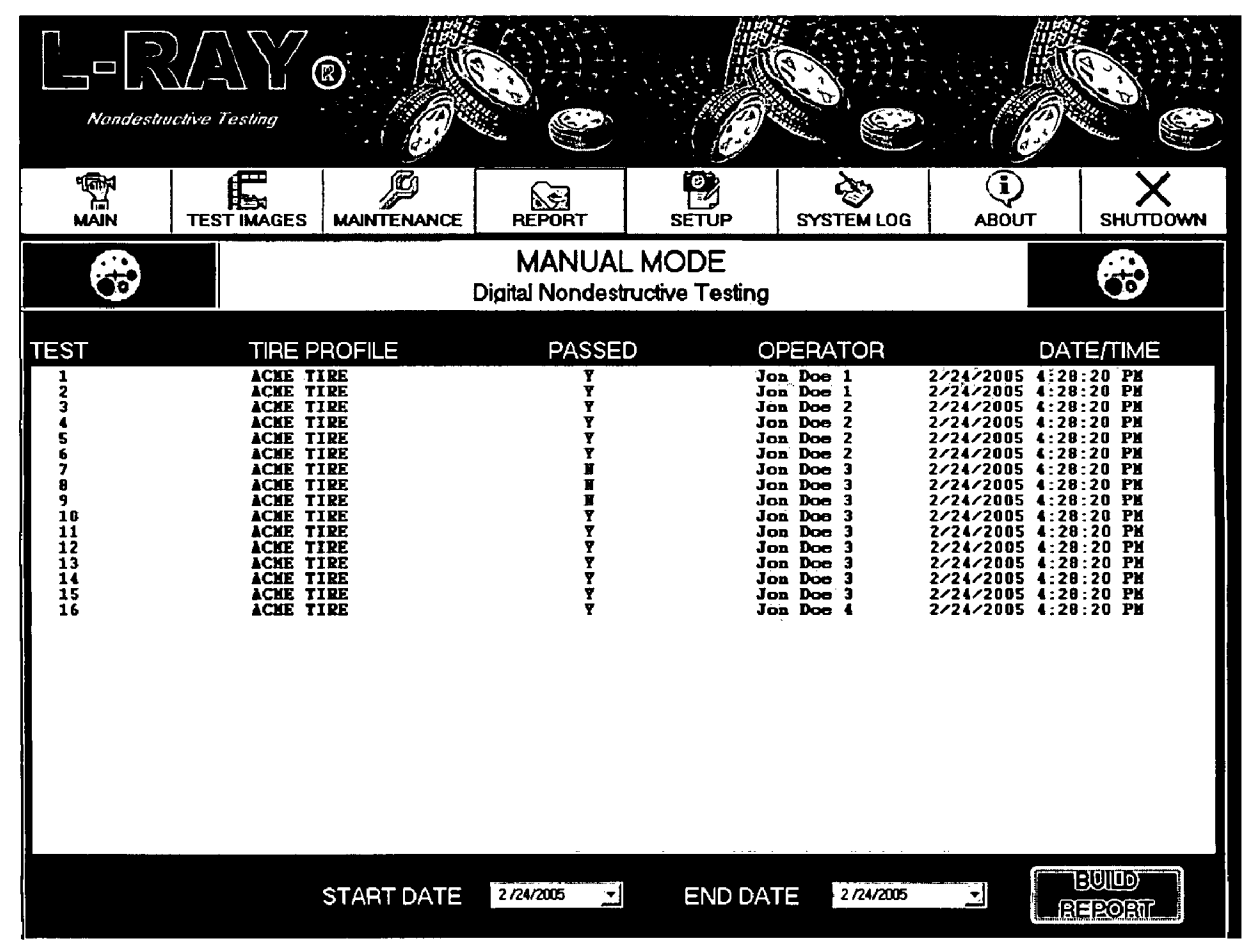

As shown in FIG. 20, the report menu button of the toolbar may be pressed from any of the toolbar menu screens to access a report screen, which allows an operator to view various production details. As just one example, the production details may include tire profile, tire validation (pass/fail), operator, and the date/time of tested tires. Those of ordinary skill in the art recognize that information presented on this screen can be customized to any given application according to needs of a particular customer. A build report button may be pressed to generate a report after entering start and end dates in the fields to the left of the report button.

Setup

Figure 21:
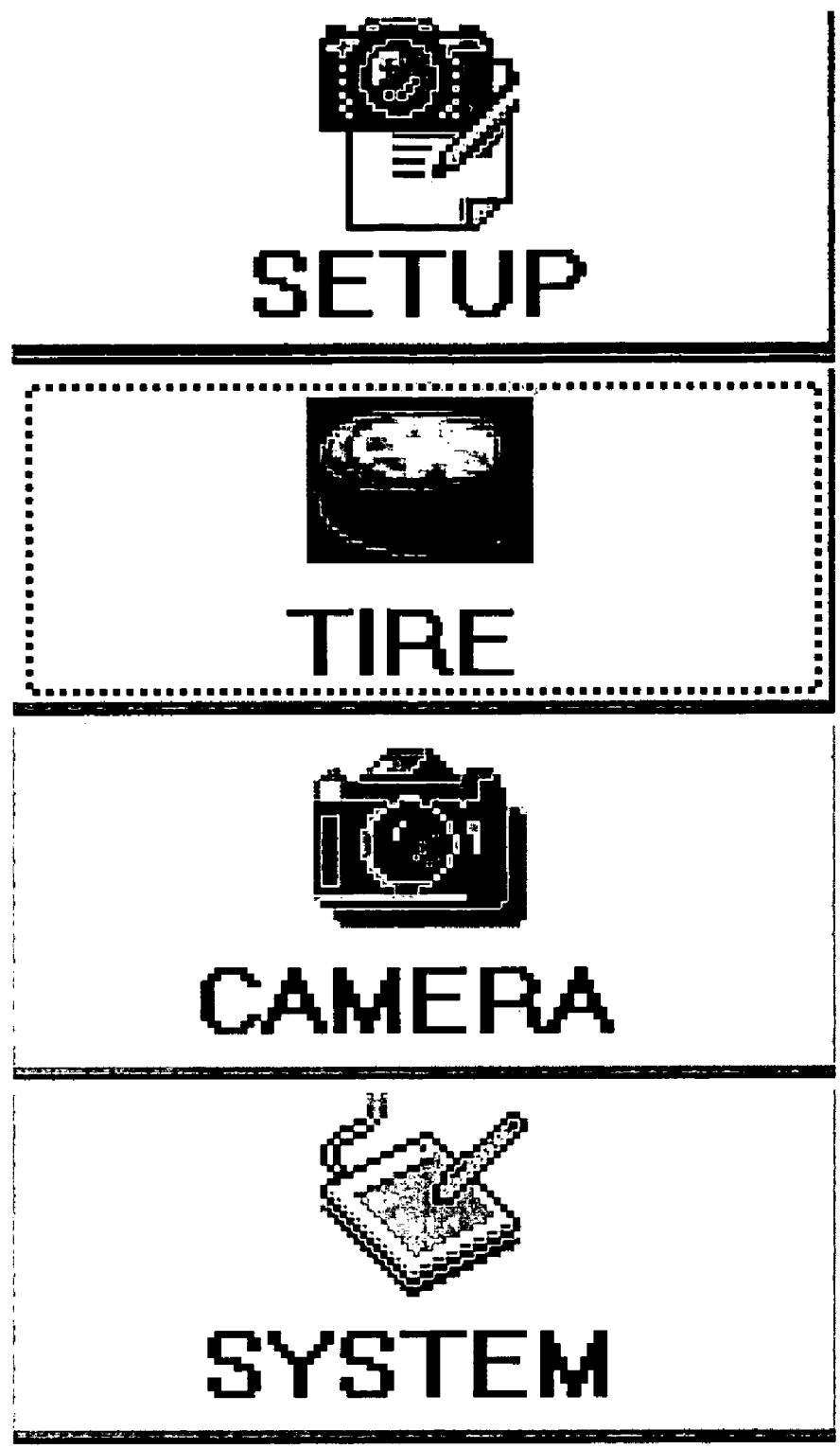

From any of the toolbar menu screens, including the main report screen of FIG. 20, a setup menu button of the toolbar may be pressed to access a drop down button menu including tire, camera, and system setup buttons, as shown in FIG. 21. Pressing the various setup buttons leads to corresponding setup screen which allows the operator to setup various profiles.

Tire Setup

Figure 22:
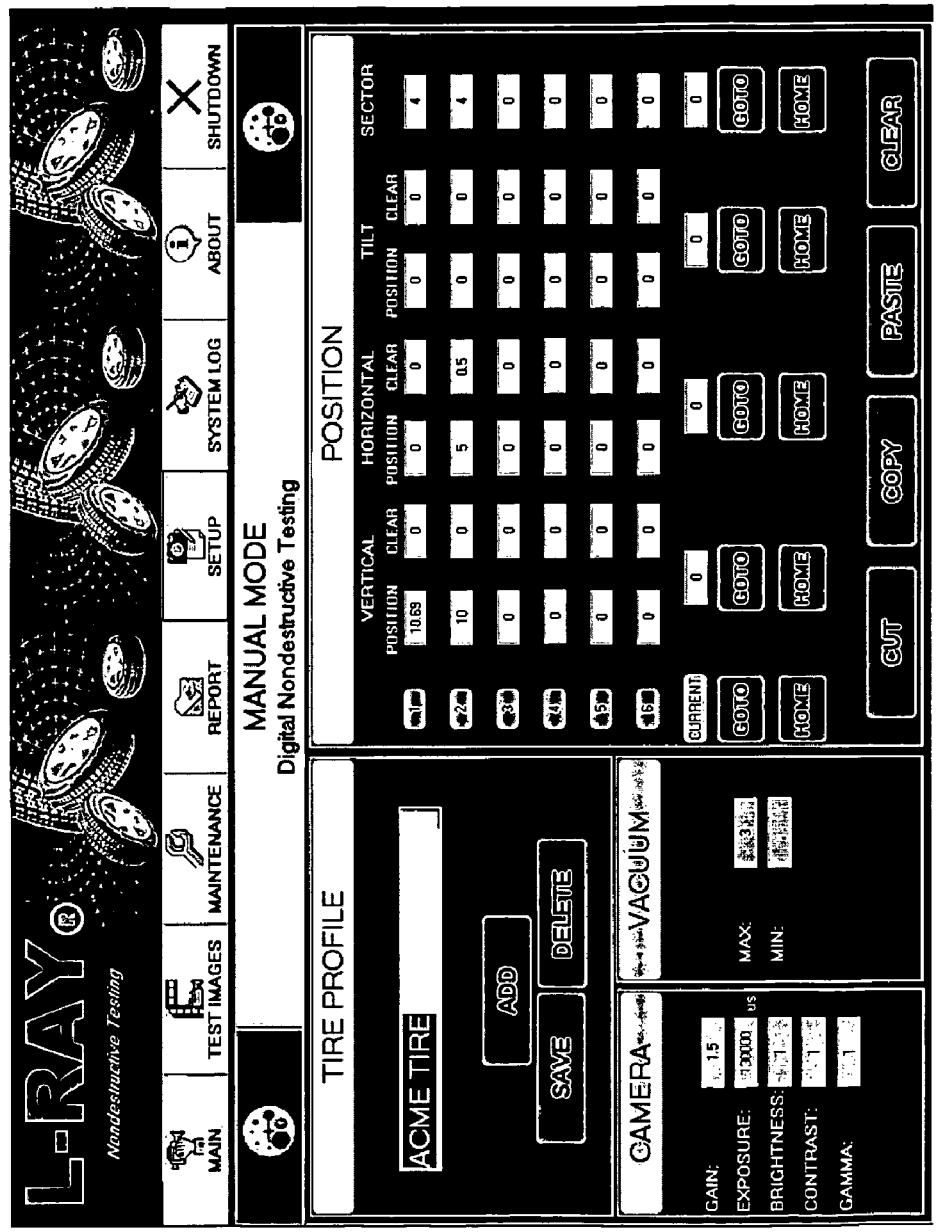

Pressing the tire button permits a user to access a tire profile or setup screen, which is shown in FIG. 22 and is used to accommodate variations in tire models due to size, looseness, and illumination. The tire profile may be manually selected for each batch of tires run. But it is contemplated that if the tires are incorporated with a barcode, RFID, other identifier technology that can be recognized via OCR (Optical Character Recognition), and the like, then an auto identify system can be adapted for use with this tire profile function to automatically populate and or select the values and settings discussed below. In any case, the screen includes a tire profile box, a camera box, a vacuum box, and a position box.

The camera box addresses camera settings, wherein several camera settings are shown such as gain, exposure, brightness, contrast, and gamma that pertain to the currently selected profile from the tire profile box. It is contemplated that camera iris and focal fields, among others, could be added to this box. In any case, one or more of the fields can be modified and saved to the current profile.

Similarly, in the vacuum box, there are shown current maximum and minimum vacuum settings that can be modified and saved to the current profile.

Figure 19:
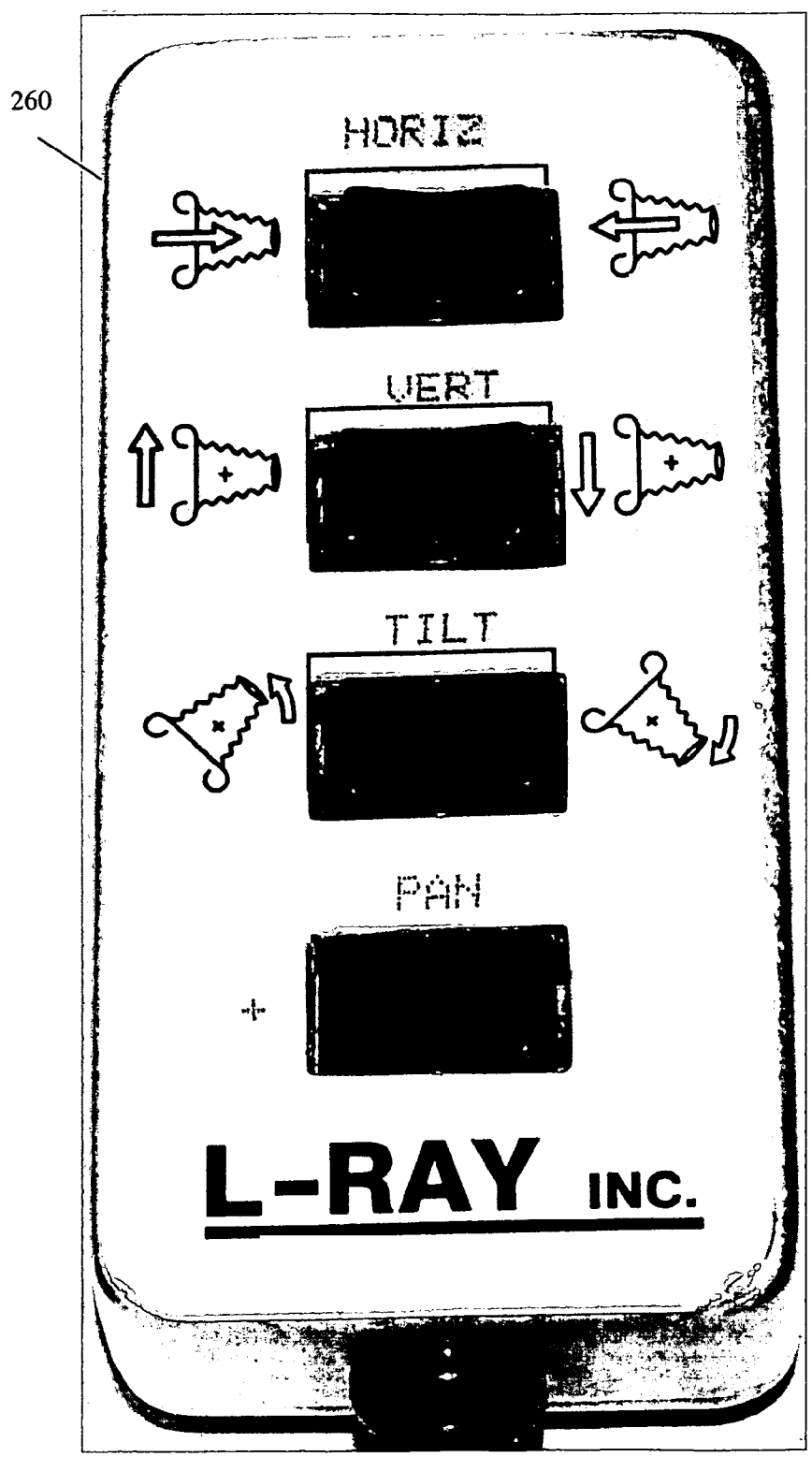
FIG. 19 is plan view of a camera position control pendant for use with imaging apparatus of the production system of FIG. 9.

The position box controls camera position relative to the tire being tested, and allows an operator to configure up to 6 different positions. As shown, there is a position array including five columns and six rows. The five columns include positions 1 through 6 of the 6 different positions, a vertical position column, a horizontal position column, a tilt position column, and a sector column. The position field in each of the relevant columns is the actual position in inches that the individual camera should move from its home position. The clear field in each of the relevant columns is a position in inches where no obstructions are present and the camera can safely move from one position to the next. The numbers one through six are buttons that may be used in conjunction with the copy, cut, paste, and clear buttons. The "current" field displays current vertical, horizontal, tilt, and sector data of the camera and is not a button. The pendant of FIG. 19 is used to move a camera to an appropriate spot using live video feedback. The operator then enters the current position coordinates into the appropriate position number.

At the bottom of each of the vertical, horizontal, tilt, and sector columns there is an entry field, a go to button, and a home button. Pressing the go to button under a particular position number of a particular position type will move appropriate portions of the imaging head to all relevant axes. In other words, if the go to button is pressed in the vertical column, then only the corresponding portion of the imaging head will move to the vertical axis position specified. Likewise, pressing the home button sends the imaging head to the home position for that position number or axis.

In the tire profile box, an existing tire profile may be selected for viewing via the drop-down menu (ACME TIRE). The tire profile function allows a user to save the camera, vacuum, and position settings described above, or retrieve already saved such settings. Otherwise, an add button may be pressed to create a new tire profile. A save button may be pressed to save any changes made to the currently selected profile. And a delete button may be pressed to permanently delete the currently selected profile.

Beneath the position array, there is a row of tool buttons including cut, copy, paste, and clear. Pressing the cut tool button copies the currently selected position values and turns the position number color from green to red, thereby indicating that the values will be cleared after pressing the paste tool button. A position is selected by clicking on the position number, which will turn the number from grey to green. Pressing the copy tool button merely copies the currently selected position values and turns the position number color from green to yellow. Pressing the paste button pastes the values from a position that was cut or copied from (i.e. yellow or red position), whereafter the yellow or red position number color is turned back to grey. Pressing the clear button clears values from the currently selected position number 1-6.

A second page (not shown) of the tire profile may contain fields for entering tire specific data such as manufacturer, model, size, new or used, customer name, anomaly constraints, and the like.

Camera Setup

Figure 23:
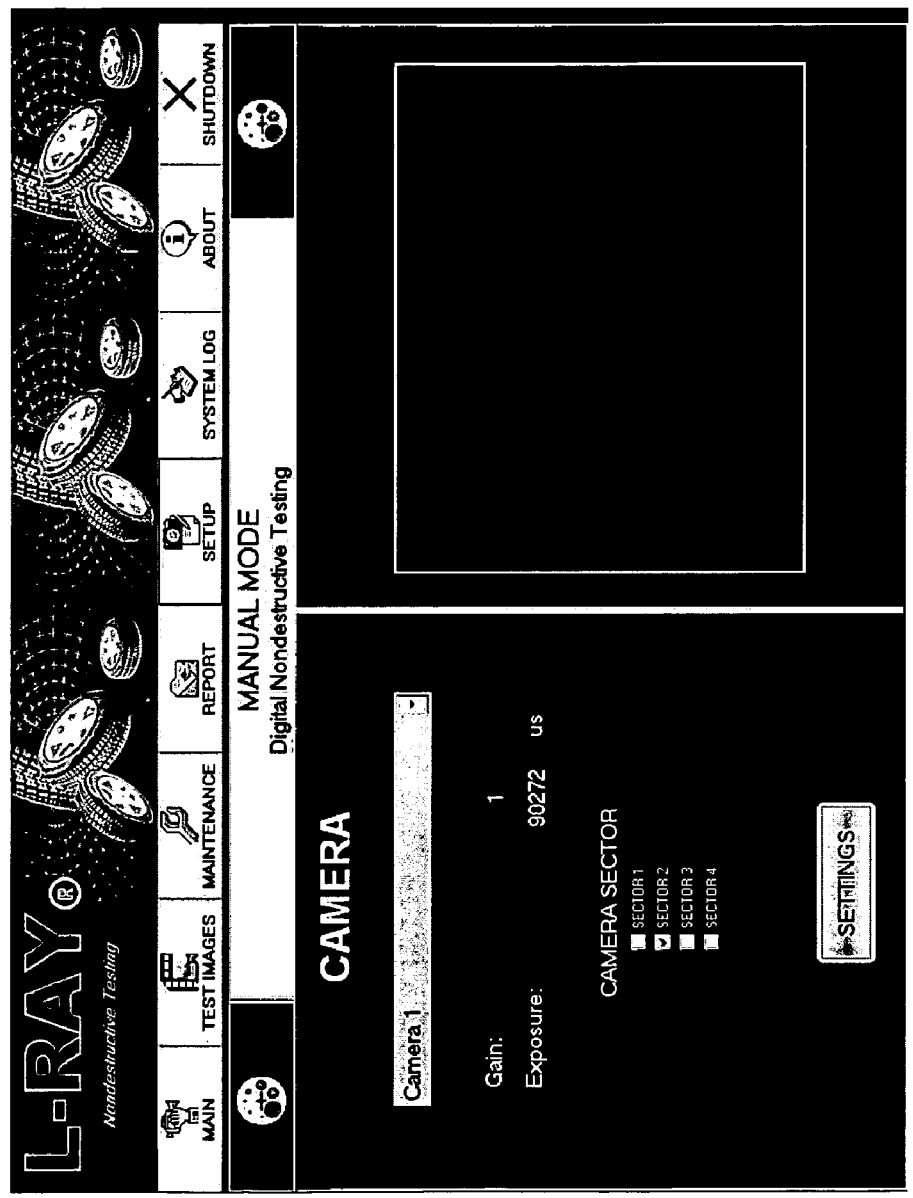
Figure 24:
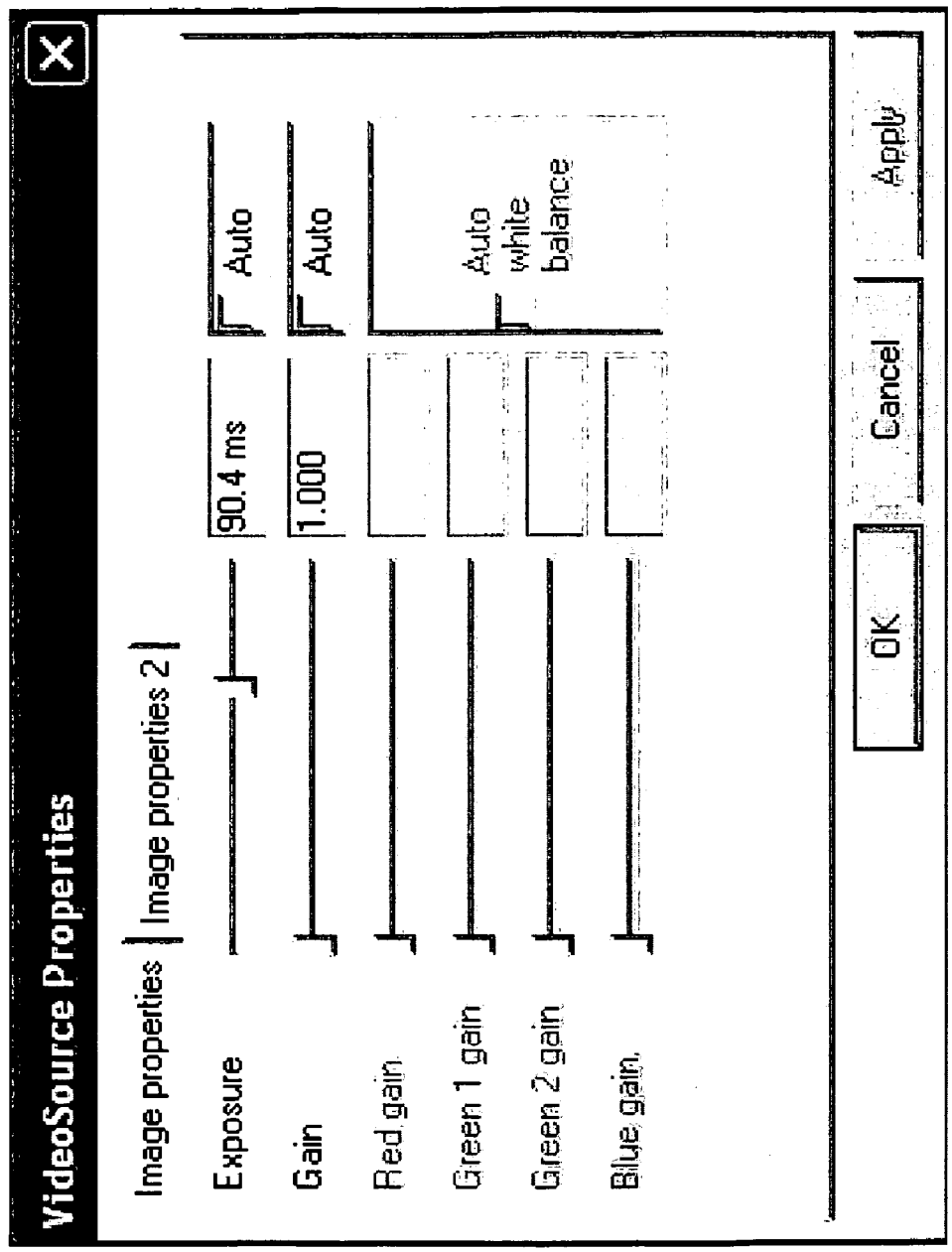
Figure 25:
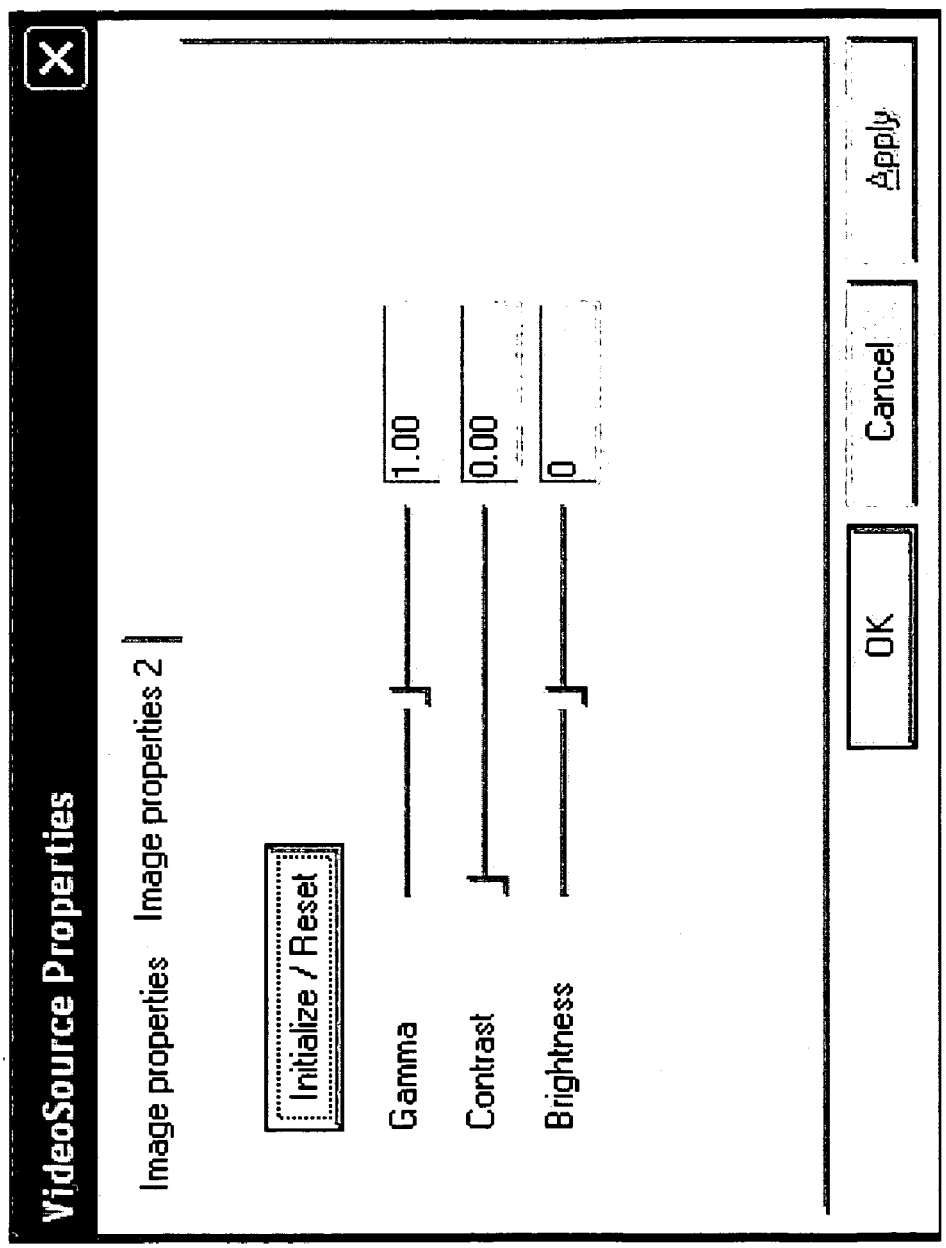

As shown in FIG. 21, the setup button of the toolbar may be pressed to access the drop down button menu after which the camera setup button may be pressed to access a camera setup screen, which is shown in FIG. 23 and allows an operator to setup the default properties by sector such as gain, exposure, brightness, contrast, and gamma. This screen provides a live video stream from the currently selected camera, which can be selected from the drop down field for previewing and/or modification. Below the drop down field, the properties of currently selected camera are shown including gain and exposure. Below that, a camera sector section shows the sector of the tire that is associated with the currently selected camera. This property can be changed by clicking the checkbox of the appropriate sector. Further below, a camera settings button can be pressed, whereafter the operator will be prompted with a dialogue box that will allow the operator to change the camera gain, exposure, brightness, contrast, and gamma, as shown in FIGS. 24 and 25, which show the preferred settings.

System Setup

Figure 26:
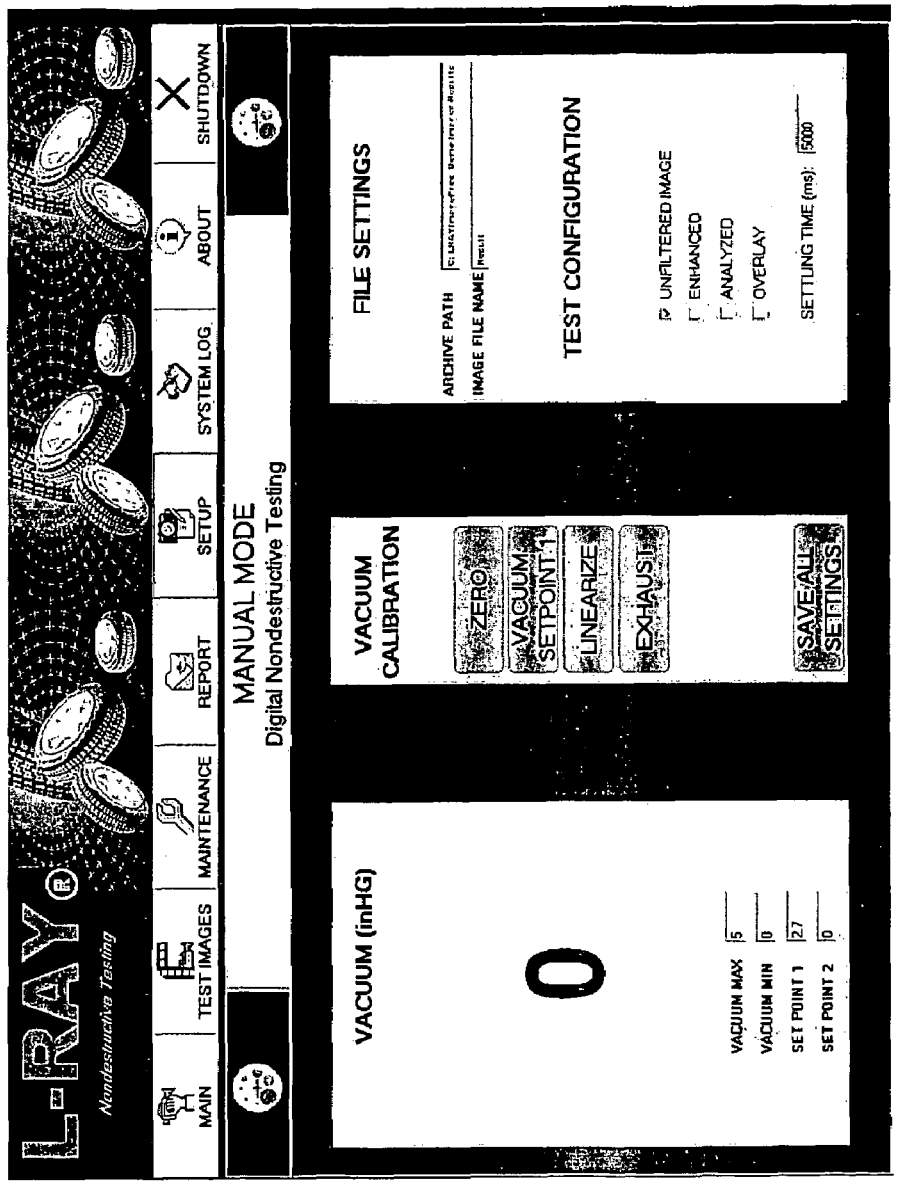

As shown in FIG. 21, the setup button of the toolbar may be pressed to access the drop down button menu after which the system setup button may be pressed to access a system setup screen, which is shown in FIG. 26 and allows an operator to modify system default vacuum, image archival, and test settings. A vacuum box displays the current vacuum level in inches of mercury (inHg), and settings for maximum vacuum, minimum vacuum, and first and second vacuum setpoints. Setpoint 1 is the maximum default vacuum level for carrying out the testing and inspection process, wherein this value is used if another value is not specified in the tire profile. Setpoint 2 is the minimum default vacuum level for carrying out the testing and inspection process, wherein this value is used if another value is not specified in the tire profile. The desired number of vacuum points are preferably equidistantly scaled over the vacuum range with a minimum of 0.5 in Hg increments. For example, if the vacuum range is 0-2.5 in HG, then images at 0, 0.5, 1, 1.5, 2, and 2.5 will be taken. If, however, the vacuum range is 0-3.5 in HG, then images at 0, 0.7, 1.4, 2.1, 2.8, and 3.5 will be taken.

A vacuum calibration box is provided for carrying out several vacuum calibration steps. Vacuum calibration is carried out by first putting the system in manual by pressing the manual button on the main screen, and then lowering the upper dome via the maintenance screen. Next, the exhaust button on the system setup screen is pressed to eliminate any vacuum in the vacuum chamber. Then, the zero button is pressed to obtain a zero offset value and, thereafter, a vacuum setpoint 1 button is pressed to set the vacuum level to the value in the setpoint 1 field. Finally, a linearize button is pressed to finish the calibration. Thereafter, the exhaust button may be pressed to exhaust the vacuum chamber to enable lifting of the dome.

A file settings and test configuration box is also provided. A file settings portion includes an archive path field to define where processed images are stored, and further includes an image file name field to define a file name template, wherein an exemplary default format is TireProfile_TestID-Sector.bmp. One of the check boxes—unfiltered image, enhanced, analyzed, and overlay—may be checked for the desired type of image to be displayed at the end of the image processing. These settings and their associated functionality will be discussed below in detail with respect to routines and associated software. A settling time field may be completed to define the time in milliseconds before starting the vacuum cycle once the dome is fully lowered against the machine table. Finally, a save all settings button may be pressed to save all system settings.

System Log

Figure 27:
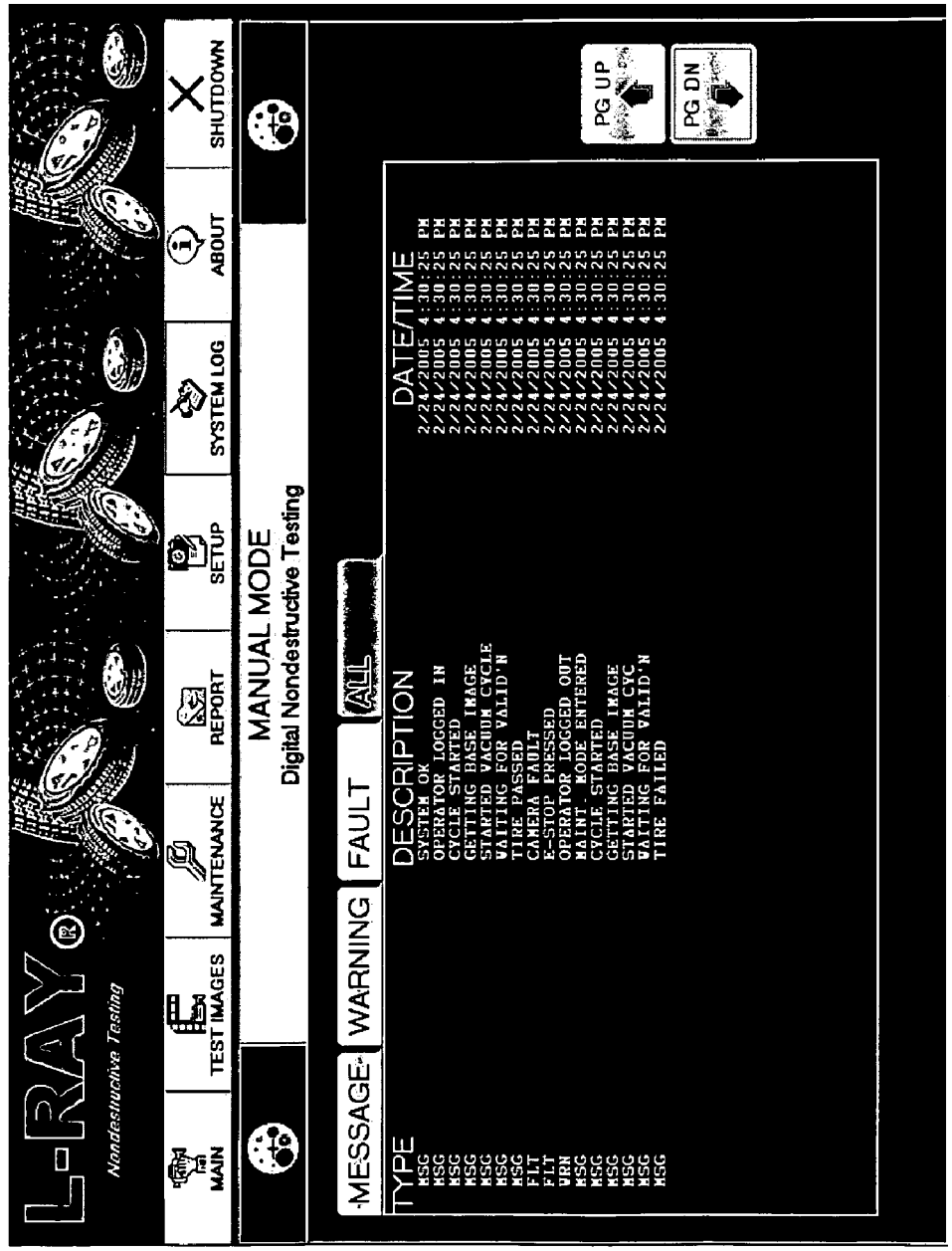

As shown in FIG. 27, the system log menu button of the toolbar may be pressed from any of the toolbar menu screens to access a system log screen, which allows an operator to view various system events. For example, all system messages, warnings, and faults are saved and displayed on this screen. An all tab may be selected to view all messages, warnings, and faults. Whereas message, warning, and fault tabs may be selected to screen for the selected types of events. Page up and page down buttons enable scrolling among the various events.

About

Figure 28:
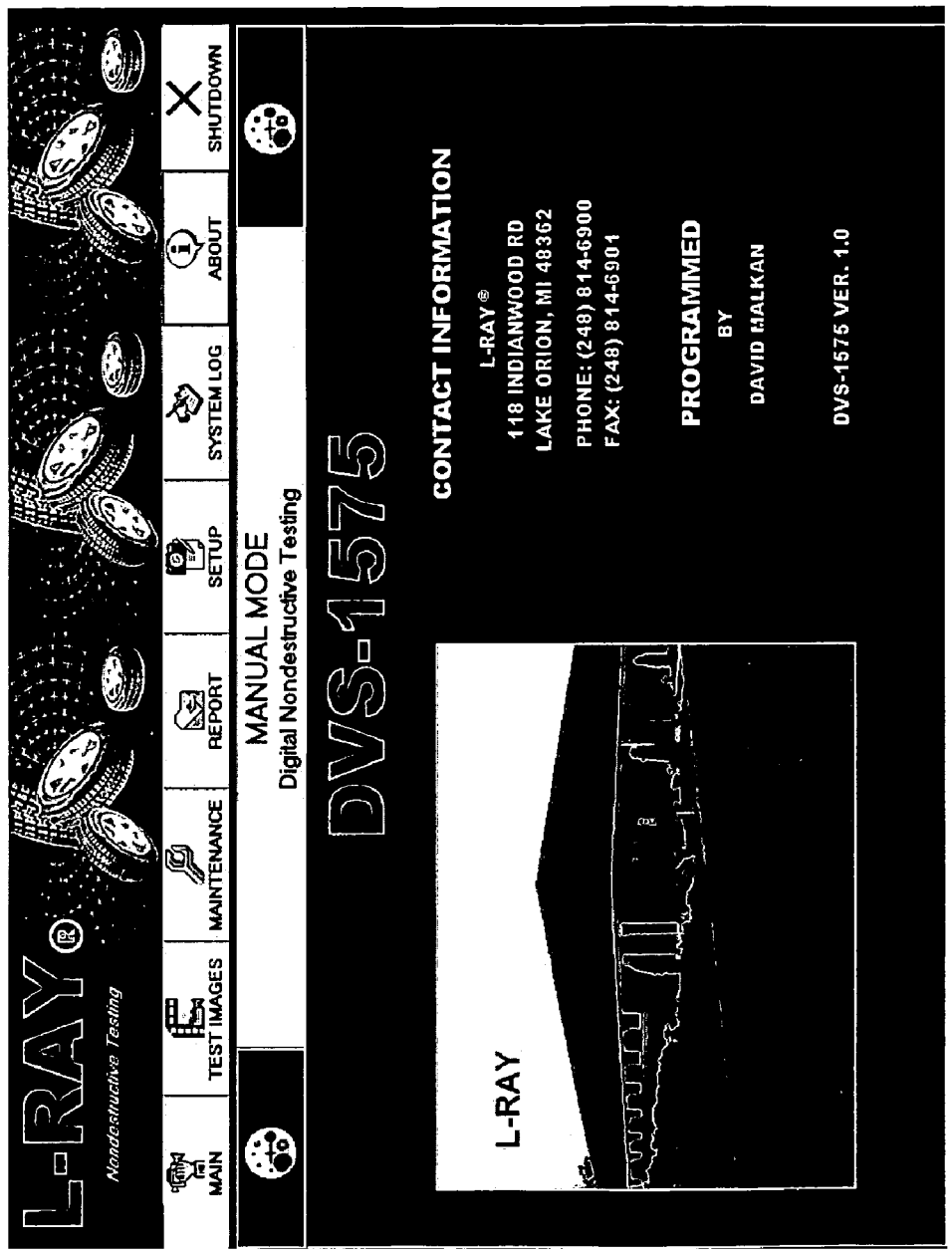

As shown in FIG. 28, the about menu button of the toolbar may be pressed from any of the toolbar menu screens to access an about screen, which allows an operator to view information regarding the system type, software version, and contact information.

Shutdown

As shown in any of the toolbar menu screens discussed above, a shutdown menu button may be pressed to close the program.

Image Capture and Analysis

Using the apparatus and methods described above and using preferred image processing routines described herein, it is possible to capture a first straight reflection from a test object as a first image and thereafter capture a second straight reflection from the test object as a second image, and then compare the difference of the reflected light from the two images between unstressed and stressed conditions of the object and/or between stressed conditions of different magnitudes. The cameras directly receive the coherent light substantially as reflected straight from the test object. Moreover, the cameras and/or the control module capture the reflected coherent light over the range of test levels as a plurality of digital images of the test object.

According to the reflection law of physics, when a surface of the test object moves, each individual reflective ray of light moves to a different position, wherein the imaging equipment senses the position change, thereby yielding a difference between image captures. Using the routines discussed herein, anomalous regions within the captured images can be viewed without confusion of fringes and/or double images associated with previous testing and inspection approaches. The images can be further processed to enhance the images for better viewing by humans, to count anomalies, to measure anomalies, and/or to display just the anomalies or the anomalies as overlaid onto a baseline image.

In general, an exemplary differencing routine may include captures of six images equally spaced between 0.0 in. Hg. and 2.5 in. Hg. Capture is triggered by a vacuum transducer connected to the CPU, wherein the vacuum transducer is read or sampled many times per second. At each setpoint, an image is captured according to a live differencing routine described herein below). Three pairs of images taken at 0.0 and 0.5 in Hg; 1.0 and 1.5 inHg; and 2.0 and 2.5 inHg, are differenced to produce image A, image B, and image C. Images A and B and C are added to produce a raw cumulative differential image (raw CDI), which is thereafter digitally processed or finessed to produce a resultant CDI. The resultant CDI is further digitally processed using an enhancement routine to produce an enhanced CDI, an analyzed CDI, and/or an overlaid CDI. The methods described herein may be performed by the computer 304 as a computer program and various predetermined setpoints or other values may be stored in memory as a look-up table, or the like.

The resultant CDI is composed of speckle patterns that exhibit a pixel value from 0 thru 255 grayscale (from black to white) with light or bright areas representing the presence of motion or departure from a previous position (i.e. the presence of an anomaly). As discussed above with respect to the image functions button of the DVS HMI, an operator may set a filter value to specify a threshold level with all portions of the image above that filter value appearing white and everything below turning black (i.e. the presents of an anomaly). The computer may then count the number of black anomalous areas and calculate anomaly surface areas and perimeters in pixels. The chosen resultant image can then be displayed on the interface screen inverted or overlaid and then the image files stored.

A more detailed description of the functionality of the image processing software is presented below and illustrated in FIGS. 29 through 62 showing several GUI screen shots and various image processing subroutines, any one or more of which may be carried out as, or called by, step 531 of FIG. 13C using MontiVision or any other suitable image processing software. Preferably, all subroutines are carried out for each individual camera of the imaging head, and any properties of MontiVision function blocks that are not explicitly stated or shown are preferably assumed to have their default properties. As an initial matter, default properties for MontiVision BayerToRGB filters and for MontiVision Demosaic Method and Correction Matrix are preferably set to "none".

Video Configuration

Figure 29:
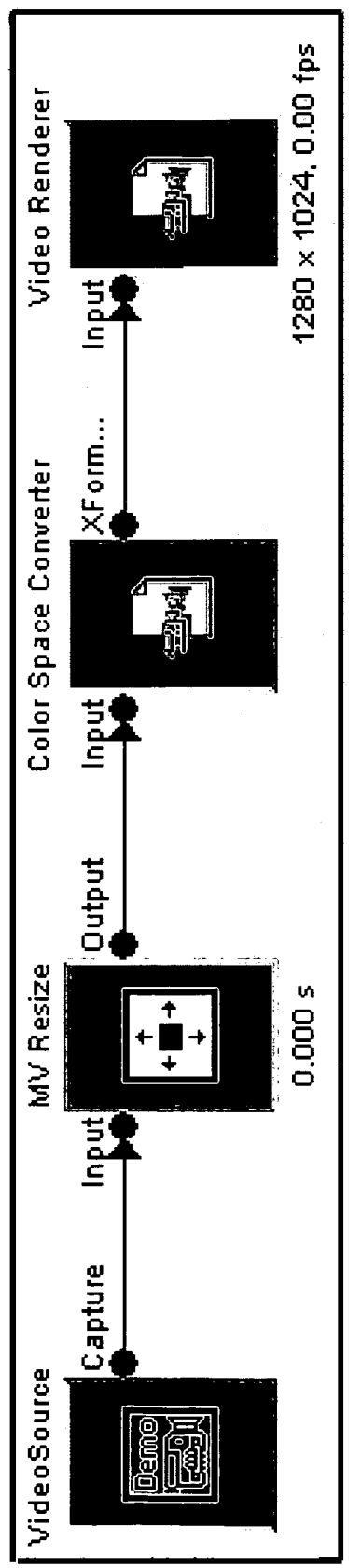
FIGS. 29 through 38 are graphical user interface screen shots that illustrate functionality of the image processing software of FIG. 12.
Figure 30:
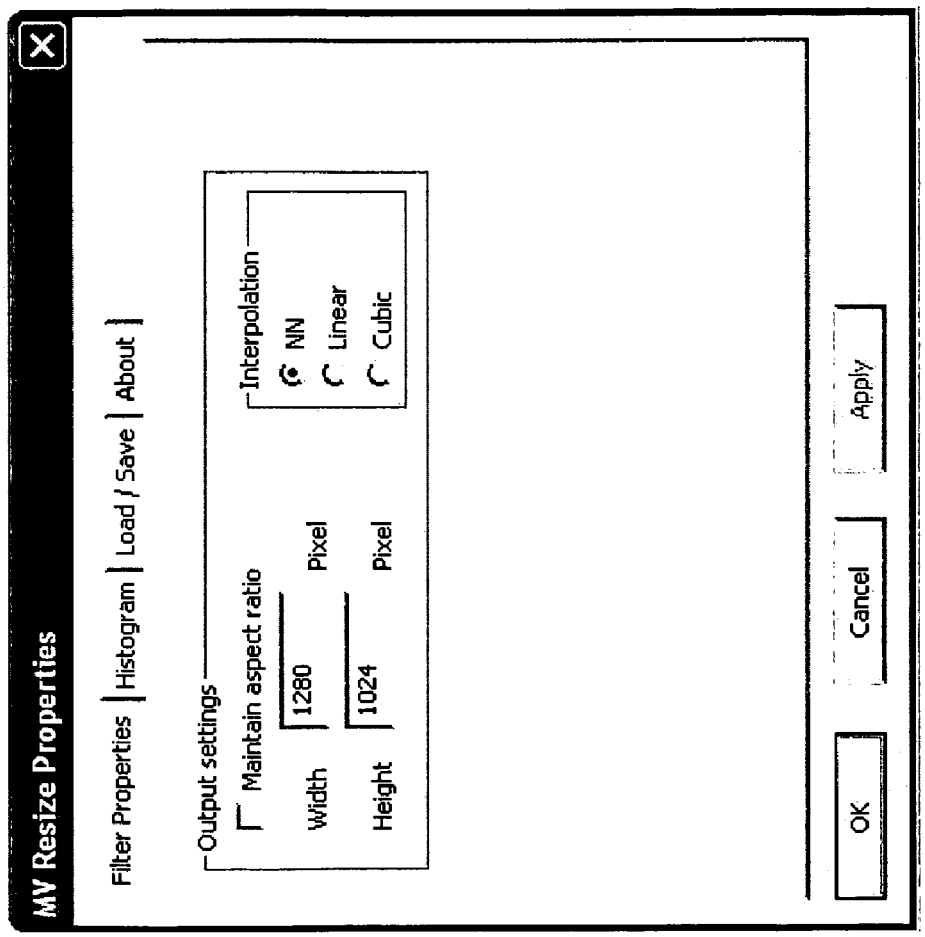

A video configuration routine is shown in FIG. 29 and is used to initialize camera properties when the HMI 402 of FIG. 12 is activated. As shown in FIG. 29, a VideoSource function represents capture of a video signal or stream and a line connects a capture node of this function to an input node of a Resize function. The Resize function effectively resizes the video stream and dictates certain properties of the video signal as exemplified by a Resize properties dialog box of FIG. 30, wherein an exemplary preferred output image size is 1280 pixels in width by 1024 pixels in height and includes nearest neighbor (NN) interpolation. The output from the Resize function goes to an input of a Color Space Converter, which converts between different color spaces, e.g. RGB24 to RGB32, RGB to YUV, etc., thereby connecting different modules that do not support each other's color space. The output from the Color Space Converter goes to an input of a Video Renderer function, which renders a video stream to a VGA, PAL/NTSC, or like monitor using a graphics card "TV Out" function and uses the DirectX® module to achieve best possible performance. Accordingly, video stream can be displayed in a window or on a full monitor screen, or on an analog monitor (TV), or the like.

Live Video

Figure 31:
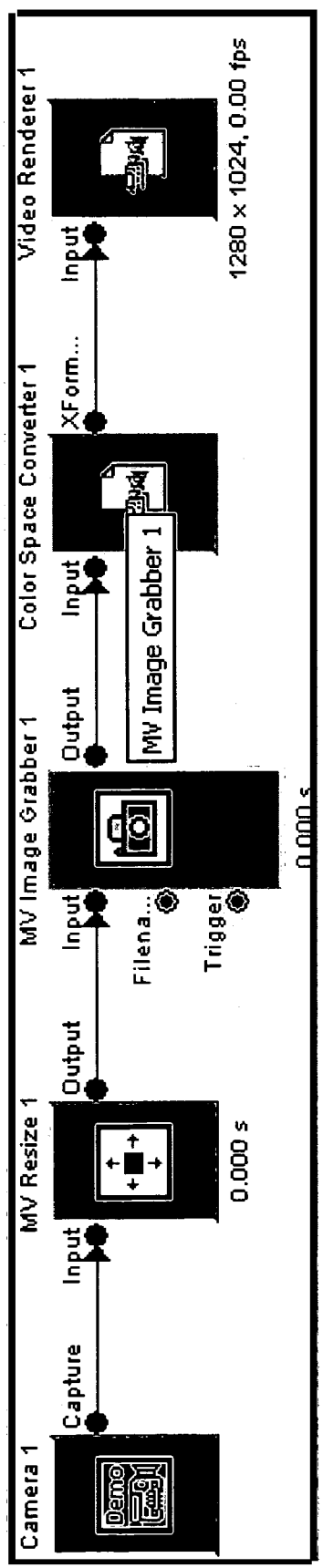
Figure 32:
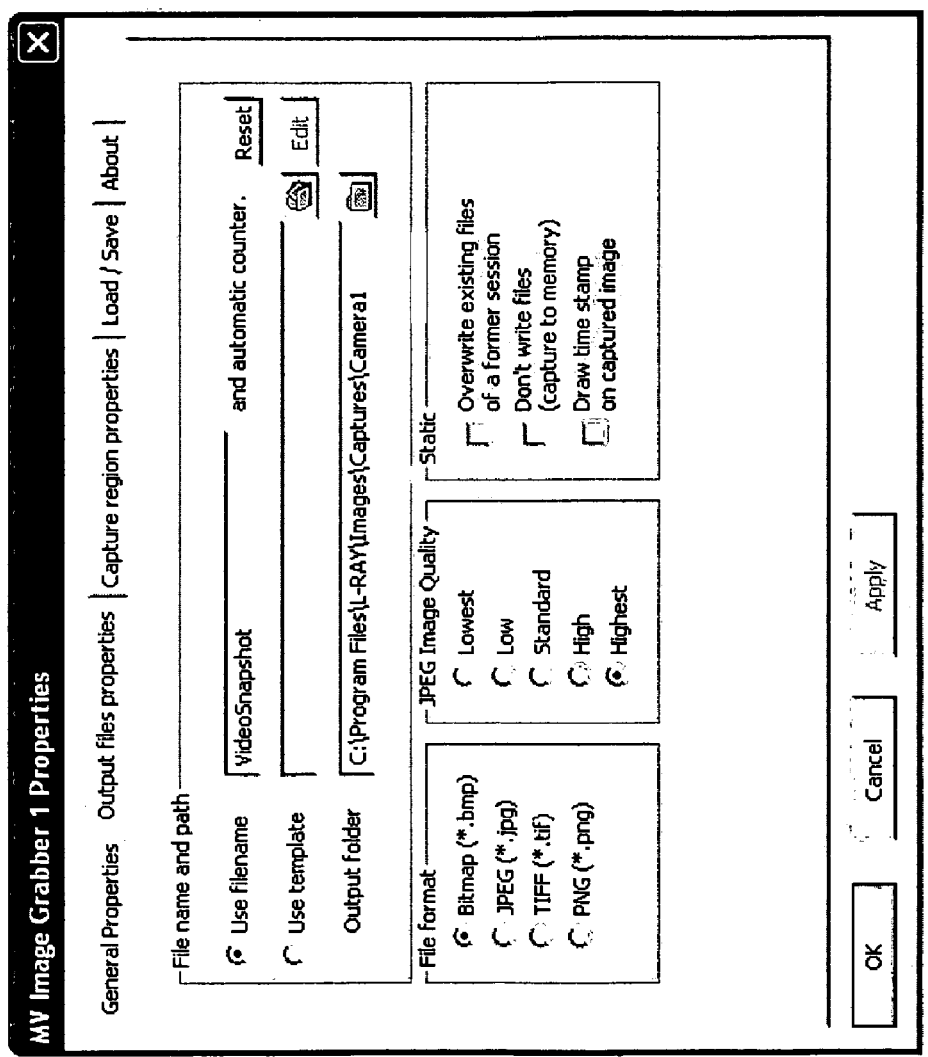

A live video routine is illustrated in FIG. 31 and is called when an operator presses the start video button of the HMI. Thereafter, image data is obtained, preferably from all of the cameras, then resized as discussed above, and rendered so that it can be displayed on the HMI. Only one camera process is shown, as an example. The live video routine is preferably identical to that of FIG. 29, except that an Image Grabber function is applied between the Resize and Color Space Converter functions. In general, the Image Grabber is used to capture stills or snapshots of the video stream and supports output of various file formats including: Bitmap (*.bmp), JPEG (*.jpg), TIFF (*.tif), and PNG (*.png). This snapshot functionality is preferably implemented using an IMVTrigger Interface function of MontiVision. A video frame is saved as single image file on every trigger event, and the names of the output files can be defined using file name templates if desired. FIG. 32 depicts the output file properties of the Image Grabber that are set as shown, including a file name of VideoSnapshot with an automatic counter that assigns sequential numerical extensions to the file names. Those of ordinary skill in the art will recognize that the particular file names are exemplary and may be specified for any given application as desired. Preferably, the Image Grabber allows for capture of the last frame of the video stream, which is displayed after the operator presses the stop video button on the HMI.

Image Capture

Figure 33:
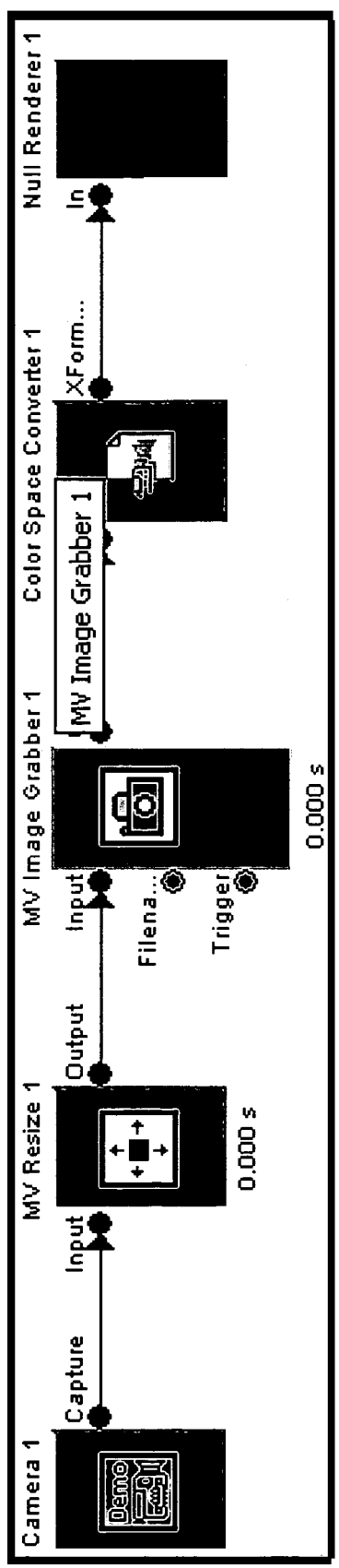

An image capture routine is shown in FIG. 33 and is used to capture snapshots of objects. Baseline shots or captures for a Live Differencing routine are captured using this function. Basically, this routine is identical to that described with respect to FIG. 31, except the Video Renderer function is replaced with a Null Renderer function, which terminates video that does not need to be displayed, but that cannot be left unterminated.

View File

Figure 34:
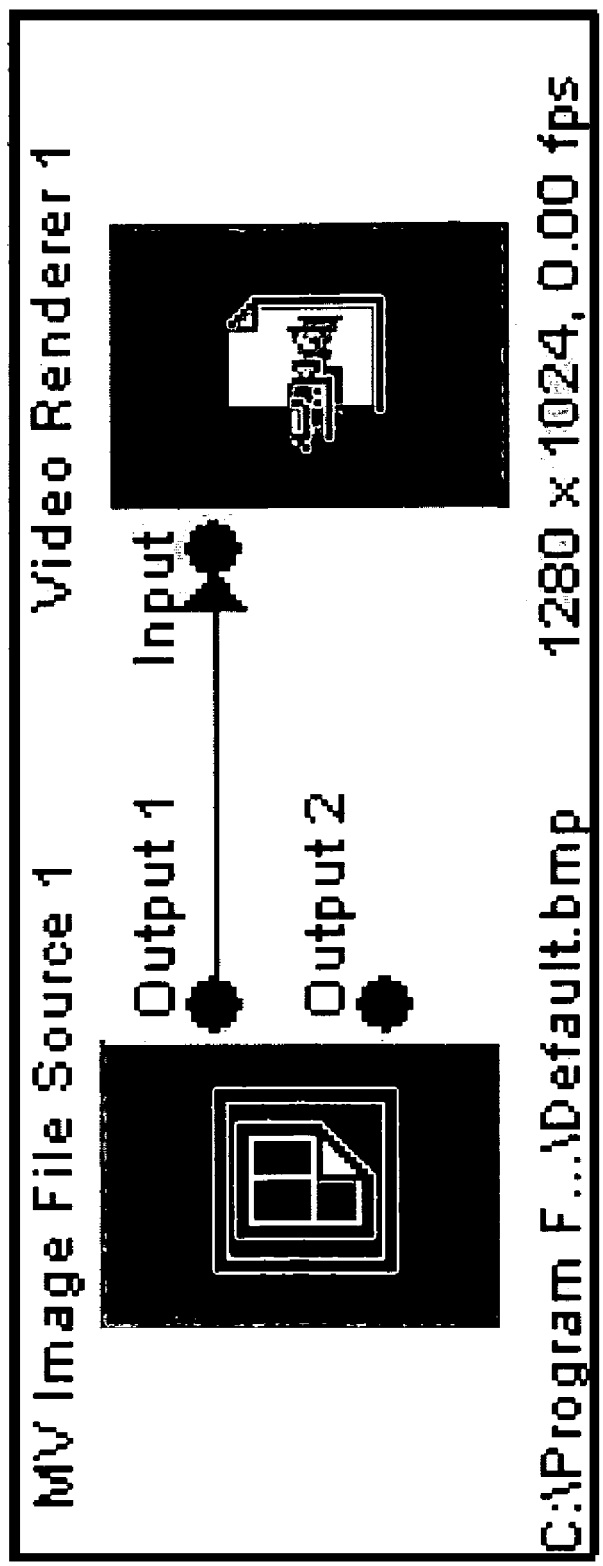
Figure 35:
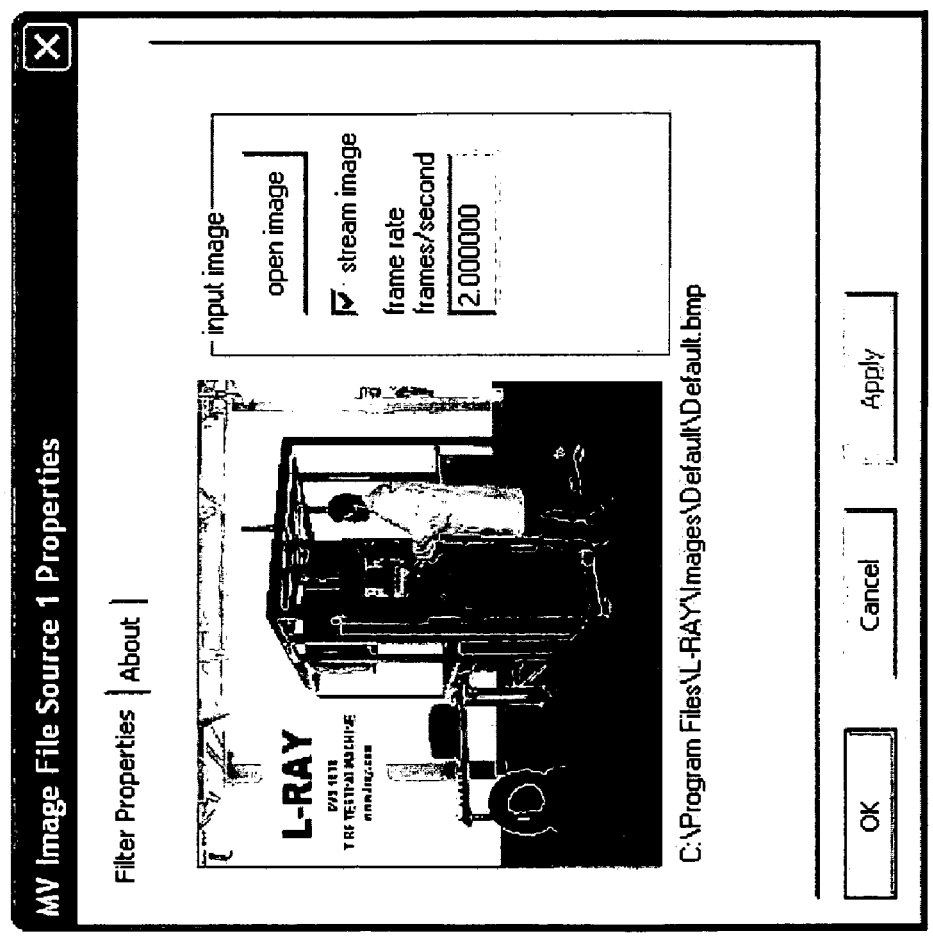

A view file routine is shown in FIG. 34 and is used to display processed still images, as opposed to the unprocessed live video, on the HMI. Here, an Image File Source function outputs to the Video Renderer discussed previously. The dialog box of FIG. 35 depicts the preferred property settings for the Image File Source.

Live Differencing

Figure 36:
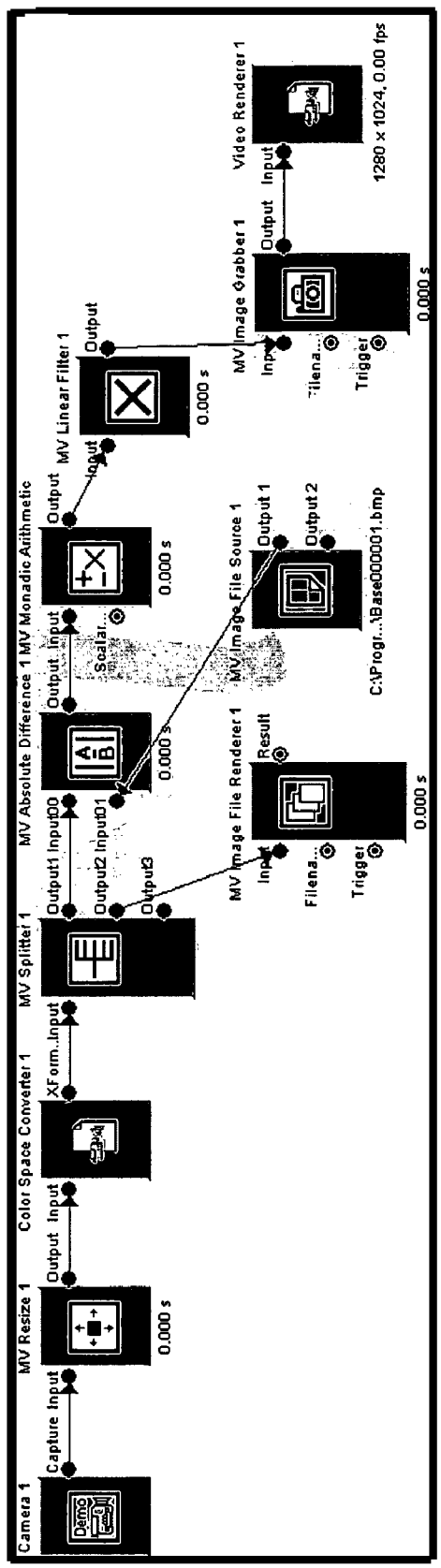

A live differencing routine is illustrated in FIG. 36, and is used to stream live differencing video on the HMI and to capture image stills that will be processed as cumulative differential images, as will be discussed in greater detail herein below. The first three steps or functions include the VideoSource camera capture, Resize, and Color Space Conversion functions discussed previously. The output from the Color Space Converter is fed to a Splitter function, which splits the video stream into multiple separate output video streams of the same content. One output video stream is an input to an Image File Renderer function and another output video stream is an input to an Absolute Difference function.

The Image File Renderer is used to create one or more single image files taken from the video stream, and supports the following file formats: Bitmap (*.bmp), JPEG (*.jpg), TIFF (*.tif) and PNG (*.png). Incoming images from the video stream can be saved to a directory or, the filter may use the trigger mode wherein an image file can be saved on each trigger event. The preferred output file properties are shown in the dialog box of FIG. 37.

The Absolute Difference function is a filter that accepts unprocessed video from the Splitter function and the saved image file from an Image File Source, and calculates the absolute values of the pixel differences of the two input images. The Image File Source function is used to output the saved or base image file to an input of an Absolute Difference function downstream of the Splitter function. The preferred properties are depicted in the dialog box of FIG. 38.

Figure 37:
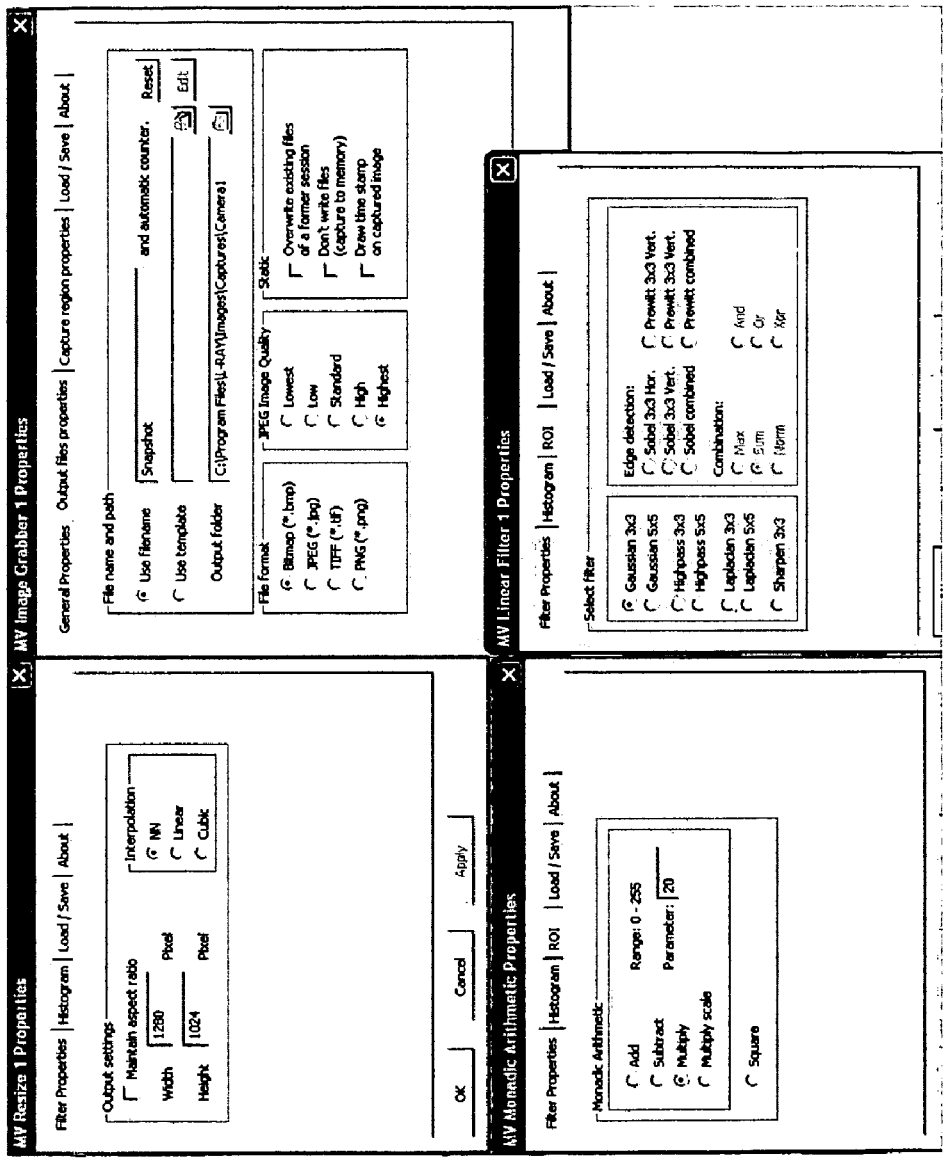
Figure 38:
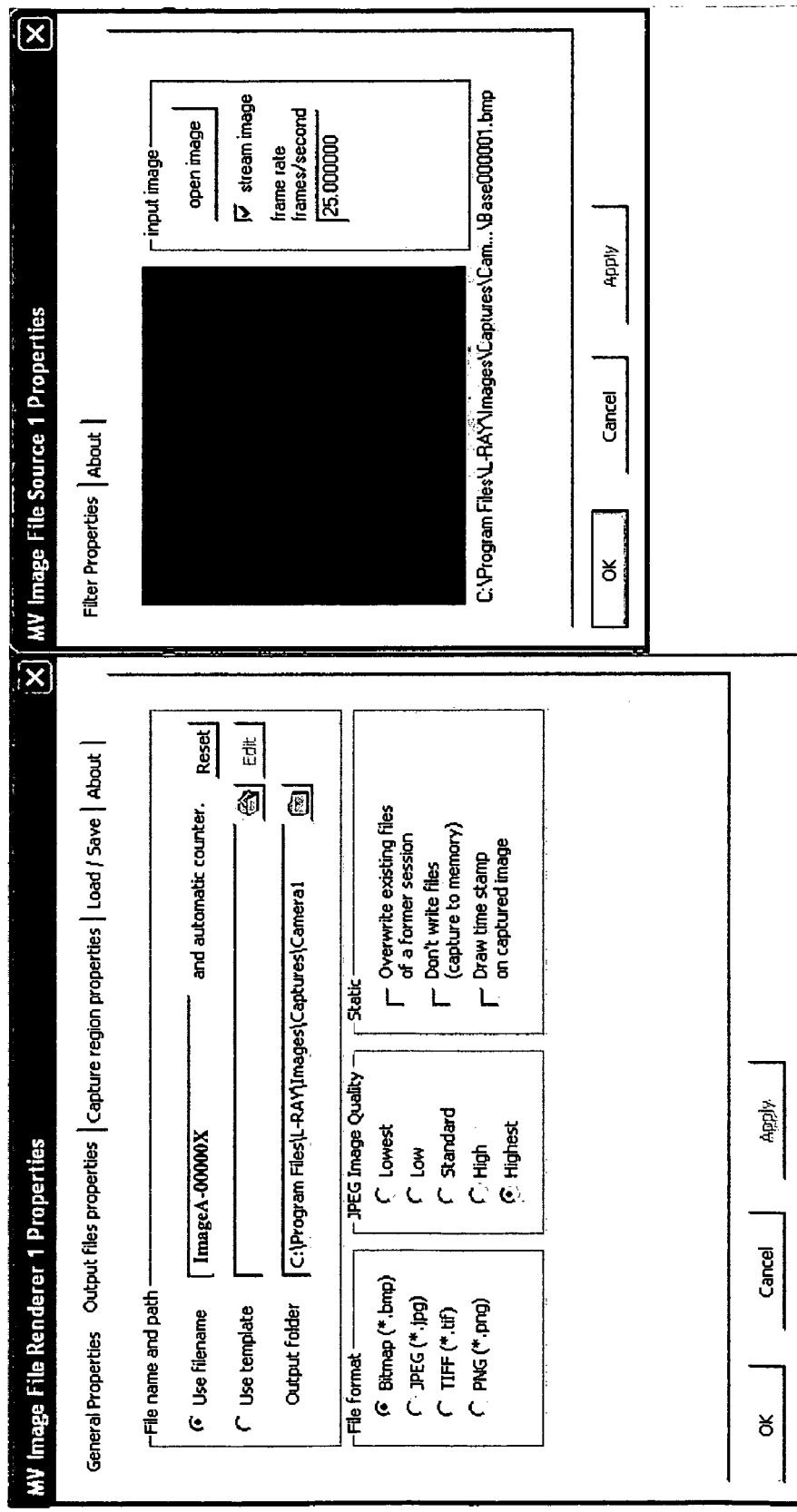

Output from the Absolute Difference function is accepted downstream by a Monadic Arithmetic filter that is used to modify pixel channels of a current image frame being processed using one of several arithmetic operations. As shown in FIG. 37 of the properties dialog, a multiply filter with a scalar of 20 is specified for application to the image. As an example, an addition operation using a scale value of 10 would increase all channel values of all pixels by 10, thereby providing a brighter resulting image wherein 0=black and 255=white.

Output from the Monadic Arithmetic function is accepted as input by a Linear Filter function, which convolves the frames of the current video stream using a predefined linear filter kernel. The filter supports several filter kernels and combinations of Sobel or Prewitt kernels including Gauss, High pass, Laplace, Sobel and Prewitt Matrices of sizes 3×3 or 5×5. The Linear Filter may thus provide edge detection, smoothing, Gaussian noise reduction, contrast enhancement, and the like. Preferred properties of the Linear Filter are depicted in the corresponding dialog box of FIG. 37.

Output from the Linear Filter function is accepted as input by an Image Grabber having the preferred output file properties depicted in the corresponding dialog box of FIG. 37. The output from the Image Grabber is communicated to the Video Renderer discussed previously.

Absolute Differencing

Figure 39:
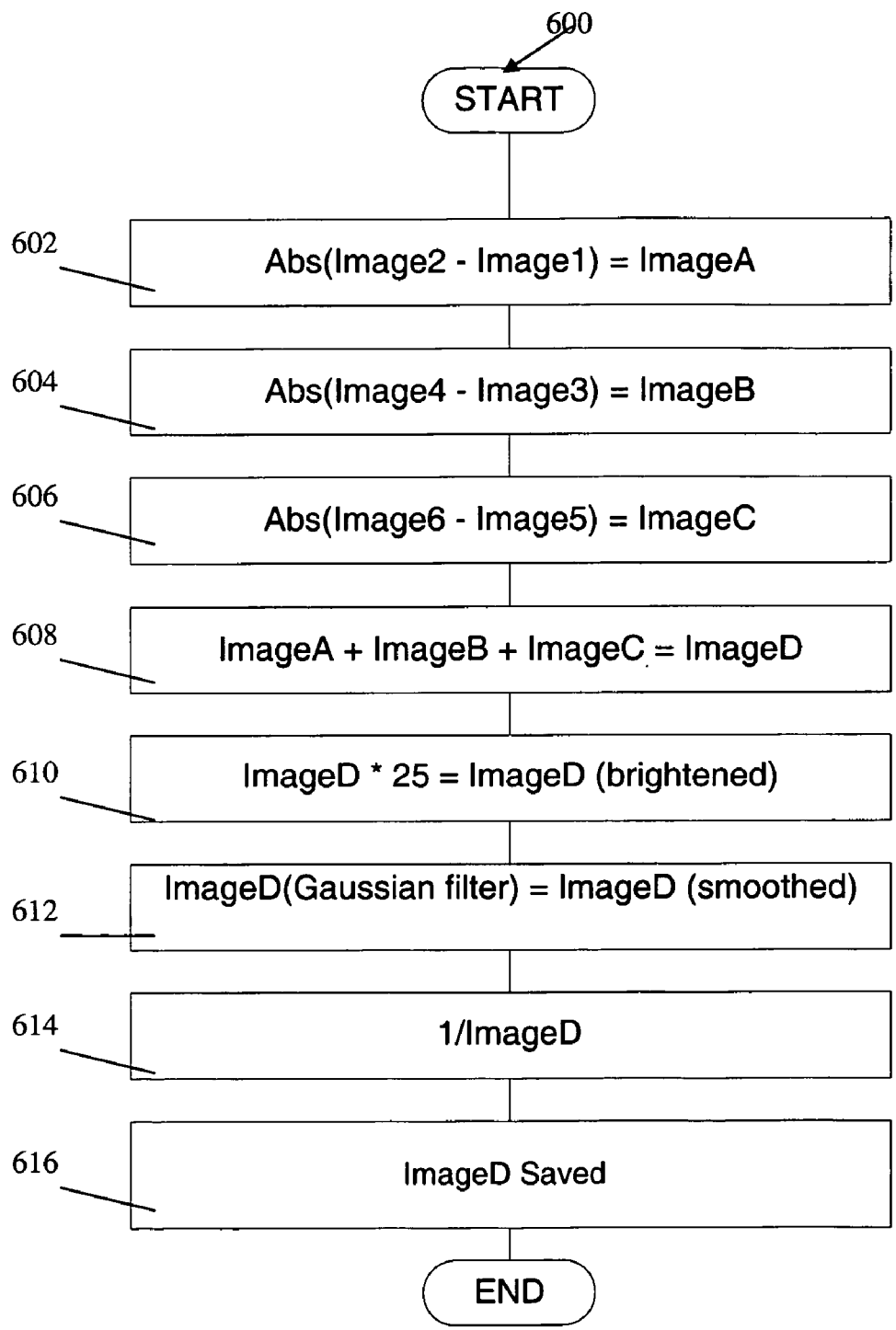
FIG. 39 is a flow chart of a preferred image differencing routine, preferably used with the production system of FIG. 9.

Referring now to the flow chart of FIG. 39, an absolute differencing routine 600 is illustrated and is preferably applied to all of the cameras over a preferred six predetermined test values. After completion of the various computer routines described above, at step 602 the pixel values of a first image, or image 1, of the preferred six images are digitally subtracted (i.e. absolute difference), pixel for corresponding pixel, from the pixel values of a second image, or image 2, of the preferred six images. The resultant differential is stored as image A. If image 1 is a baseline image captured while the object is unstressed or subjected to a "zero" value test level, then image 1 will likely be substantially relatively dark, i.e. registering pixel values closer to 0 than to 255 on the grayscale. If image 2 is an image captured while the object is stressed to some non-zero test level value, then image 2 will exhibit some relatively light areas in the presence of anomalies, registering pixel values progressively away from 0. Again, at step 604, the pixel values of image 3 are digitally subtracted (i.e. absolute difference), pixel for corresponding pixel, from the pixel values of image 4. The resultant differential is stored as image B. Likewise, at step 606, the pixel values of image 5 are digitally subtracted (i.e. absolute difference), pixel for corresponding pixel, from the pixel values of image 6. The resultant differential is stored as image C. Basically, this routine results in differential images A, B, and C that are essentially "spaced" apart from one another along the range of test levels.

Figure 40:
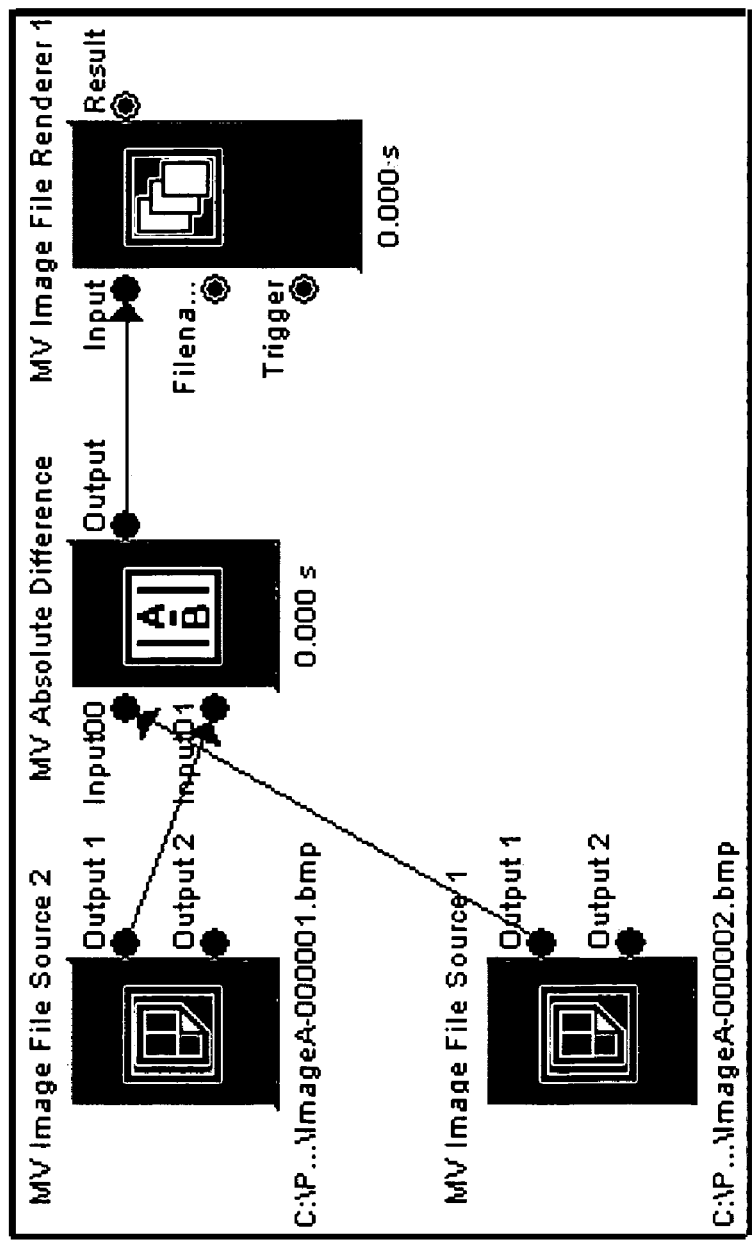
FIGS. 40 through 44 are graphical user interface screen shots that illustrate additional functionality of the image processing software of FIG. 12.
Figure 41:
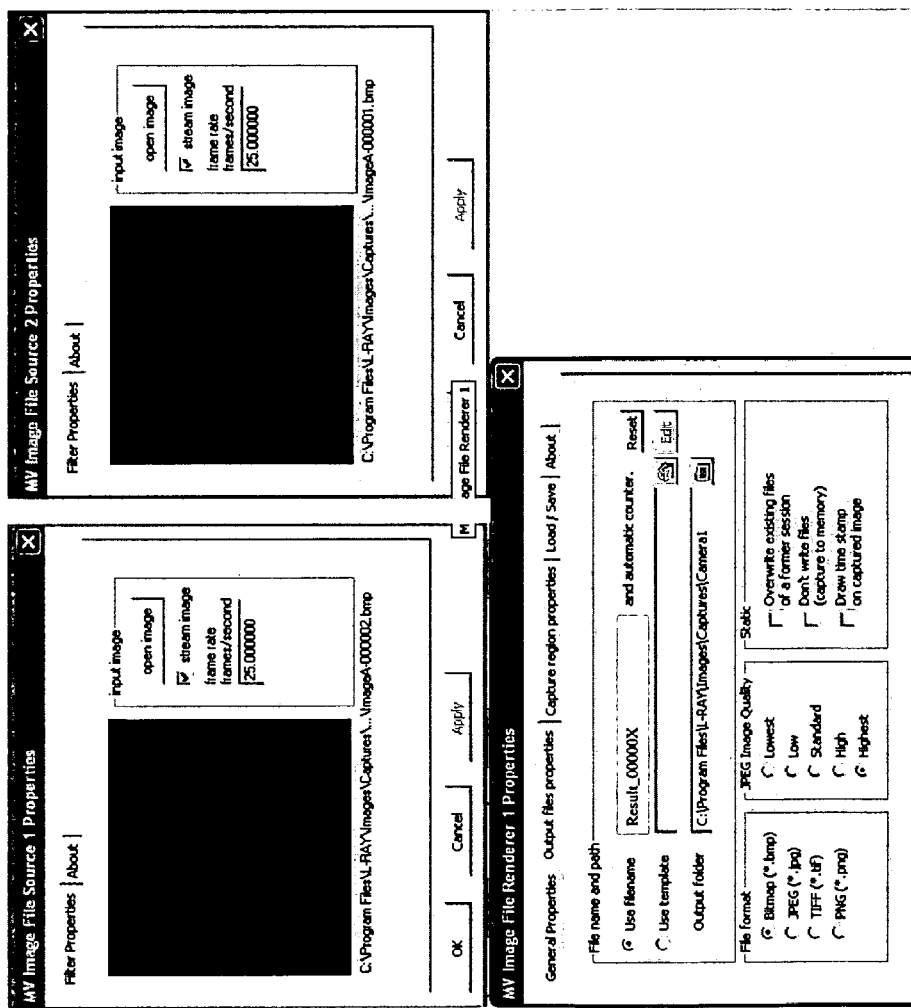

Steps 602 through 606 are preferably carried out using an Absolute Difference routine of MontiVision that is depicted by the MontiVision screen shot of FIG. 40. FIG. 40 depicts an Absolute Difference function of the first of the several pairs of images, and corresponds directly to step 602. Here, an Absolute Difference function accepts output from 1) an "Image File Source 1" function that presents a second image of a pair of images saved according to the Source 1 filter properties dialog of FIG. 41, and from 2) an "Image File Source 2" function that presents a preceding first image of the pair of images saved according to the Image File Source 2 filter properties dialog box of FIG. 41. The Absolute Difference filter accepts the images from the saved image files of the Image File Sources, and calculates the absolute values of the pixel differences of the two input images, which output is accepted as input to the Image File Renderer discussed previously and whose preferred output filter properties are depicted in the corresponding dialog of FIG. 41, including the file name "Result". Moreover, FIG. 40 is also exemplary of steps 604 and 606. Those of ordinary skill in the art will recognize that the absolute differencing routine may contain more or less than the steps described herein to produce an absolute differenced image, and that the filenames are arbitrary and may be different from those used herein.

Alternative Absolute Differencing

Figure 39A:
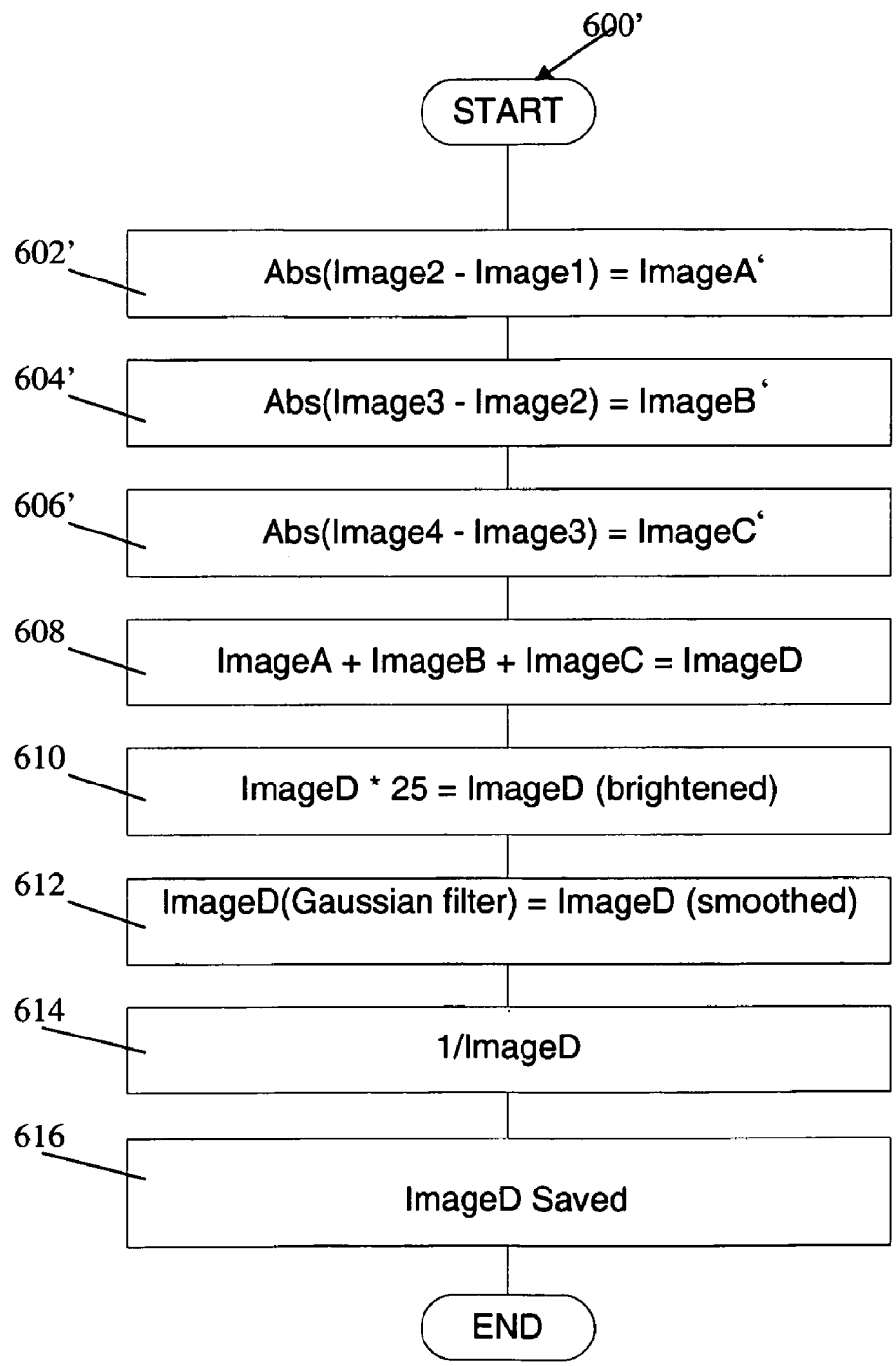
FIG. 39A is a flow chart of an alternative image differencing routine, preferably used with the production system of FIG. 9.

Referring now to the flow chart of FIG. 39A, an alternative absolute differencing routine 600' is illustrated and is preferably applied to all of the cameras over four, instead of six, predetermined test values. At step 602' the pixel values of a first image, or image 1, of the four images are digitally subtracted, pixel for corresponding pixel, from the pixel values of a second image, or image 2, of the four images. The resultant differential is stored as image A'. At step 604', the pixel values of image 2 are digitally subtracted, pixel for corresponding pixel, from the pixel values of a third image, or image 3, of the four images. The resultant differential is stored as image B'. Likewise, at step 606', the pixel values of image 3 are digitally subtracted, pixel for corresponding pixel, from the pixel values of a fourth image, or image 4, of the four images. The resultant differential is stored as image C'. Basically, this routine results in differential images A', B', and C'that are essentially "adjacent" one another along the range of test levels.

Cumulative Differential Imaging

Referring to the flow charts of FIGS. 39 and 39A, at step 608 the pixel values of the differential images (images A, B, and C or A', B', and C') are added, pixel for corresponding pixel, to produce a raw cumulative differential image (CDI) shown as image D or D'. This step, among other things, effectively integrates or stacks the appearance of anomalies from different portions of the test range, because some anomalies may appear in one portion of a test range, but not another. The nature of non-destructive testing in general, and in deformation specifically, is such that some anomalies may appear over certain portions of the test range and disappear over others. Accordingly, stacking the images to provide the raw CDI yields one comprehensive, "show-all" image for analyzing quality of the test object.

Figure 42:
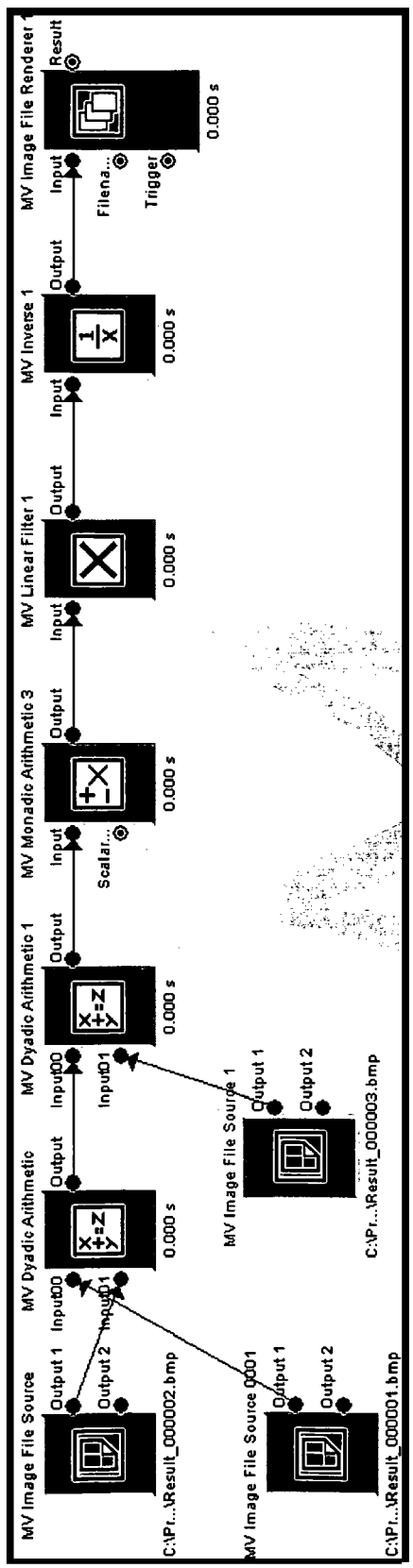
Figure 43:
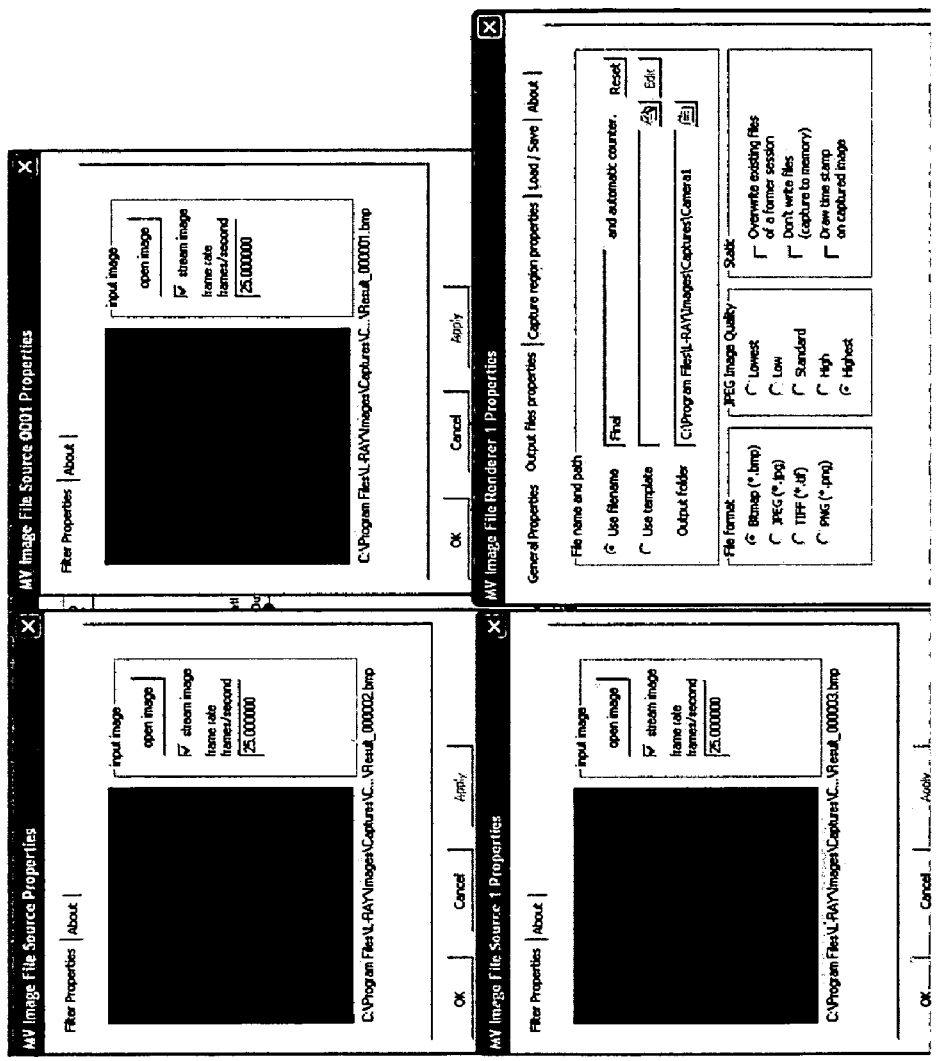
Figure 44:
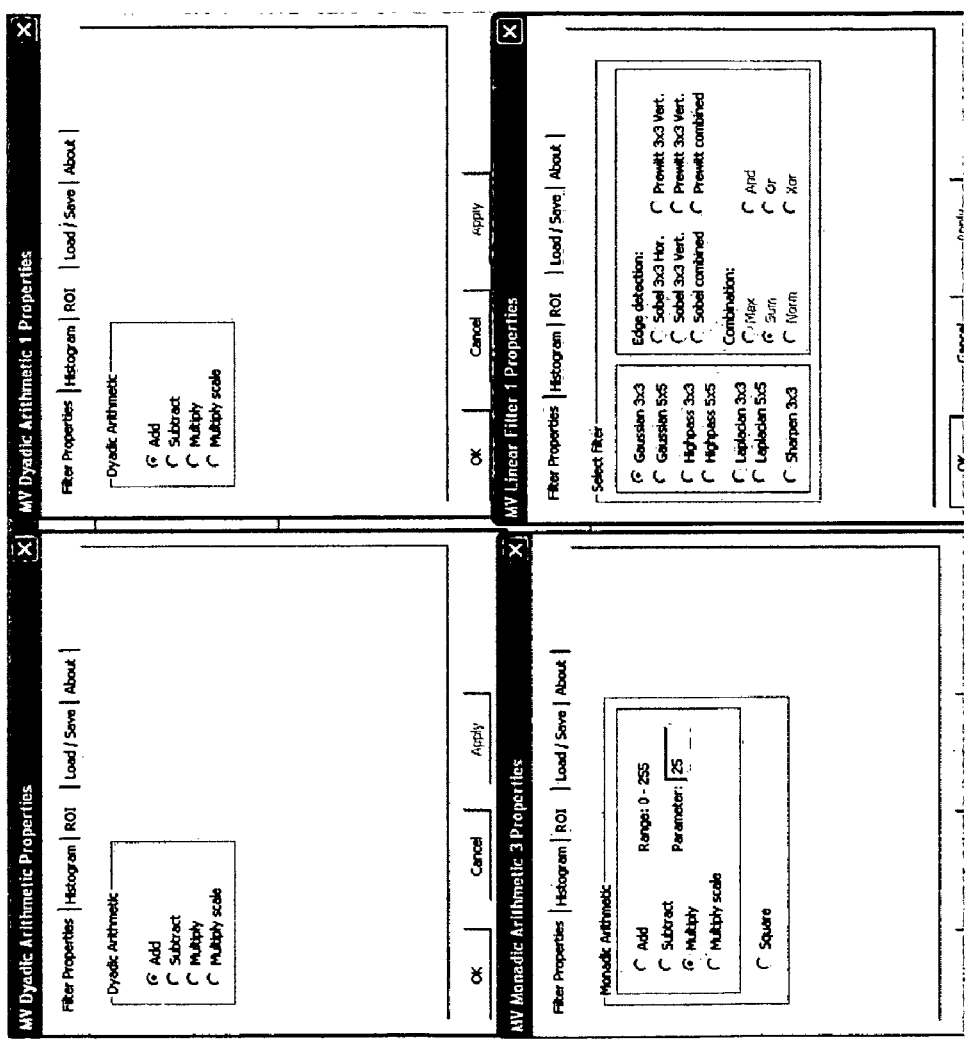

FIG. 42 depicts the cumulative differential step 608 of FIG. 39, preferably automatically carried out by MontiVision. A first Dyadic Arithmetic function accepts input from 1) an "Image File Source 0001", which includes the preferred file source properties in the corresponding dialog of FIG. 43 and which corresponds to image A of the flow chart of FIG. 39, and from 2) an "Image File Source", which includes the preferred file source properties in the corresponding dialog of FIG. 43 which corresponds to image B of the flow chart of FIG. 39. The Dyadic Arithmetic filter property dialog of FIG. 34 shows that the operation is addition. A second Dyadic Arithmetic function accepts output from 1) the first Dyadic Arithmetic operation and from 2) an "Image File Source 1", which includes the preferred file source properties of the corresponding dialog of FIG. 43 which corresponds to image C of the flow chart of FIG. 39. The Dyadic Arithmetic 1 filter property dialog of FIG. 44 shows that the operation is addition.

Referring again to FIG. 39, the raw CDI is preferably further processed, wherein the three sets of differenced pairs are added together, brightened, smoothed, and inverted, to produce a resultant CDI that renders anomalies more visible to the human eye. Accordingly, in step 610, the raw CDI is brightened so as to be visible to the human eye. In other words, the pixel values of the raw CDI are increased. In step 612, the now brightened CDI is smoothed to reduce graininess or noise and otherwise increase image aesthetics. In step 614, the brightened and smoothed CDI is inverted so as to show relatively dark anomalies against a relatively lighter non-anomalous background of the object. As used herein, the term "invert" means that the pixel values are adjusted such that a 0 pixel value becomes a 255 pixel value, vice-versa, and a 1 pixel value becomes a 254 pixel value, vice-versa, and so-on. In other words, to "invert" an image means to make a "negative" of the image.

FIG. 42 corresponds to steps 608 through 614 of FIG. 39 and the steps therein are preferably used to produce the resultant CDI from the preferably three sets of differenced pairs. A Monadic Arithmetic operation is performed on the output from the second Dyadic Arithmetic function so as to multiply the output by a preferred scalar of 25 to "brighten" the image. Then, a Gaussian 3×3 linear filter is preferably applied to the output from the Monadic Arithmetic function as shown by the Linear Filter 1 function and its corresponding filter properties dialog of FIG. 44 to "smooth" the image. The output from the Linear Filter is then inverted in grayscale as shown by the Inverse function. Finally, the inverted image is accepted as input to the Image File Renderer discussed previously and whose preferred output filter properties are depicted in the corresponding dialog of FIG. 43, including the exemplary file name Final. The output is a final or resultant CDI, with relatively dark anomalies against a relatively light non-anomalous background. Those of ordinary skill in the art will recognize that the CDI routine may contain more or less than the steps described herein to produce a CDI and/or resultant CDI.

Enhanced CDI

Figure 45:
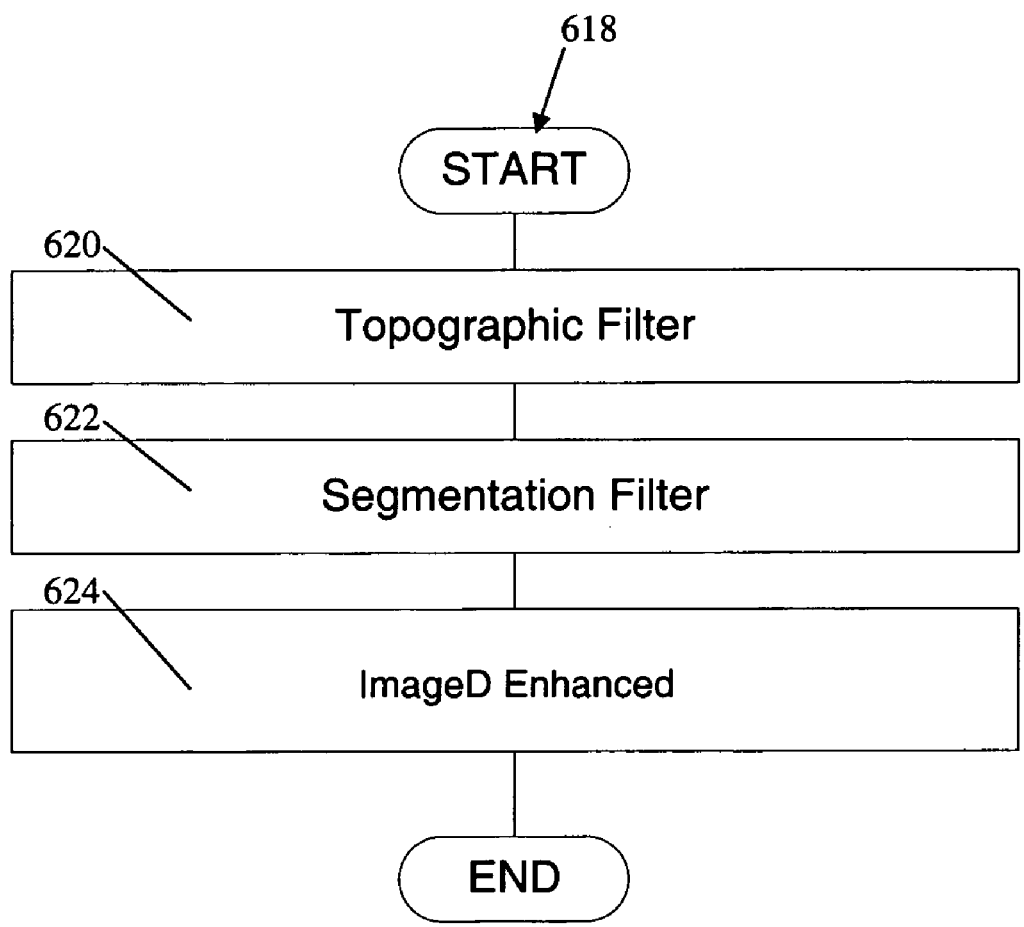
FIG. 45 is a flow chart of a preferred image enhancement routine, preferably used with the production system of FIG. 9.

Referring now to the flow chart of FIG. 45, once the resultant CDI has been produced it may be desirable to further improve the visual appearance of the resultant CDI by applying an enhancement routine 618. As shown, one or both of a Topography filter function 620 and a Segmentation filter function 622 are applied to the resultant CDI.

Figure 46:
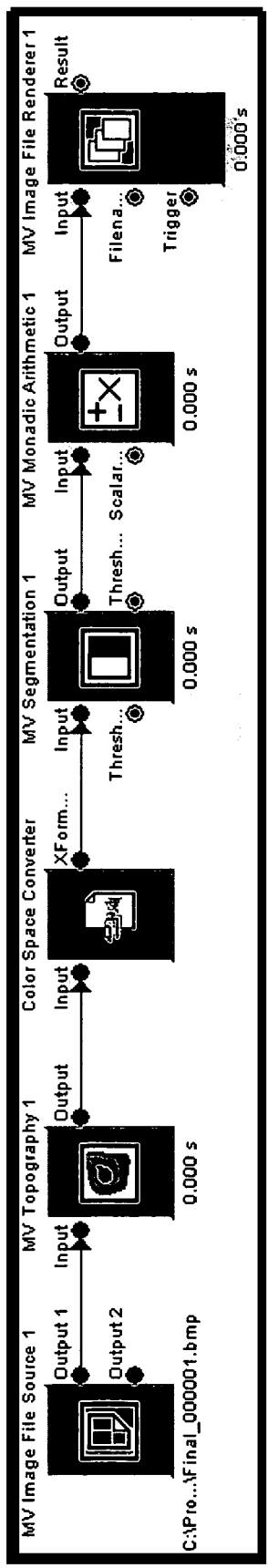
FIGS. 46 through 48 are graphical user interface screen shots that illustrate preferred details of the image enhancement routine of FIG. 45.

The enhancement routine is also depicted in the MontiVision screen shot of FIG. 46. An Image File Source function is used to access the automatically generated "Final" file from the previously described CDI routine and displays the object image as having black or dark anomalies against a relatively light or grey background, as shown in the properties dialog box of FIG. 47.

Figure 47:
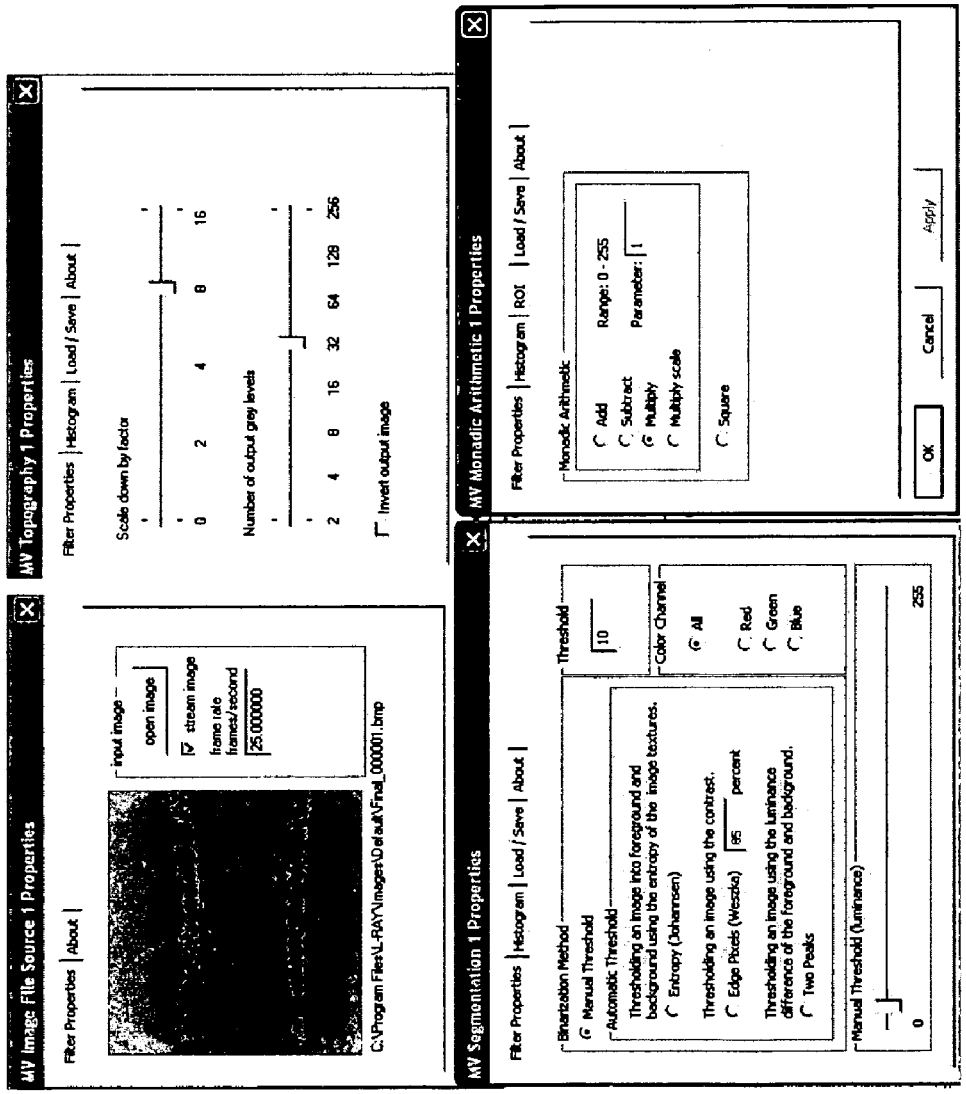

Next, the Topography filter automatically generates a topography map from the current video frame received from the Image File Source so as to limit the number of output grey (or color) levels. In other words, topographically filtering means to selectively filter out certain grayscale (or colorscale) image gradations to effectively reduce image noise and present a clearer image. Using the Topography filter, the resultant CDI video frame is preferably downsampled and upsampled using a gaussian 5×5 filter kernel up to a factor of 16 as shown in FIG. 47. The topographically filtered output goes to an input of a Color Space Converter, as described previously, to convert between different color spaces and thereby connect different MontiVision modules that do not support each other's color space. In this case, the Color Space Converter output connects to a Segmentation filter used for image segmentation.

Segmentation is basically an automatic conversion from grayscale to black and white, and is a preferred pre-processing step for a downstream automatic blob detection function. As shown in the properties dialog box of FIG. 47, manual thresholding is chosen, for example, at a value of 10, and all color channels are specified for the segmentation. Those of ordinary skill in the art will recognize that the particular settings and values chosen herein may be varied and adjusted depending upon the particular application involved. After the image is segmented, it is processed by a Monadic Arithmetic filter that is used to modify pixel channels of the current image frame being processed using one of several arithmetic operations. As shown in FIG. 47 of the properties dialog, a multiply filter with a scalar of 1 is specified for application to the image.

Figure 48:
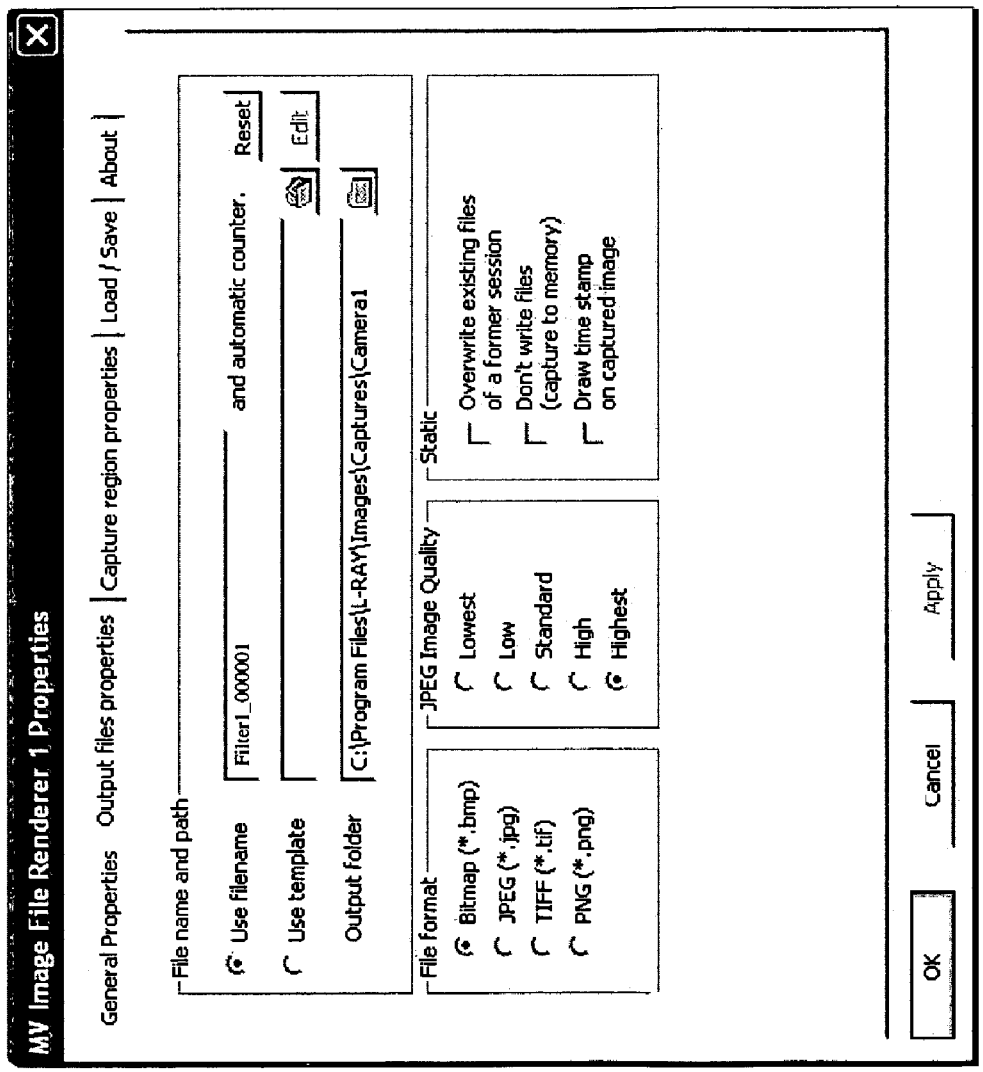

Finally, the output from the Monadic step is saved using an Image File Render function specifying a default file name of "Capture" as shown in the properties dialog of FIG. 48. Those of ordinary skill in the art will recognize that the enhanced CDI routine may contain more or less than the steps described herein to produce an enhanced CDI.

Analyzed CDI

Figure 49:
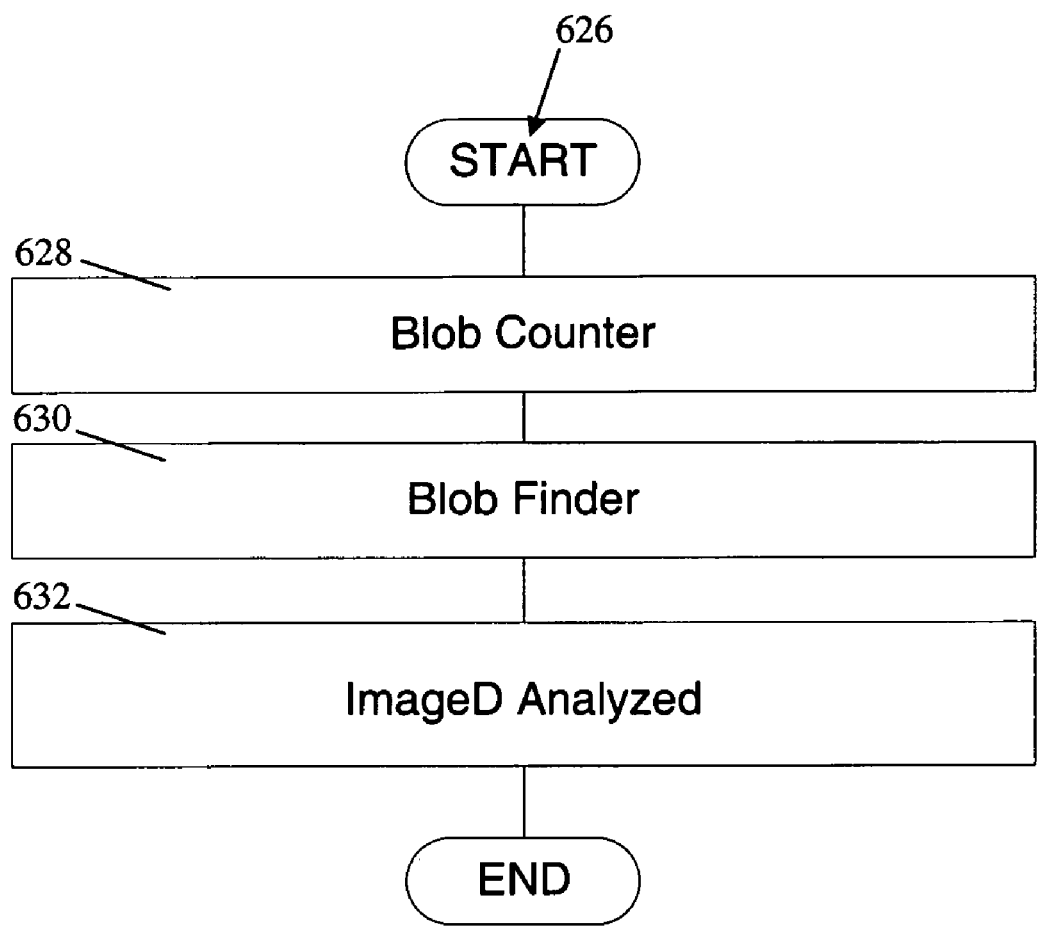
FIG. 49 is a flow chart of a preferred image analysis routine, preferably used with the production system of FIG. 9.

Referring now to the flow chart of FIG. 49, once the now enhanced CDI has been produced it may be desirable to analyze the enhanced CDI by applying an analysis routine 626 to effectively identify and quantify anomalies in the enhanced CDI to produce an analyzed CDI. As shown, one or both of an automatic Blob Counter function 628 and an automatic Blob Finder function 630 are applied to the enhanced CDI from the previously described enhancement routine.

Figure 50:
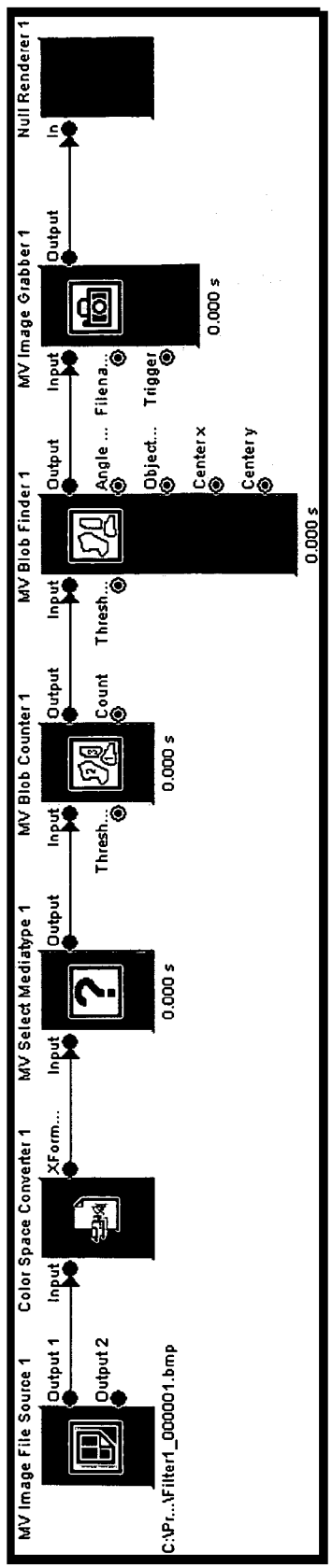
FIGS. 50 through 54 are graphical user interface screen shots that illustrate preferred details of the analysis routine of FIG. 49.
Figure 51:
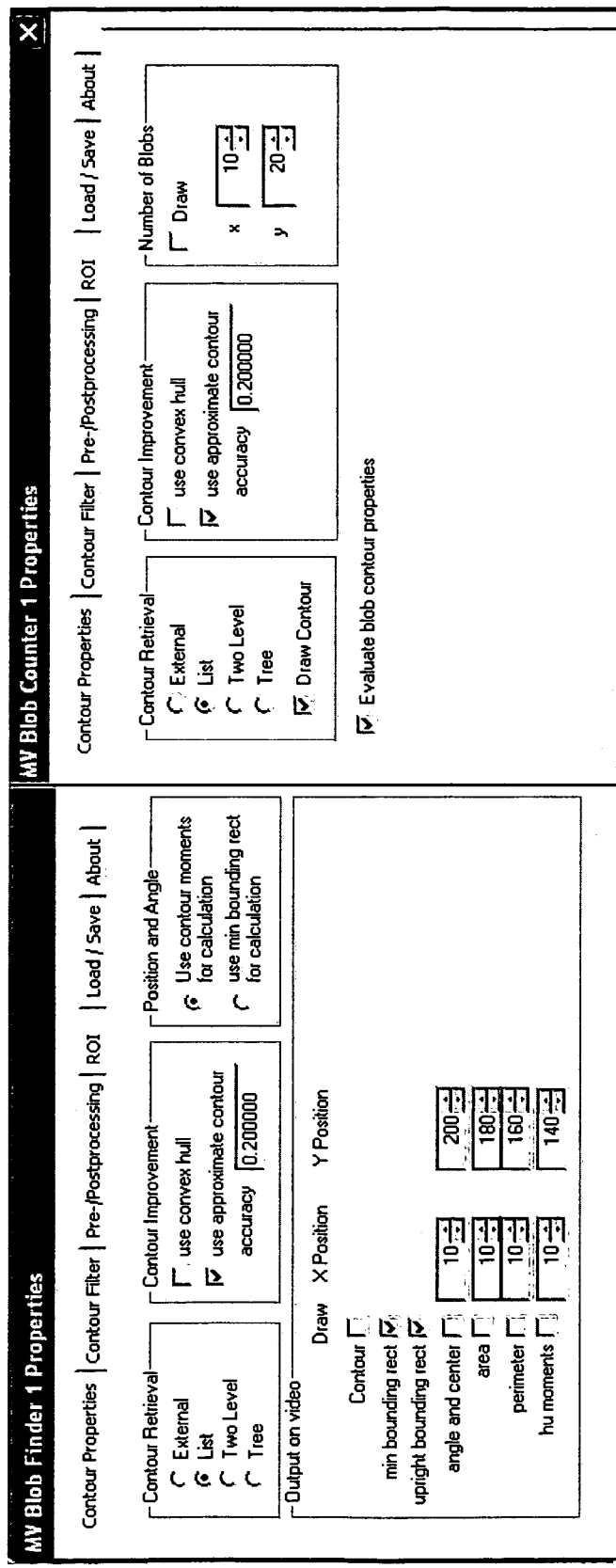
Figure 52:
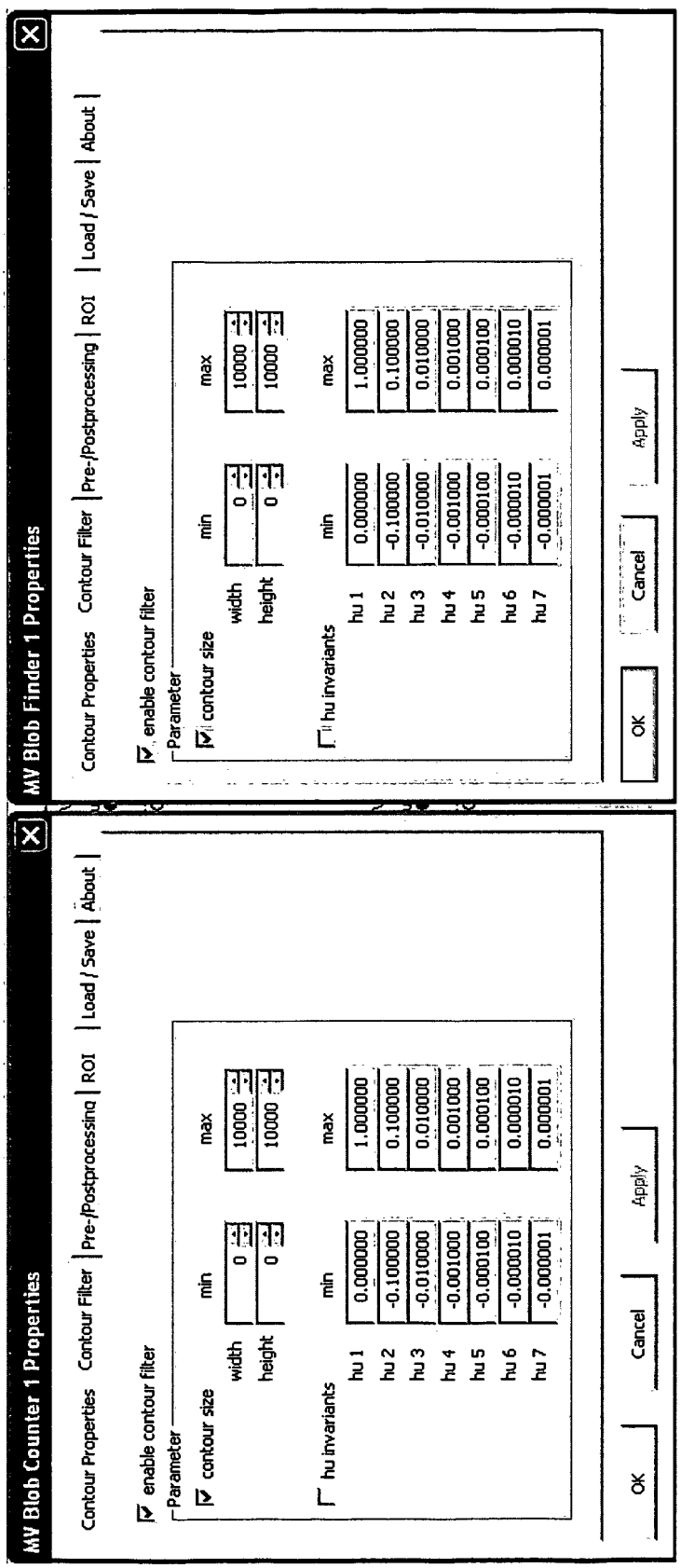
Figure 53:
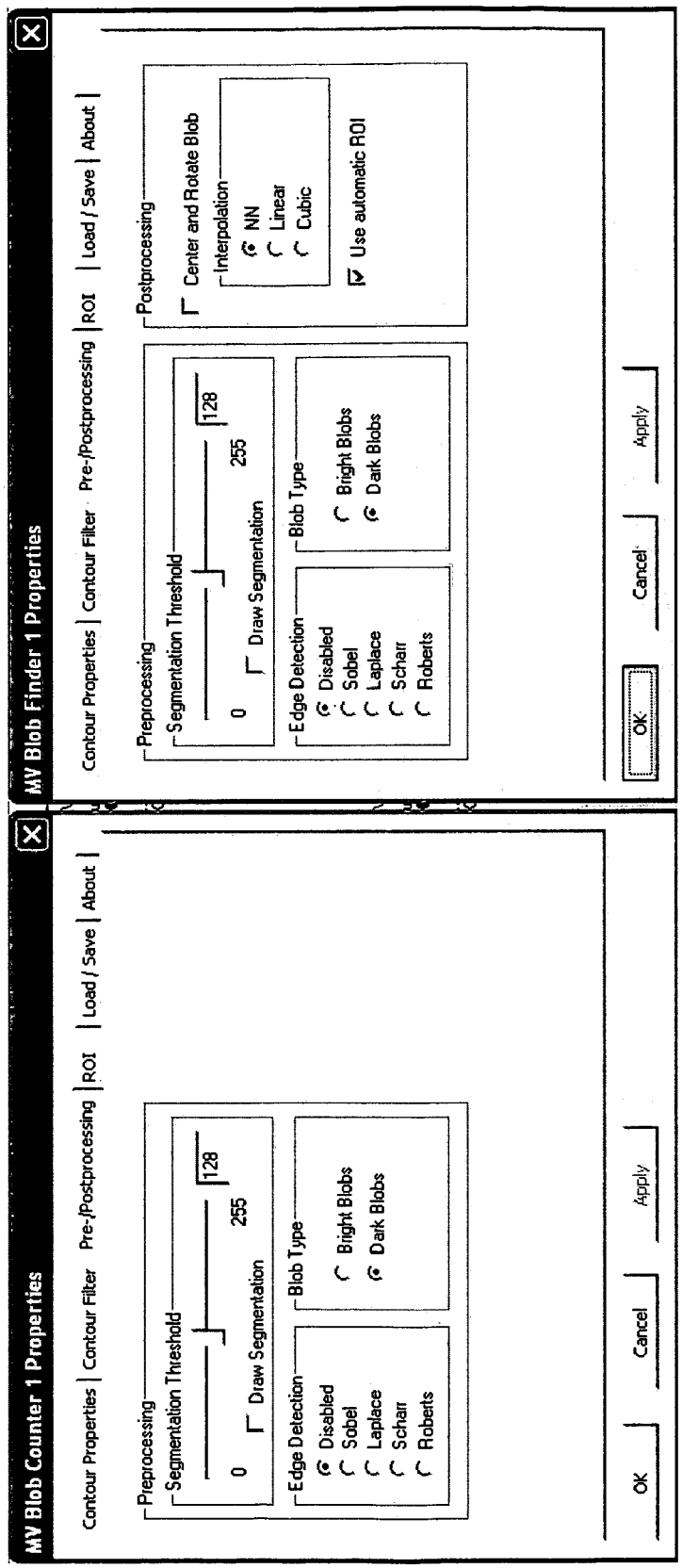

The analysis routine is also depicted in the MontiVision screen shot of FIG. 50. An Image File Source function is called to output the previously enhanced CDI, which is saved with an exemplary file name of Filter1_00000.bmp. A Color Space Converter converts the enhanced image for use by a downstream tool, Select Mediatype, which determines the type of media that should be used for a filter connection to a downstream Blob Counter. The Select Mediatype is not a video transformation filter, but rather, is used to set a connection between two filters to a specific media type, e.g. RGB 24, YUV, or the like. Many filter functions may support more than one media type as inputs and outputs. When two relatively upstream filters are connected, they use the first media type that is acceptable by, or common to, both filters. But sometimes that common media type is not compatible for other downstream filters, such as the downstream Blob Counter in this situation. In this case, the Select Mediatype filter is used to set the connection to the right media type. The Select Mediatype filter is transparent for all stream data and transports the data with a minimum delay, without loss of performance.

The Blob Counter is basically a filter to automatically detect and to count all blobs within a given image or video stream. The blobs are representative of anomalies of the tested object and may, for example, be black or dark objects or contours against a white or light background, or vice-versa. One filter excludes all blobs outside a minimum and maximum size, and the second filter excludes all blobs whose seven "hu invariants" are outside minimum and maximum values. Hu invariants are basically invariants to the scale, rotation, and reflection of an image, except for the seventh hu invariant, whose sign is changed by reflection. As shown in the Blob Counter properties dialog box of FIG. 51, the "list" contour retrieval is chosen to arrange all blobs in one list and contour drawing is enabled, an approximate contour accuracy of 0.2 is chosen for contour improvement to reduce contour complexity, and blob contour properties evaluation is enabled. As shown in the contour filter tab of the Blob Counter properties dialog of FIG. 52, the contour filtering is enabled wherein contour sizes of between 0 and 10,000 pixels in width and height are selected. As also shown in the pre-/postprocessing tab of the Blob Counter properties dialog of FIG. 53, preprocessing segmentation threshold of 128 of 255 is specified. Also edge detection is disabled and only dark blobs are to be found.

Referring again to FIG. 50, the output of the Blob Counter is accepted as input by a Blob Finder filter, which automatically calculates one or more blob characteristics such as orientation or angle, perimeter, area, minimum bounding rectangle, upright bounding rectangle, spatial and central moments, and hu invariants. Additionally, the Blob Finder filter may calculate a convex hull for the blob or reduces contour complexity with an approximation routine. The Blob Counter and Finder are preferably used together to optimize blob analysis. As shown in the properties dialog box of FIG. 51, the "list" contour retrieval is chosen, an approximate contour accuracy of 0.2 is chosen for contour improvement, contour moments are used as a base for calculation of position and orientation or angle, and the video output includes a minimum bounding rectangle and an upright bounding rectangle. As also shown in the contour filter tab of the Blob Finder properties dialog box, the contour filtering is enabled wherein contour sizes of, for example, between 0 and 10,000 pixels in width and height are selected. As also shown in the pre-/postprocessing tab of the Blob Counter properties dialog of FIG. 53, preprocessing segmentation threshold of 128 of 255 is specified. Also edge detection is disabled and only dark blobs are to be found and automatic region of interest (ROI) is selected for postprocessing.

Figure 54:
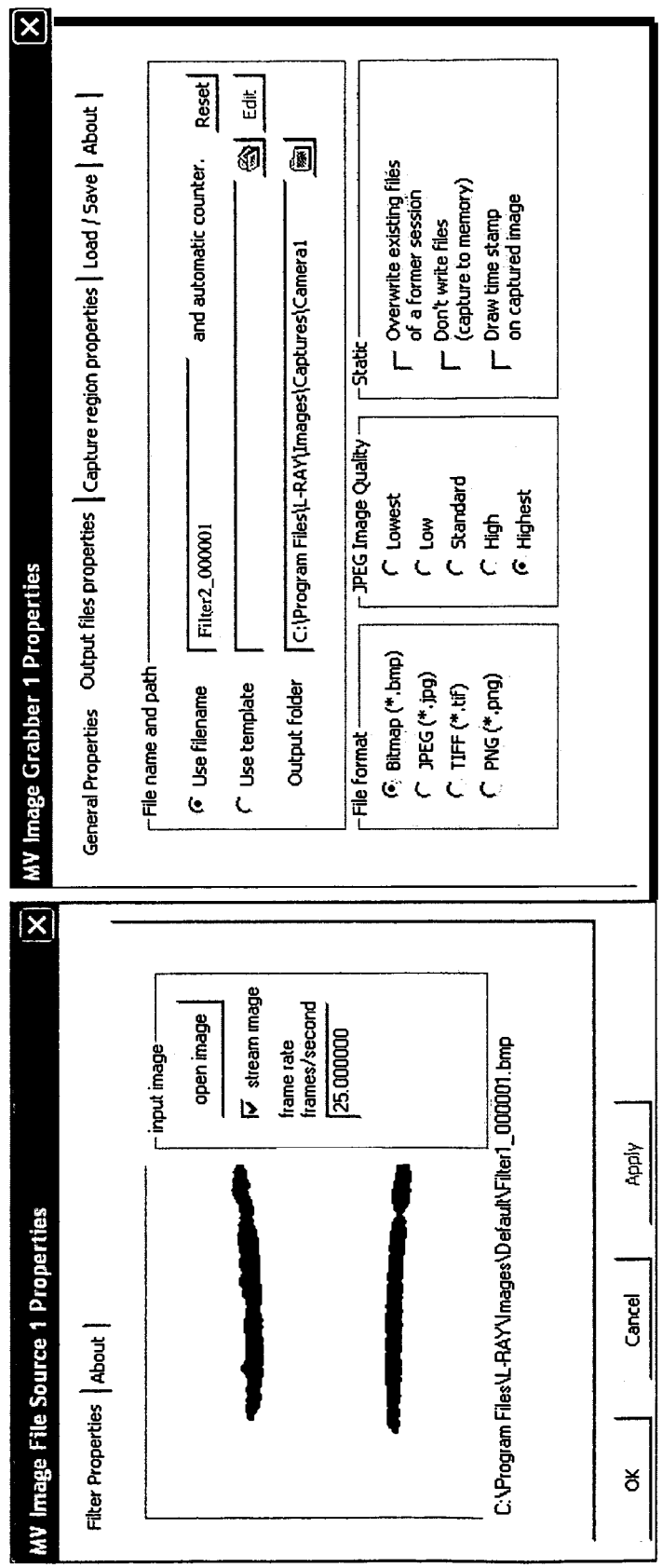

Referring again to FIG. 50, an Image Grabber function is called to accept output from the Blob Finder to capture a snapshot output in a bitmap (*.bmp) format with a file name of "Filter2_000001" as shown in FIG. 54, which depicts the preferred file properties of the image grabber. Finally, a Null Renderer function is called to terminate imagery that does not need to be displayed, but that cannot be left unterminated. Those of ordinary skill in the art will recognize that the analyzed CDI routine may contain more or less than the steps described herein to produce an analyzed CDI.

Overlaid CDI

Figure 55:
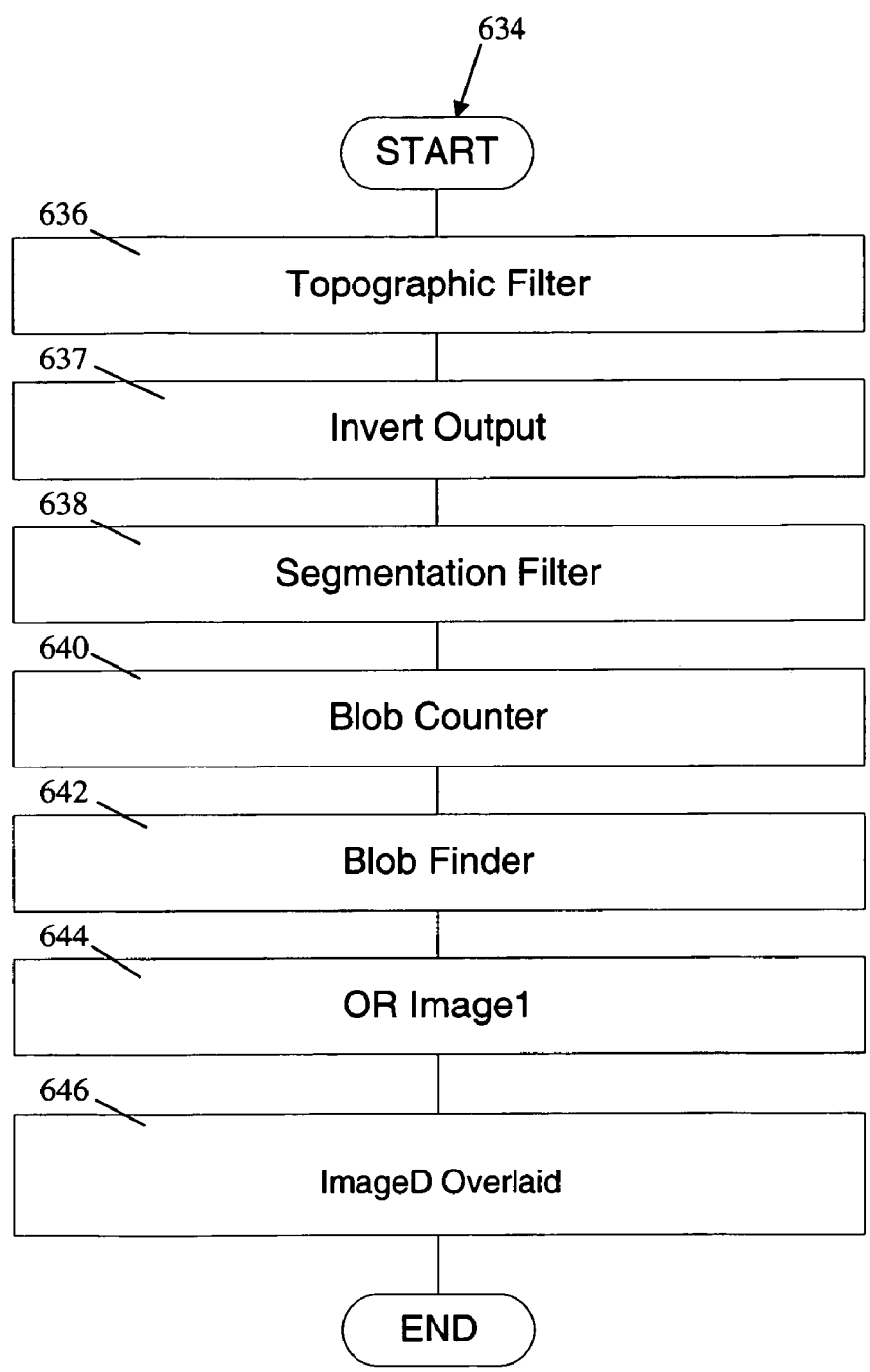
FIG. 55 is a flow chart of a preferred image overlay routine, preferably used with the production system of FIG. 9.
Figure 56:
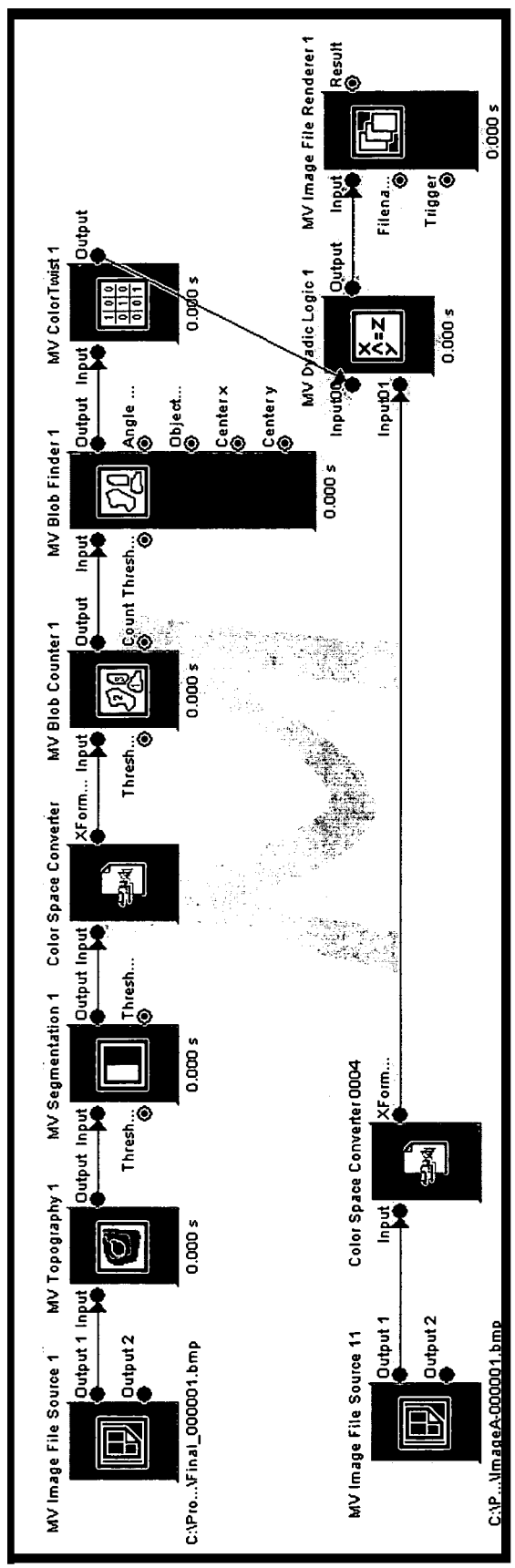
FIGS. 56 through 62 are graphical user interface screen shots that illustrate preferred details of the image overlay routine of FIG. 55.

Referring now to the flow chart of FIG. 55, once the resultant CDI has been produced it may be desirable to further improve the visual appearance of the resultant CDI by applying an overlay routine 634, wherein the resultant CDI is enhanced and analyzed and then overlaid on a baseline image of the test object to illustrate where the anomalies are in relation to the baseline image of the test object. The routine 634 includes similar steps as previously discussed with regard to FIGS. 45 through 54, with a few exceptions to enable a clear overlay of the enhanced and analyzed image over a baseline image. FIG. 56 is a MontiVision screen shot that corresponds to the flow chart of FIG. 55.

Figure 57:
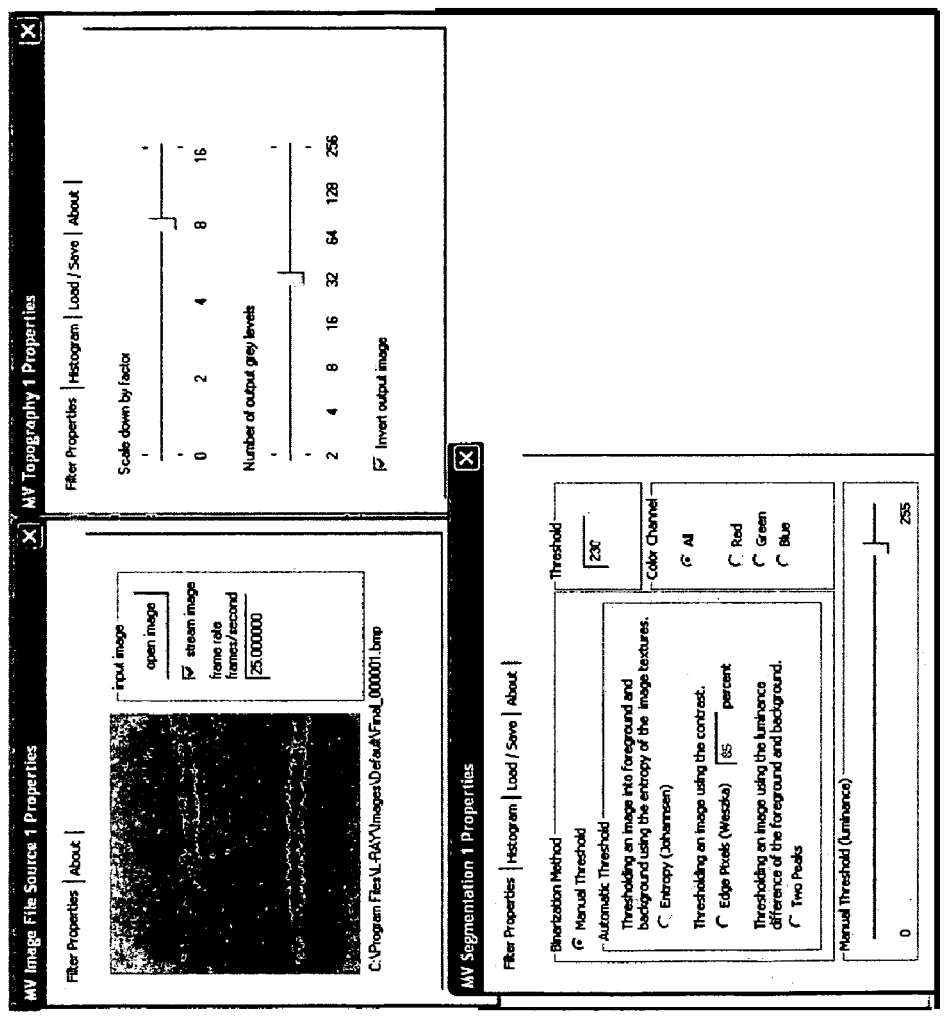
Figure 58:
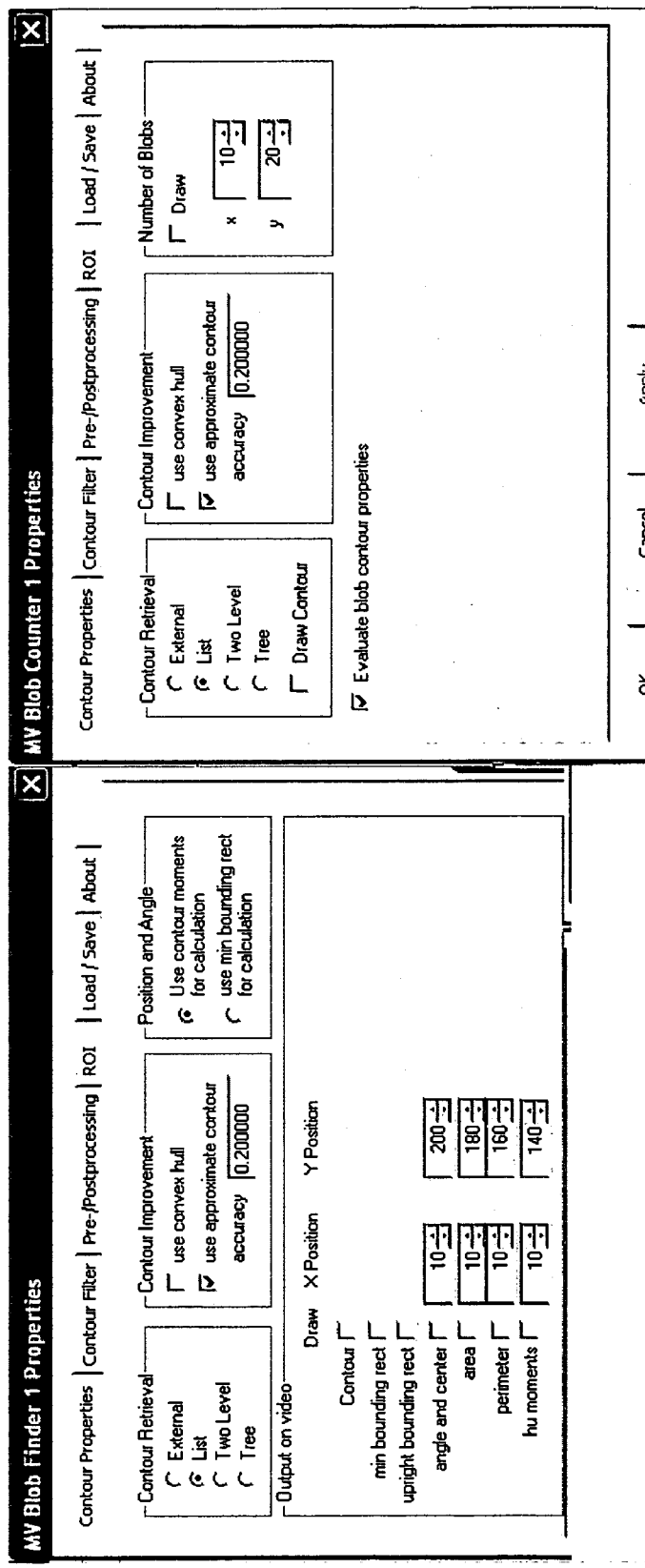
Figure 59:
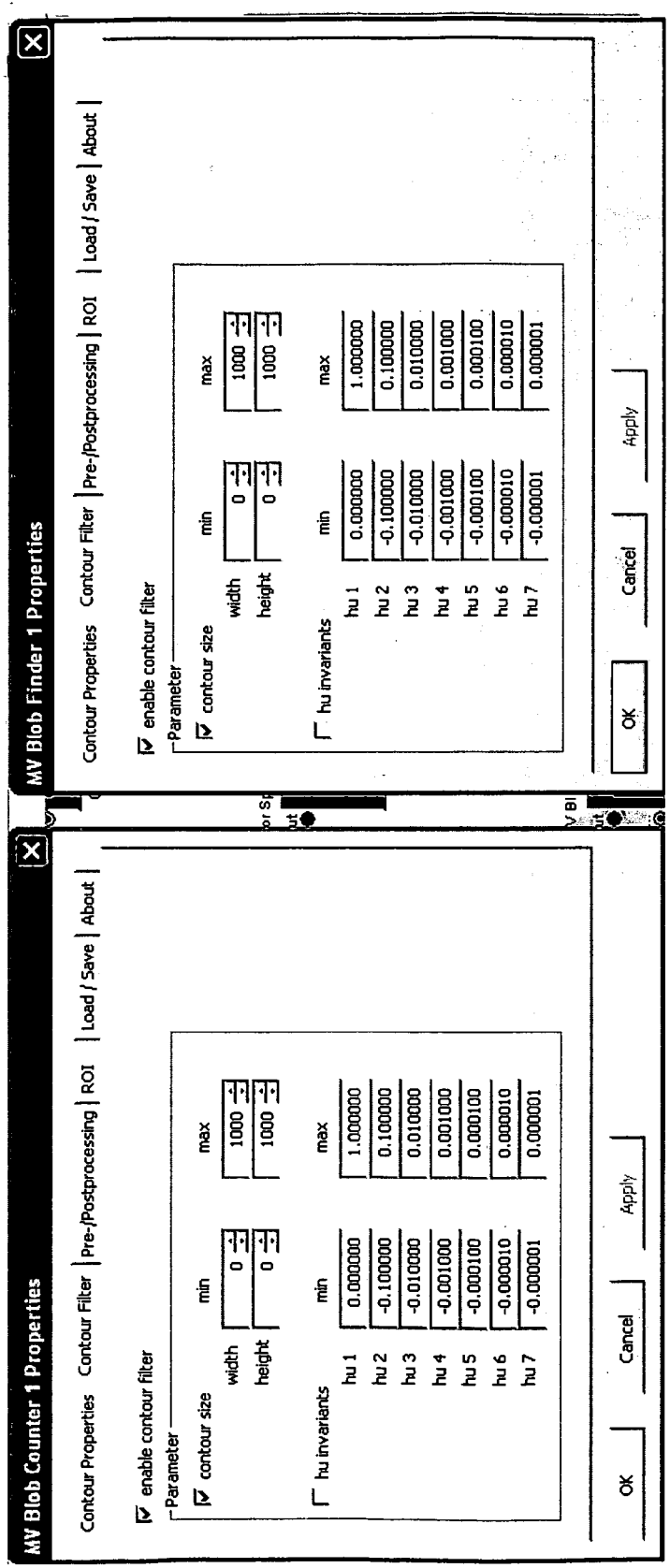
Figure 60:
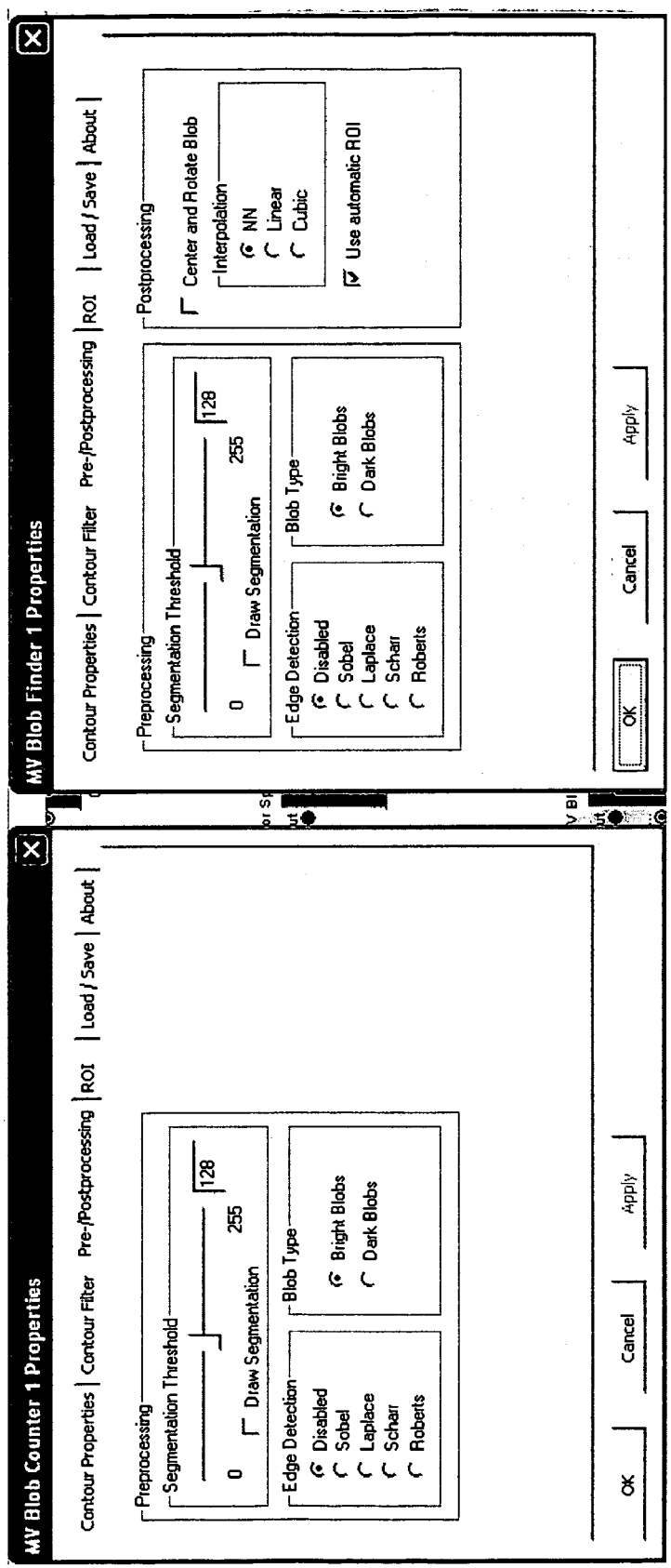

As shown in FIG. 55, a Topography filter step 636 is applied and is identical to that previously described, except that the image output from the Topography filter step is inverted as represented by step 637 and as shown in the Topography properties dialog box of FIG. 57. It may also be recognized that the topographically filtered image is inverted before the Segmentation filter is applied as shown by step 638 in FIG. 55. Also, as shown in a filter tab of a Segmentation properties dialog box, the binarization manual threshold is set to 230, as opposed to 10, to reflect the fact that the topographic output has been inverted.

Next, a Blob Counter function 640 and Blob Finder function 642 are somewhat different from that previously discussed above. As shown in properties dialog boxes of FIG. 58, the Blob Finder output does not include bounding rectangles, and the blob contours are not to be drawn. As shown in the filter tabs of the dialog boxes of FIG. 59, contour filtering is enabled with contour sizes of, for example, between 0 and 1,000 (instead of 10,000) pixels in width and height are selected. Finally, only bright (instead of dark) blobs are to be found, reflecting the inverted status of the image, as shown in the pre-/postprocessing tab of the properties dialog boxes of FIG. 60.

Figure 61:
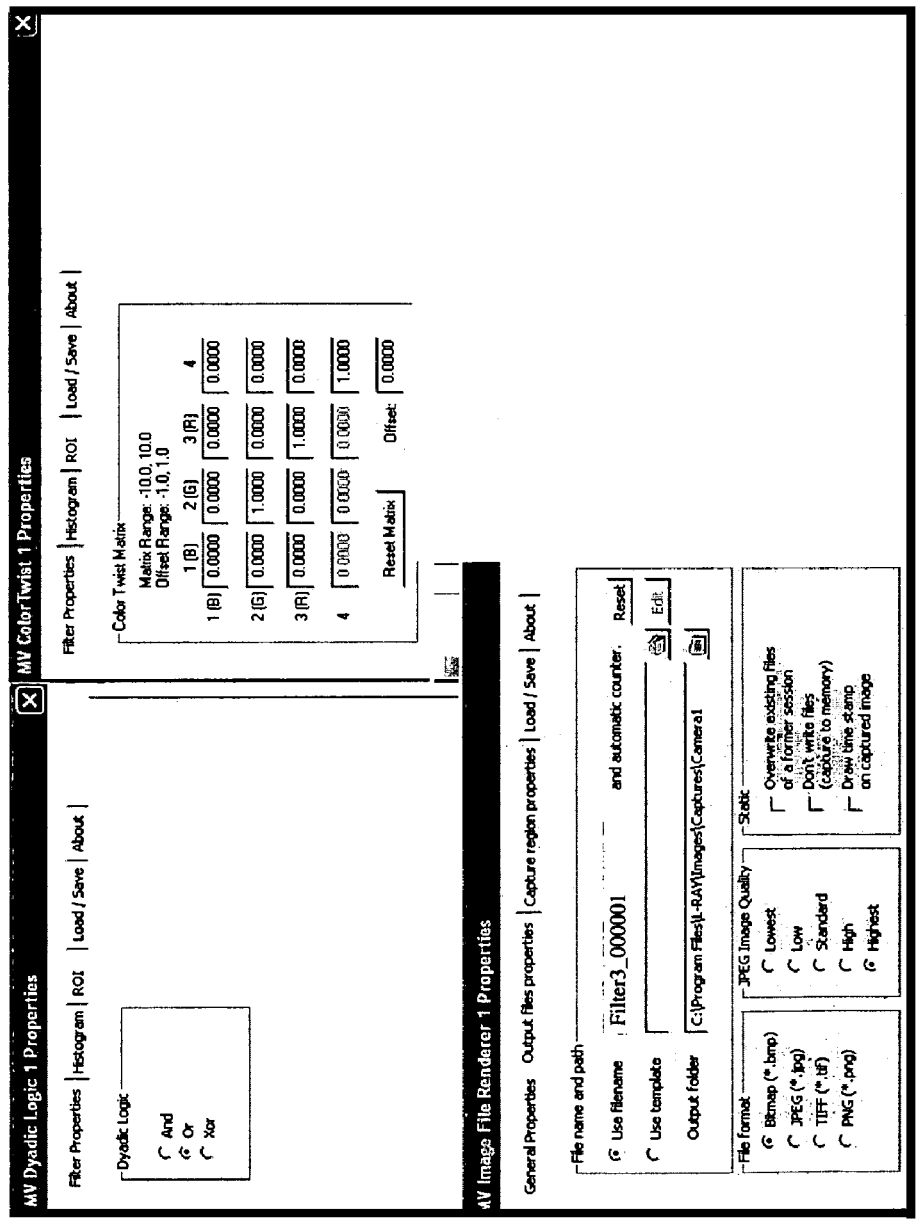
Figure 62:
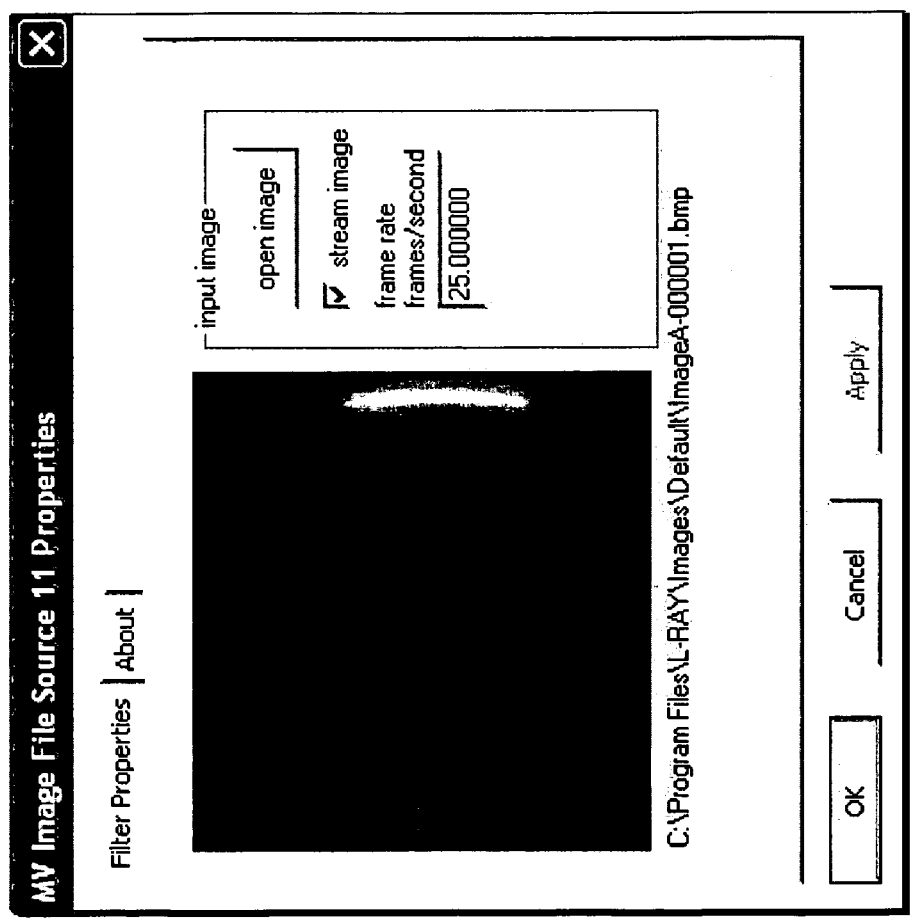

Referring to FIG. 56, a ColorTwist function is applied to the Blob Finder output to convert one or more of three color channels according to a 4×4 matrix specified as shown by the colortwist properties dialog box in FIG. 61. As discussed previously with respect to the image function touchbutton with reference to FIG. 14, the ColorTwist function preferably changes the color of the anomalies from dark or black to yellow. As depicted by step 644 of the flow chart of FIG. 55, the inverted analyzed image is overlaid on the baseline image with a digital dyadic logical "OR" function, as also depicted in the filter tab of the Dyadic Logic properties dialog box of FIG. 61. Before applying a Color Space Converter function, the baseline image is called from the saved image file ImageA-000001.bmp from the Image File Source 2 function from the Live Differencing routine described previously, as shown in the properties dialog of FIG. 62. Finally, the output from the logical OR function is saved using the Image File Renderer with the properties shown in FIG. 61. Those of ordinary skill in the art will recognize that the overlay CDI routine may contain more or less than the steps described herein to produce an overlaid CDI.

DVS Database

Figure 63:
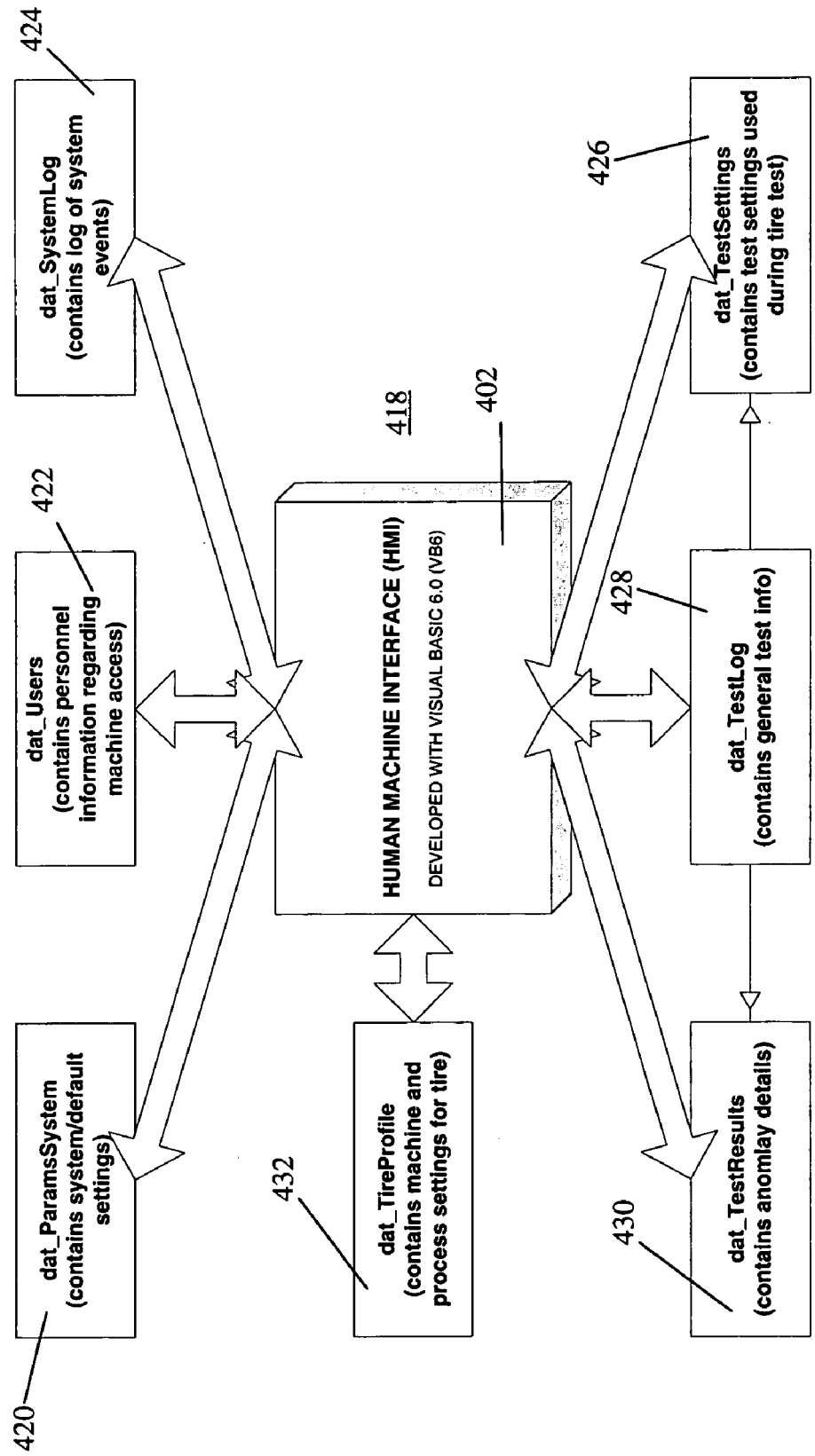
FIG. 63 is a block diagram of a software relationship between different tables of a database and a human machine interface of the differencing video system of FIG. 12.

FIG. 63 is a block diagram of a software relationship 418 between different tables of one of the databases 404 of FIG. 12 with the DVS HMI 402 of FIG. 12, wherein the tables are saved in a tables directory within a DVS database in an SQL Server Enterprise Manager. The DVS database includes the following tables with the listed characteristics or data: dat_ParamsSystem 420 including system default settings; dat_Users 422 including personnel data; dat_SystemLog 424 including system event descriptions; dat_TestSettings 426 including machine setup data per tire test; dat_TestLog 428 including general tire test data; dat_TestResults 430 including tire anomaly data; dat_TireProfile 432 including tire profile data; and may further include datParameters (not shown) which may be used as a dummy table. As used herein, the term data is interchangeable with the term characteristic.

As shown below in Table 1, the dat_ParamsSystem table contains default vacuum, file management, dome, display, and mode settings. VacuumSetpoint1 and 2 are the default limits for a given Tire Profile. A user can specify other limits within a Tire Profile as long as they do not exceed the VacuumMax or Min values.

TABLE 1

| Column Name | Data Type | Length | Description |
| --- | --- | --- | --- |
| VacuumMax | real | 4 | Maximum system vacuum |
| VacuumMin | real | 4 | Minimum system vacuum |
| VacuumSetPoint1 | real | 4 | Maximum default vacuum for differencing process |
| VacuumSetPoint2 | real | 4 | Minimum default vacuum for differencing process |
| ArchivePath | char | 10 | File path for archiving differencing images |
| FilenameTemplate | char | 10 | Template for differencing image file names, with typical syntax of: TireProfile name_TestID-Sector.bmp) |

TABLE 1-continued

| Column Name | Data Type | Length | Description |
| --- | --- | --- | --- |
| TestConfig | int | 4 | Display type (Raw, Enhanced, Analyzed); only applicable in auto-detect mode. |
| DomeSettlingTime | int | 4 | Time between dome decoupling and start of vacuum cycle. |
| AutoDetectEnabled | char | 1 | 1: auto-detect mode enabled; 0: not enabled |

As shown below in Table 2, the dat_Users table contains the names, passwords, and access level of users.

TABLE 2

| Column Name | Data Type | Length | Description |
| --- | --- | --- | --- |
| Name | char | 30 | Persons name (First and last) |
| Password | char | 10 | Persons password |
| AccessLevel | int | 4 | Level (operator, maint., supervisor, administrator) |

As shown below in Table 3, the dat_SystemLog contains a log of system events. All messages, warnings, and faults are saved to this table. A message is a statement regarding normal operation of the system. A warning alerts the user to a non-critical system/process issue. A fault alerts a user to a critical issue that must be attended to immediately in order to proceed further.

TABLE 3

| Column Name | Data Type | Length | Description |
| --- | --- | --- | --- |
| Severity | int | 4 | Event type (1: Message, 2: Warning, 3: Fault) |
| Description | char | 40 | Event |
| DateTime | datetime | 8 | Date/Time event occurred and was logged |

As shown below in Table 4, the dat_TestSettings table contains information regarding the machine setup and differencing analysis parameters of each tire tested.

TABLE 4

| Column Name | Data Type | Length | Description |
| --- | --- | --- | --- |
| ID | bigint | 4 | Incremental record number. Always unique. |
| TestID | bigint | 4 | Reference to TestID in dat_TestLog |
| TestArea | int | 4 | Area of tire tested (i.e. Crown, DOT, Lower Bead) |
| CameraGain | int | 4 | Gain of camera set in tire profile used |
| CameraExposure | int | 4 | Exposure of camera set in tire profile used |
| CameraBrightness | real | 4 | Brightness of camera set in tire profile used |
| CameraContrast | real | 4 | Contrast of camera set in tire profile used |
| CameraGamma | real | 4 | Gamma of camera set in tire profile used |
| CameraFocus | real | 4 | Focus of camera set in tire profile used |
| CameraIris | real | 4 | Iris of camera set in tire profile used |

TABLE 4-continued

| Column Name | Data Type | Length | Description |
|---|---|---|---|
| VacuumMax | real | 4 | Maximum vacuum set in tire profile used |
| VacuumMin | real | 4 | Minimum vacuum set in tire profile used |
| Pos1Vert | real | 4 | Vertical Position 1 set in tire profile used |
| Pos1VertClr | real | 4 | Vertical Clear Position 1 set in tire profile used |
| Pos1Horz | real | 4 | Horz. Position 1 set in tire profile used |
| Pos1HorzClr | real | 4 | Horz. Clear Position 1 set in tire profile used |
| Pos1Tilt | real | 4 | Tilt Position 1 set in tire profile used |
| Pos1TiltClr | real | 4 | Tilt Clear Position 1 set in tire profile used |
| Pos1Sectors | int | 4 | Sectors for Position 1 set in tire profile used |
| Pos2Vert | real | 4 | Vertical Position 2 set in tire profile used |
| Pos2VertClr | real | 4 | Vertical Clear Position 2 set in tire profile used |
| Pos2Horz | real | 4 | Horz. Position 2 set in tire profile used |
| Pos2HorzClr | real | 4 | Horz. Clear Position 2 set in tire profile used |
| Pos2Tilt | real | 4 | Tilt Position 2 set in tire profile used |
| Pos2TiltClr | real | 4 | Tilt Clear Position 2 set in tire profile used |
| Pos2Sectors | int | 4 | Sectors for Position 2 set in tire profile used |
| Pos3Vert | real | 4 | Vertical Position 3 set in tire profile used |
| Pos3VertClr | real | 4 | Vertical Clear Position 3 set in tire profile used |
| Pos3Horz | real | 4 | Horz. Position 3 set in tire profile used |
| Pos3HorzClr | real | 4 | Horz. Clear Position 3 set in tire profile used |
| Pos3Tilt | real | 4 | Tilt Position 3 set in tire profile used |
| Pos3TiltClr | real | 4 | Tilt Clear Position 3 set in tire profile used |
| Pos3Sectors | int | 4 | Sectors for Position 3 set in tire profile used |
| Pos4Vert | real | 4 | Vertical Position 4 set in tire profile used |
| Pos4VertClr | real | 4 | Vertical Clear Position 4 set in tire profile used |
| Pos4Horz | real | 4 | Horz. Position 4 set in tire profile used |
| Pos4HorzClr | real | 4 | Horz. Clear Position 4 set in tire profile used |
| Pos4Tilt | real | 4 | Tilt Position 4 set in tire profile used |
| Pos4TiltClr | real | 4 | Tilt Clear Position 4 set in tire profile used |
| Pos4Sectors | int | 4 | Sectors for Position 4 set in tire profile used |
| Pos5Vert | real | 4 | Vertical Position 5 set in tire profile used |
| Pos5VertClr | real | 4 | Vertical Clear Position 5 set in tire profile used |
| Pos5Horz | real | 4 | Horz. Position 5 set in tire profile used |
| Pos5HorzClr | real | 4 | Horz. Clear Position 5 set in tire profile used |
| Pos5Tilt | real | 4 | Tilt Position 5 set in tire profile used |
| Pos5TiltClr | real | 4 | Tilt Clear Position 5 set in tire profile used |
| Pos5Sectors | int | 4 | Sectors for Position 5 set in tire profile used |
| Pos6Vert | real | 4 | Vertical Position 6 set in tire profile used |
| Pos6VertClr | real | 4 | Vertical Clear Position 6 set in tire profile used |
| Pos6Horz | real | 4 | Horz. Position 6 set in tire profile used |
| Pos6HorzClr | real | 4 | Horz. Clear Position 6 set in tire profile used |
| Pos6Tilt | real | 4 | Tilt Position 6 set in tire profile used |
| Pos6TiltClr | real | 4 | Tilt Clear Position 6 set in tire profile used |
| Pos6Sectors | int | 4 | Sectors for Position 6 set in tire profile used |
| MinBlobWidth | real | 4 | Minimum blob width used for auto-detect |
| MaxBlobWidth | real | 4 | Maximum blob width used for auto-detect |
| MinBlobHeight | real | 4 | Minimum blob height used for auto-detect |
| MaxBlobHeight | real | 4 | Maximum blob height used for auto-detect |
| FilterLevel | int | 4 | Filter level used for auto-detect |
| DomeSettlingTime | int | 4 | Time b/w dome decoupling and vacuum cycle start. |

As shown below in Table 5, the dat_TestLog table stores general information regarding a tire test. A unique identification (TestID) is generated for each test with an incremental record number. Other tables that store test details then reference this unique identification.

TABLE 5

| Column Name | Data Type | Length | Description |
|---|---|---|---|
| TestID | bigInt | 8 | Incremental record number. Always unique. |
| CustomerName | char | 20 | Customer that the tire was tested for |
| Tester | char | 20 | Name of Tester/Operator |
| Manufacturer | char | 20 | Name of tire manufacturer (i.e. ACME) |
| Model | Char | 20 | Model of tire (i.e. Ruffrider) |
| [Size] | Char | 20 | Size of tire (i.e. P235/65R14) |
| DOT | Char | 15 | DOT number on tire |
| New | Char | 1 | Y for Yes or N for No |
| TireProfile | Char | 20 | Name of tire profile used for test |
| TestResult | Int | 4 | Pass/Fail |
| AutoDetectEnabled | Real | 4 | Logs whether system was in auto-detect mode or not |
| DateTimeStamp | Datetime | 8 | Date and Time of test |

As shown below in Table 6, the dat_TestResults table stores details about anomalies found in a certain area and sector of a tire. The TestId value provides the reference to the dat_TestLog table.

TABLE 6

| Column Name | Data Type | Length | Description |
|---|---|---|---|
| ID | bigInt | 8 | Incremental record number. Always unique. |
| TestID | bigInt | 8 | Reference to TestID in dat_TestLog |
| TestArea | Int | 4 | Area of tire tested (i.e. Crown, DOT, Lower Bead) |
| Sector | Int | 4 | Tire sector |
| Anomalies | Int | 4 | Number of anomalies in tire area and sector |

TABLE 6-continued

| Column Name | Data Type | Length | Description |
|---|---|---|---|
| SizeOfLgAnom | Real | 4 | Size of largest anomaly extrapolated from image in tire area and sector |

As shown below in Table 7, the dat_TireProfile table contains tire profiles. Tire profiles describe and define characteristics of the tire that are then used in the tire test process.

TABLE 7

| Column Name | Data Type | Length | Description |
|---|---|---|---|
| Name | char | 30 | Operator defined name for tire profile |
| CameraGain | int | 4 | Gain of camera set in tire profile used |
| CameraExposure | int | 4 | Exposure of camera set in tire profile used |
| CameraBrightness | real | 4 | Brightness of camera set in tire profile used |
| CameraContrast | real | 4 | Contrast of camera set in tire profile used |
| CameraGamma | real | 4 | Gamma of camera set in tire profile used |
| CameraFocus | real | 4 | Focus of camera set in tire profile used |
| CameraIris | real | 4 | Iris of camera set in tire profile used |
| VacuumMax | real | 4 | Maximum vacuum set in tire profile used |
| VacuumMin | real | 4 | Minimum vacuum set in tire profile used |
| Pos1Vert | real | 4 | Vertical Position 1 set in tire profile used |
| Pos1VertClr | real | 4 | Vertical Clear Position 1 set in tire profile used |
| Pos1Horz | real | 4 | Horz. Position 1 set in tire profile used |
| Pos1HorzClr | real | 4 | Horz. Clear Position 1 set in tire profile used |
| Pos1Tilt | real | 4 | Tilt Position 1 set in tire profile used |
| Pos1TiltClr | real | 4 | Tilt Clear Position 1 set in tire profile used |
| Pos1Sectors | int | 4 | Sectors for Position 1 set in tire profile used |
| Pos2Vert | real | 4 | Vertical Position 2 set in tire profile used |
| Pos2VertClr | real | 4 | Vertical Clear Position 2 set in tire profile used |
| Pos2Horz | real | 4 | Horz. Position 2 set in tire profile used |
| Pos2HorzClr | real | 4 | Horz. Clear Position 2 set in tire profile used |
| Pos2Tilt | real | 4 | Tilt Position 2 set in tire profile used |
| Pos2TiltClr | real | 4 | Tilt Clear Position 2 set in tire profile used |
| Pos2Sectors | int | 4 | Sectors for Position 2 set in tire profile used |
| Pos3Vert | real | 4 | Vertical Position 3 set in tire profile used |
| Pos3VertClr | real | 4 | Vertical Clear Position 3 set in tire profile used |
| Pos3Horz | real | 4 | Horz. Position 3 set in tire profile used |
| Pos3HorzClr | real | 4 | Horz. Clear Position 3 set in tire profile used |
| Pos3Tilt | real | 4 | Tilt Position 3 set in tire profile used |
| Pos3TiltClr | real | 4 | Tilt Clear Position 3 set in tire profile used |
| Pos3Sectors | int | 4 | Sectors for Position 3 set in tire profile used |
| Pos4Vert | real | 4 | Vertical Position 4 set in tire profile used |
| Pos4VertClr | real | 4 | Vertical Clear Position 4 set in tire profile used |
| Pos4Horz | real | 4 | Horz. Position 4 set in tire profile used |
| Pos4HorzClr | real | 4 | Horz. Clear Position 4 set in tire profile used |
| Pos4Tilt | real | 4 | Tilt Position 4 set in tire profile used |
| Pos4TiltClr | real | 4 | Tilt Clear Position 4 set in tire profile used |
| Pos4Sectors | int | 4 | Sectors for Position 4 set in tire profile used |
| Pos5Vert | real | 4 | Vertical Position 5 set in tire profile used |
| Pos5VertClr | real | 4 | Vertical Clear Position 5 set in tire profile used |
| Pos5Horz | real | 4 | Horz. Position 5 set in tire profile used |
| Pos5HorzClr | real | 4 | Horz. Clear Position 5 set in tire profile used |
| Pos5Tilt | real | 4 | Tilt Position 5 set in tire profile used |
| Pos5TiltClr | real | 4 | Tilt Clear Position 5 set in tire profile used |
| Pos5Sectors | int | 4 | Sectors for Position 5 set in tire profile used |
| Pos6Vert | real | 4 | Vertical Position 6 set in tire profile used |
| Pos6VertClr | real | 4 | Vertical Clear Position 6 set in tire profile used |
| Pos6Horz | real | 4 | Horz. Position 6 set in tire profile used |
| Pos6HorzClr | real | 4 | Horz. Clear Position 6 set in tire profile used |
| Pos6Tilt | real | 4 | Tilt Position 6 set in tire profile used |
| Pos6TiltClr | real | 4 | Tilt Clear Position 6 set in tire profile used |
| Pos6Sectors | int | 4 | Sectors for Position 6 set in tire profile used |
| TireManufacturer | real | 4 | Name of tire manufacturer (i.e. ACME) |
| TireModel | real | 4 | Model of tire (i.e. Ruffrider) |
| TireSize | real | 4 | Size of tire (i.e. P235/65R14) |
| Customer | real | 4 | Customer that the tire was tested for |
| NewTire | int | 4 | Y for Yes or N for No |
| MinBlobWidth | real | 4 | Minimum blob width used for auto-detect |
| MaxBlobWidth | real | 4 | Maximum blob width used for auto-detect |
| MinBlobHeight | real | 4 | Minimum blob height used for auto-detect |
| MaxBlobHeight | real | 4 | Maximum blob height used for auto-detect |

Substrate Data Collector HMI

Figure 64:
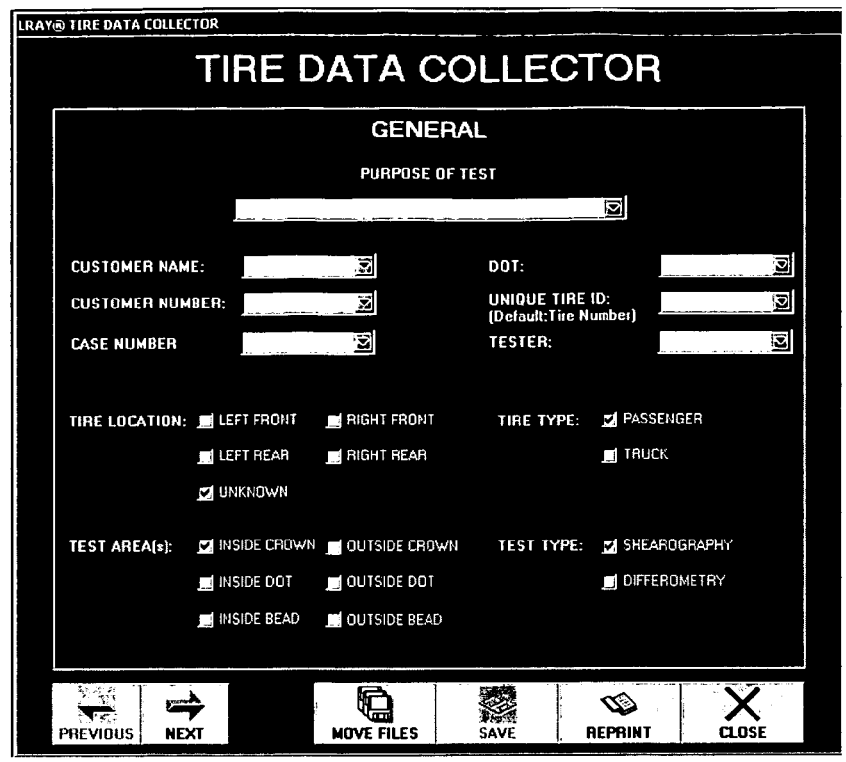

FIGS. 64 through 68 illustrate some of the functionality of a substrate data collector through several GUI screen shots. FIG. 64 illustrates a main screen that provides a user with the ability to move files to an archive directory, reprint or edit existing tire reports, and begin a tire report process. The program may be closed down by pressing the Close button.

Figure 65:
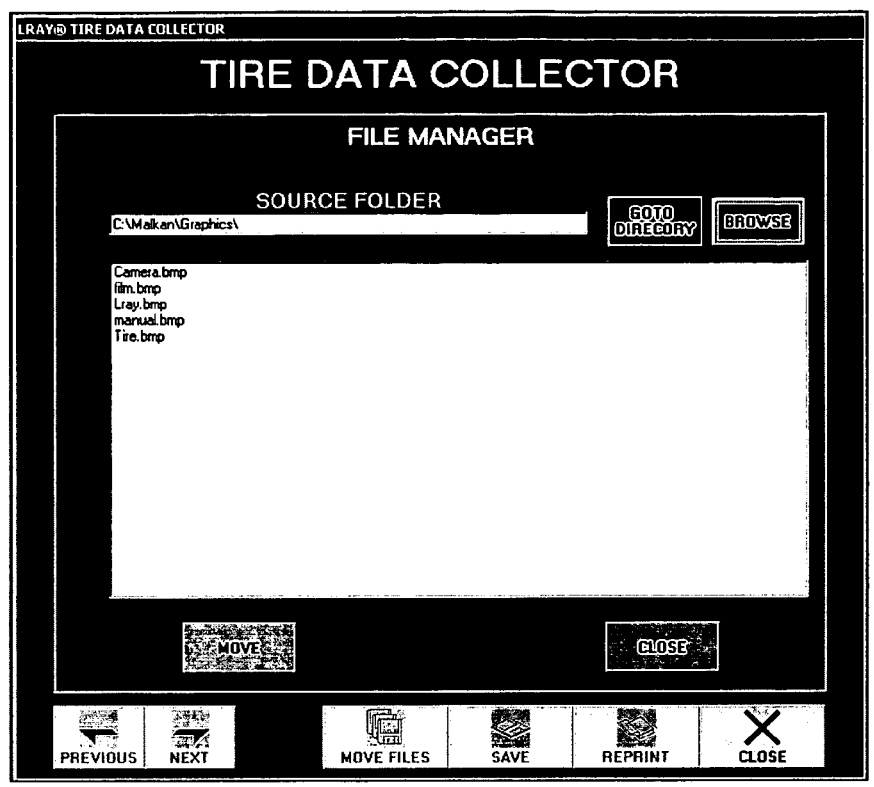

The Move Files button allows a user to move CDI's from a local directory to an archive directory, after a report has been created. Once a user presses the button, a Move Files screen is displayed as shown in FIG. 65. If the directory containing the CDI's is known, then a user can type in the directory in the Source Folder textbox and press GOTO DIRECTORY. Otherwise, a user can find the folder by browsing through the system folders, wherein a BROWSE button loads a browse folders dialogue box not unlike what Windows® users are accustomed to. Once a particular folder is selected, the listbox will be automatically populated with the bitmap images found in that folder. The user selects the files that need to be moved. Once all of the files have been selected, the MOVE button will begin the transfer process. The user will be asked via a popup dialog box to verify whether or not to make the move because the original files will be deleted. If YES on the dialog box is pressed, then the program will verify that the files follow the correct name format, so the files can be copied to the correct location, and if so will begin the transfer process. After the files have been moved, the listbox will be updated to reflect that the files no longer exist in the current directory. The CLOSE button may be pressed to exit this screen.

The REPRINT button allows the user to print past tire reports. Once the REPRINT button has been pressed, a popup dialog box will appear prompting the user to enter the Tire and Test Number for the tire report to be printed. After the Tire and Test Number have been entered, the user may press an OK button to continue or a CANCEL button to exit. Once the OK button has been pressed the tire report will be printed if the Tire and Test number entered are valid. It is contemplated that the software could include an edit function wherein existing reports could be retrieved, data therein edited, and re-saved.

To begin a tire report a user starts with data fields located in a General section of the screen. Fields containing drop-down menus can be used in one of two ways: a selection can be made from a drop-down menu or the user can type in the information if it does not exist in the drop-down menu. The preferred sequence for filling out the General form is as follows: 1) Select or type in the purpose of the test (i.e. R&D, Sales); 2) Select a customer name or enter a new one; 3) Select a customer number (menu items are dependent on customer name selected) or enter a new one; 4) Select a case number (menu items are dependent on customer number selected) or enter a new one; 5) Select a U.S. Department of Transportation (DOT) number (menu items are dependent on case number selected) or enter a new one; 6) Select a unique tire ID if testing a previously tested tire (menu items are dependent on case number selected), enter a new one (if unique marking exists and is a new test tire), or leave blank (if new test tire and no unique marking exist, wherein default id will be fire number). This field is used to distinguish tires having the same DOT number; 7) Select your name from the Tester drop-down menu or enter it if it does not exist; 8) Select the tire type, tire location, and the test type; 9) Select all of the tire areas that were tested; 10) Press next. If all of the data has not been filled out the user will be asked to complete the form in full.

Figure 66:

Referring now to FIG. 66, the Tire Characteristics screen is used to record characteristics or data about the tire like make, model, size, stiffness, whether new or used or clean or dirty, and environmental aspects of the tire test such as temperature and relative humidity, and notes fields. Under the title "Tire Characteristics" appears the filename syntax or scheme to be used in order for the Move Files function to work. If the user is creating a report on a previously tested tire the manufacturer, model, and size will automatically be filled out. If it is a new tire then the manufacturer, model, and size should be selected or filled out in the order just stated. The other fields can be filled in any order. When all the information has been entered the user can press the NEXT button to continue or the PREVIOUS button to go back to the previous screen.

Figure 67:
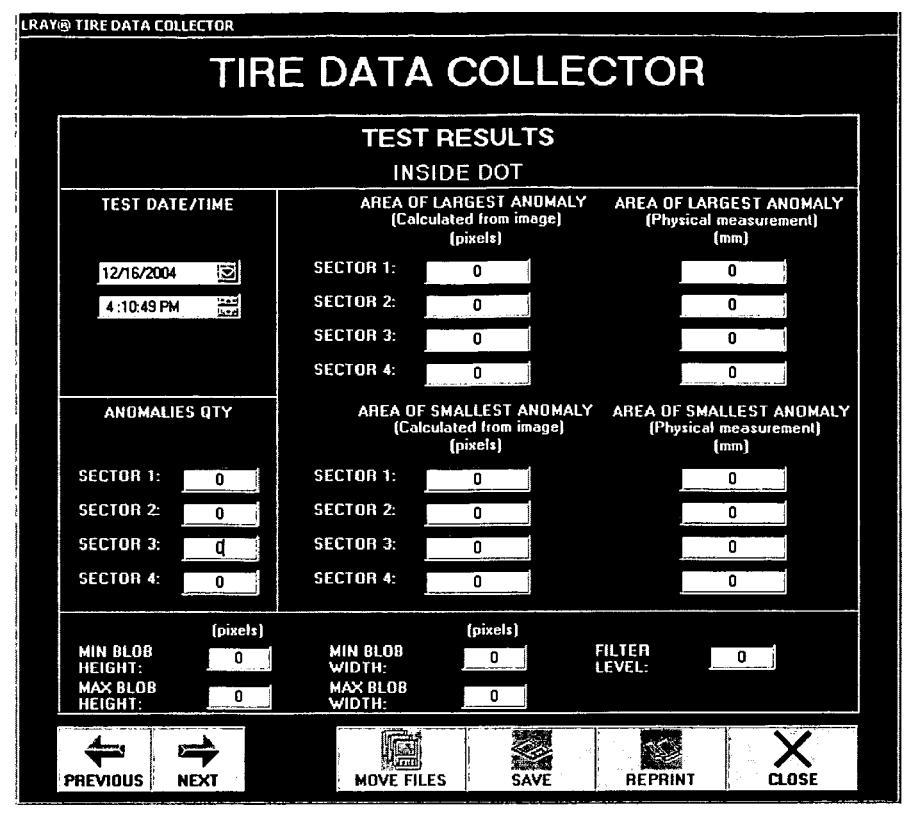

Referring now to FIG. 67, a Test Results screen is used to record certain data or characteristics of the tire testing such as the date, time, quantitative and qualitative anomaly details, and filter parameters (if tire was tested using the differencing process described herein). The anomaly details may include the quantity of anomalies per tire sector, the area of smallest and largest anomalies per sector, and the minimum and maximum heights and widths of the anomaly filter levels used. The area, heights, and widths may be measured and/or presented in pixels, millimeters, and/or inches. As indicated on the screen shot by the area under the title TEST RESULTS, a unique test results screen is preferably provided for each of the different tire areas tested. The various test results sections for any given tire may be as follows: inside bead, inside crown, inside DOT, outside bead, outside crown, and outside DOT, all of which are particular areas of a tire known to those of ordinary skill in the art of tire testing. When all of the information for the current area is entered, the NEXT button will display the next area to fill out. The tire areas requiring data depend on the areas checked in the General section. If all of the tire areas requiring data are filled out, then the NEXT button will prompt the user to determine if each area of the tire tested was done with the same fixture setup or not, via popup dialog box. The PREVIOUS button will display the previous test area or section.

Figure 68:
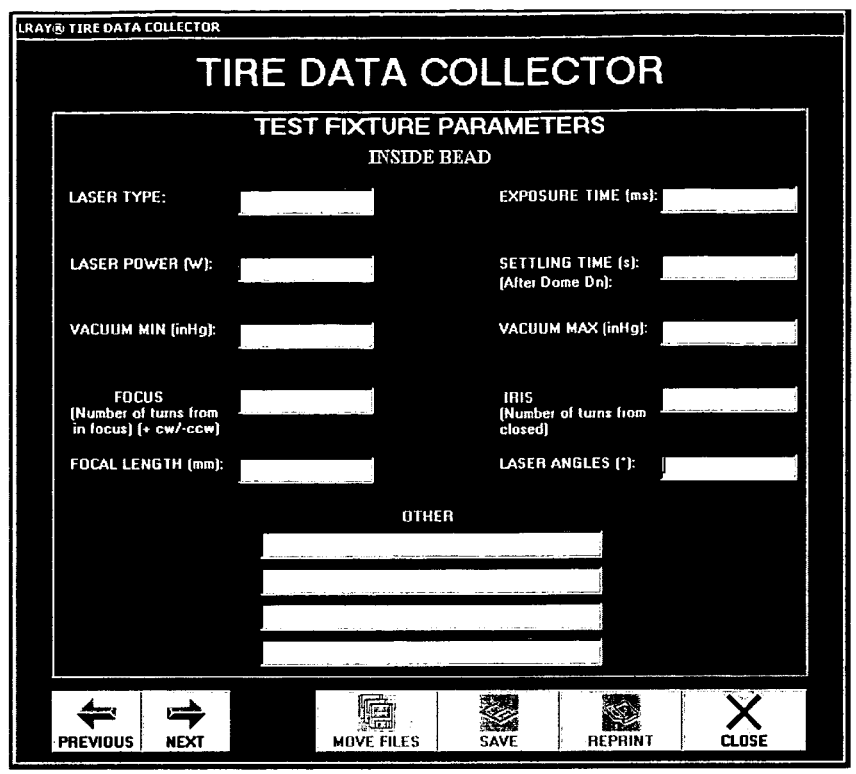

Referring now to FIG. 68, a Test Fixture Parameters screen is used to record machine settings used for the test. Machine settings are synonymous with machine characteristics or machine data, and may include the type of laser light source used, laser power in mW (milliwatts), laser angles, minimum and maximum vacuum test levels, and camera setting details such as camera exposure time, focus, focal length, iris, and the like. If different test settings were used for different areas of the tire, then the NEXT button will take the user to the next area where the same fields will need to be filled out. The various test fixture parameter sections for any given tire may be as follows: inside bead, inside crown, inside DOT, outside bead, outside crown, and outside DOT. If all the fields for all test areas have been filled the save button will be enabled. Pressing the SAVE button will prompt the user to determine whether or not to continue with the saving process. If the user clicks YES, then the data will be saved to the database and the user will be prompted to determine whether or not to print the report. Once the user clicks yes or no to print the report the user will be brought back to the General screen where the CDI's can be archived or moved and another test report can be filled out.

Substrate Data Collector Database

FIG. 69 is a block diagram of a software relationship 434 between different tables of one of the databases 404 of FIG. 12 with the Substrate Data Collector 406 of FIG. 12, wherein the tables are saved in a tables directory within a substrate data database in an SQL Server Enterprise Manager. The substrate database includes the following tables with the listed data: dat_ParamsCustomer 436 including customer data; dat_ParamsTires 438 including tire specifications; dat_ParamsTesters 440 including personnel data; dat_TestFixtureSetup 442 including machine setup data; dat_TestLog 444 including general tire test data; dat_TestResults 446 including tire anomaly details; and if desired, datParameters (not shown) which may be a dummy table. The substrate database may also include a reference, such as a filename, hyperlink, or the like, to one or more images associated with the tested substrate. Finally, a dummy table may be used that includes known fields to check the connection between the DVS HMI 402 of FIG. 12 and SQL.

Referring to Table 8 below, the dat_ParamsCustomer table contains all the customer information needed for the customer drop-down menus in the Tire Data Collector interface. If a tire for a new customer is being tested the tester will have to enter in the customer information manually, after which, the information will be saved for future use.

TABLE 8

| Column Name | Data Type | Length | Description |
|---|---|---|---|
| ID | Int | 4 | Incremental record number. Always unique. |
| CustomerName | Char | 40 | Name of customer (i.e. Acme Co.) |
| CustomerNumber | Char | 10 | Customer Number (Defined by L-RAY ®) |
| CaseNumber | Char | 20 | Case Number (Defined by customer) |

As shown in Table 9 below, the dat_ParamsTires table contains information regarding tires for the drop-down menus in the Tire data Collector interface. If certain tire characteristics or parameters do not exist then the parameters will have to be manually entered in via the Tire Data Collector interface and saved for future use.

TABLE 9

| Column Name | Data Type | Length | Description |
|---|---|---|---|
| ID | Int | 4 | Incremental record number. Always unique. |
| Manufacturer | Char | 20 | Name of tire manufacturer (i.e. ACME) |
| Model | Char | 20 | Model of tire (i.e. Ruffrider) |
| [Size] | Char | 20 | Size of tire (i.e. P235/65R14) |

Referring to Table 10 below, the dat_ParamsTester table contains personnel data or characteristics for those people testing tires and provides the information for the Tester drop-down menu in the Tire Data Collector interface. Depending on the system a person may select their name from a drop-down menu or they may have to swipe their badge and/or enter a password to login to the system. If a person does not exist in the table they will have to be entered in manually via the operator interface.

TABLE 10

| Column Name | Data Type | Length | Description |
|---|---|---|---|
| Tester | Char | 20 | Name of Tester/Operator |

As shown in Table 11 below, the dat_TestFixture table contains data or characteristics regarding the machine setup and differencing analysis parameters. The TestId field provides the reference to the dat_TestLog table.

TABLE 11

| Column Name | Data Type | Length | Description |
|---|---|---|---|
| ID | bigInt | 8 | Incremental record number. Always unique. |
| TestID | bigInt | 8 | Reference to TestID in dat_TestLog |
| TestArea | Int | 4 | Area of tire tested (i.e. Crown, DOT, Lower Bead) |
| Focus | Real | 4 | Number of turns clockwise or counter-clockwise from focus |
| Iris | Real | 4 | Number of turns from closed iris position |
| FocalLen | Real | 4 | Focal length of camera |
| LaserType | char | 10 | Type of laser (i.e. Krypton, Lasr Diode) |
| LaserPower | Int | 4 | Power of laser |
| laserAngle | Int | 4 | Angle of lasers |
| Exposure | Int | 4 | Exposure time of cameras |
| DomeSettlingTime | Int | 4 | Time between dome closing and test starting |
| MinVacuum | Real | 4 | Initial vacuum level for vacuum cycle |
| MaxVacuum | Real | 4 | Maximum vacuum for vacuum cycle |
| FilterLevel | Int | 4 | Filter level used when analyzing a differenced image |
| MinBlobWidth | Real | 4 | Minimum blob (anomaly) width |
| MaxBlobWidth | Real | 4 | Maximum blob (anomaly) width |
| MinBlobHeight | Real | 4 | Minimum blob (anomaly) height |
| MaxBlobHeight | Real | 4 | Maximum blob (anomaly) height |
| TireTestFixtureDesc1 | Char | 40 | Note |
| TireTestFixtureDesc2 | Char | 40 | Note |
| TireTestFixtureDesc3 | Char | 40 | Note |
| TireTestFixtureDesc4 | Char | 40 | Note |

Referring to Table 12 below, the dat_TestLog table stores general data or characteristics regarding a tire test. A unique id (TestID) is generated for each test (incremental record number). Other tables that store test details then reference this id.

TABLE 12

| Column Name | Data Type | Length | Description |
|---|---|---|---|
| TestID | bigInt | 8 | Incremental record number. Always unique. |
| TireNumber | bigInt | 8 | Each tire tested is assigned a unique, incremental, number. |
| TestNumber | Int | 4 | Each tire is assigned a unique, incremental, number based on the number of tests performed (i.e. if tire number 7 was being tested for the third time it would be assigned tire number 7 test number 3) |
| CustomerNumber | Char | 10 | Customer Number (Defined by L-RAY ®) |
| CaseNumber | char | 20 | Case Number (Defined by customer) |
| Tester | char | 20 | Name of Tester/Operator |
| TestType | char | 1 | D for Differencing or S for Shearography |
| TireType | Char | 1 | P for Passenger or T for Truck |

TABLE 12-continued

| Column Name | Data Type | Length | Description |
| --- | --- | --- | --- |
| Manufacturer | char | 20 | Name of tire manufacturer (i.e. ACME) |
| Model | Char | 20 | Model of tire (i.e. Ruffrider) |
| [Size] | Char | 20 | Size of tire (i.e. P235/65R14) |
| DOT | Char | 15 | DOT number on tire |
| TireNumDescr | Char | 20 | Unique marking on tire that may exist to distinguish it from other tires |
| TireLocation | Char | 10 | Right/Left Front or Right/Left Rear or Unknown |
| Used | Char | 1 | Y for Yes or N for No |
| Cleanliness | Char | 20 | Acceptable or Dirty |
| TireStiffness | Int | 4 | Subjective value from 1 to 5 regarding how stiff a tire is. |
| Temperature | Real | 4 | Temperature of tire |
| Humidity | Real | 4 | Humidity of air around tire |
| SpreadSettlingTime | Int | 4 | Time between spreading and testing |
| TireCharDesc1 | Char | 40 | Notes |
| TireCharDesc2 | Char | 40 | Notes |
| TireCharDesc3 | Char | 40 | Notes |
| TireCharDesc4 | Char | 40 | Notes |
| Purpose | Char | 25 | Reason for test (i.e. R&D, Sales, etc.) |
| DateTimeStamp | Datetime | 8 | Date and Time of test |

Referring to Table 13 below, the dat_TestResults table stores data or characteristics about the anomalies found in a certain area and sector of a tire. The TestId value provides the reference to the dat_TestLog table.

TABLE 13

| Column Name | Data Type | Length | Description |
| --- | --- | --- | --- |
| ID | bigInt | 8 | Incremental record number. Always unique. |
| TestID | bigInt | 8 | Reference to TestID in dat_TestLog |
| TestArea | Int | 4 | Area of tire tested (i.e. Crown, DOT, Lower Bead) |
| Sector | Int | 4 | Tire sector |
| Anomalies | Int | 4 | Number of anomalies in tire area and sector |
| SizeOfLgAnom | Real | 4 | Size of largest anomaly extrapolated from image in tire area and sector |
| SizeOfSmAnom | Real | 4 | Size of smallest anomaly extrapolated from image in tire area and sector |
| PhysicalSizeOfLgAnom | Real | 4 | Size of largest anomaly obtained from cutting the tire and measuring the anomaly in tire area and sector |
| PhysicalSizeOfSmAnom | Real | 4 | Size of smallest anomaly obtained from cutting the tire and measuring the anomaly in tire area and sector |

The order of execution or performance of the methods illustrated and described herein is not essential, unless otherwise specified. That is, elements or steps of the methods may be performed in any order, unless otherwise specified, and that the methods may include more or less elements than those disclosed herein. For example, it is contemplated that executing or performing a particular element before, contemporaneously with, or after another element is within the scope of the invention.

As used in this specification and claims, the terms "for example," "for instance," and "such as," and the verbs "comprising," "having," "including," and their other verb forms, when used in conjunction with a listing of one or more components or other items, are each to be construed as open-ended, meaning that that the listing is not to be considered as excluding other, additional components or items. Moreover, directional words such as top, bottom, upper, lower, radial, circumferential, axial, lateral, longitudinal, vertical, horizontal, and the like are employed by way of description and not limitation. Other terms are to be construed using their broadest reasonable meaning unless they are used in a context that requires a different interpretation. When introducing elements of the present invention or the embodiment(s) thereof, the articles "a," "an," "the," and "said" are intended to mean that there are one or more of the elements.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or the scope of the invention. For example the number and type of lasers to be utilized can vary substantially; and the software in the computer that is described herein can be varied depending upon the changes in technology with respect to the computer or computer devices and updates to the types of software or customer requirements.

We claim:

1. A method of non-destructive testing comprising:
non-destructively testing an object over a range of test levels;
shining coherent light onto the object;
directly receiving the coherent light substantially as reflected straight from the object;
capturing in a processor the reflected coherent light over the range of test levels as a plurality of digital images of the object;
calculating differences between pixel values of a plurality of pairs of digital images of the plurality of digital images;
adding the pixel value differences of the plurality of pairs of digital images to yield at least one cumulative differential image; and displaying, from apparatus electronically connected to the processor, the output from the processor.

2. The method of claim 1 wherein the capturing step includes capturing the plurality of digital images of the object at predefined test levels of the range of test levels.

3. The method of claim 1 wherein the capturing step includes capturing the plurality of digital images of the object at least two different test levels over the range of test levels.

4. The method of claim 1 wherein the calculating step includes calculating differences between pixel values of a first pair of at least two pairs of digital images and of a second pair of at least two pairs of digital images wherein the first and second pairs have a digital image in common.

5. The method of claim 1 wherein the calculating step includes calculating differences between pixel values of a first pair of at least two pairs of digital images and of a second pair of at least two pairs of digital images wherein the first pair has first and second digital images and the second pair has third and fourth digital images, such that the first and second pairs have no digital images in common.

6. The method of claim 1 wherein the calculating step includes:
calculating differences between pixel values of first, second, and third pairs of at least three pairs of digital images;
adding the differences of the first and second pairs of the at least three pairs of digital images to yield a first cumulative differential image; and
adding pixel values of the first cumulative differential image to the differences of the third pair of the at least three pairs of digital images to yield at least one more cumulative differential image.

7. The method of claim 1 further comprising:
the capturing step including capturing the plurality of digital images of the object at predefined test levels of the range of test levels;
calculating differences between pixel values of a first, second, and third pairs of at least three pairs of digital images, wherein the first pair has first and second digital images, the second pair has third and fourth digital images, and the third pair have fifth and sixth digital images, such that the first, second, and third pairs have no digital images in common;
adding the differences of the first and second pairs of the at least three pairs of digital images to yield a first cumulative differential image; and
adding pixel values of the first cumulative differential image to the differences of the third pair of the at least three pairs of digital images to yield at least one more cumulative differential image.

8. The method of claim 1 further comprising:
brightening the at least one cumulative differential image; and
smoothing the at least one cumulative differential image.

9. The method of claim 1 further comprising:
inverting the at least one cumulative differential image to yield at least one inverted image;
topographically filtering the at least one inverted image to yield at least one topographically filtered image; and
segment filtering the at least one topographically filtered image to yield at least one enhanced image.

10. The method of claim 9 further comprising:
quantifying anomalies in the at least one enhanced image to yield at least one analyzed image.

11. The method of claim 10 wherein the quantifying step includes:
applying at least one of an anomaly counter and an anomaly finder process to the at least one enhanced image to yield at least one analyzed image.

12. The method of claim 1 wherein at further comprising:
topographically filtering the at least one cumulative differential image to yield at least one topographically filtered image;
segment filtering the at least one topographically filtered image to yield at least one enhanced image;
quantifying anomalies in the at least one enhanced image to yield at least one analyzed image; and
digitally overlaying at least one of the at least one analyzed image and the at least one enhanced image on a baseline image of the plurality of images.

13. A product processed according to the method of claim 1.

14. The method of claim 1 wherein the capturing step includes discretely capturing the reflected coherent light at two test levels over the range of test levels as two digital images.

15. The method of claim 1 wherein the directly receiving step includes receiving the coherent light that has neither passed through a birefringent or shearing optic material nor has been reflected from a beam splitter.

16. The method of claim 1 wherein the non-destructive testing step includes continuously progressively stressing the object to expose the object to continuously progressive levels of deformation.

17. A method of detecting an anomaly in an object comprising:
providing a source of coherent light;
shining the light onto the object surface, thereby generating a reflected light from the object;
stressing the object over a range of test levels;
providing a reflected light receiving apparatus for receiving the light reflected directly from the tire when the object is in a stressed and unstressed condition;
capturing the reflected light over the range of test levels as a plurality of digital images of the object;
calculating differences between pixel values of a plurality of pairs of digital images of the plurality of digital images;
adding the pixel value differences of the plurality of pairs of digital images to yield at least one cumulative differential image;
providing a processor which views and compares images of reflected light from the reflected light receiving apparatus when the object is stressed and unstressed thereby ascertaining an anomaly in the object and generates an output from the comparison; and
displaying, from apparatus electronically connected to the processor, the output from the processor.

18. An anomaly detector apparatus for detecting an anomaly in an object comprising:
a source of coherent light to shine the light onto the object surface with the light being reflected from the object;
a stressing apparatus, which can stress the object over a range of test levels;
a reflected light receiving apparatus for receiving the light reflected directly from the object when the object is in a stressed and unstressed condition;
a processor, which compares images of reflected light from the reflected light receiving apparatus when the object is stressed and unstressed thereby ascertaining an anomaly in the object and which generates an output from the comparison, the processor being adapted to:

capture the reflected light over the range of test levels as a plurality of digital images of the object;

calculate differences between pixel values of a plurality of pairs of digital images of the plurality of digital images; and add the pixel value differences of the plurality of pairs of digital images to yield at least one cumulative differential image; and a display apparatus electronically connected to the processor for displaying the output from the processor.

19. A non-destructive testing system comprising:

a non-destructive testing apparatus to test an object over a range of test levels;

a light source to shine coherent light onto the object;

an imaging device to directly receive light substantially as reflected straight from the object and thereby capture a plurality of digital images of the object over the range of test levels;

a memory for storing the plurality of digital images and for storing a computer-executable program;

an input device for receiving input from an operator;

an output device for transmitting output to the operator;

a processor in communication with the imaging device, the memory, and the input and output devices, the processor being adapted to:

execute the computer-executable program to store the plurality of images in the memory, calculate differences between pixel values of a plurality of pairs of digital images of the plurality of digital images, and add the pixel value differences of the plurality of pairs of digital images to yield at least one cumulative differential image.

* * * * *

UNITED STATES PATENT AND TRADEMARK OFFICE
CERTIFICATE OF CORRECTION

PATENT NO.       : 7,436,504 B2                                    Page 1 of 1
APPLICATION NO.  : 11/066672
DATED            : October 14, 2008
INVENTOR(S)      : Shaw et al.

It is certified that error appears in the above-identified patent and that said Letters Patent is hereby corrected as shown below:

ON THE TITLE PAGE, ITEM [73]:

Delete "Shear Graphics, LLC" and insert -- Shearographics, LLC --.

Signed and Sealed this

Twenty-fifth Day of November, 2008

JON W. DUDAS
*Director of the United States Patent and Trademark Office*